United States Patent
Lipkens et al.

(10) Patent No.: US 9,670,477 B2
(45) Date of Patent: Jun. 6, 2017

(54) ACOUSTOPHORETIC DEVICE FOR ANGLED WAVE PARTICLE DEFLECTION

(71) Applicant: FloDesign Sonics, Inc., Wilbraham, MA (US)

(72) Inventors: Bart Lipkens, Hampden, MA (US); Walter M. Presz, Wilbraham, MA (US); Kedar Chitale, West Hartford, CT (US); Thomas J. Kennedy, III, Wilbraham, MA (US); Ben Ross-Johnsrud, Wilbraham, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

(21) Appl. No.: 15/143,481

(22) Filed: Apr. 29, 2016

(65) Prior Publication Data
US 2016/0319270 A1    Nov. 3, 2016

Related U.S. Application Data

(60) Provisional application No. 62/316,933, filed on Apr. 1, 2016, provisional application No. 62/154,690, filed on Apr. 29, 2015.

(51) Int. Cl.
*C12N 13/00* (2006.01)
*B01D 21/00* (2006.01)
(Continued)

(52) U.S. Cl.
CPC ......... *C12N 13/00* (2013.01); *A61M 1/3678* (2014.02); *B01D 21/283* (2013.01); *C12M 47/04* (2013.01);
(Continued)

(58) Field of Classification Search
CPC ..................................................... C12N 13/00
(Continued)

(56) References Cited

U.S. PATENT DOCUMENTS 2,473,971 A    6/1949  Ross
2,667,944 A    2/1954  Crites
(Continued)

FOREIGN PATENT DOCUMENTS

DE    30 27 433 A1    2/1982
DE    196 48 519 A1    6/1998
(Continued)

OTHER PUBLICATIONS

Alvarez et al.; Shock Waves, vol. 17, No. 6, pp. 441-447, 2008.
(Continued)

*Primary Examiner* — Kevin Joyner
*Assistant Examiner* — Holly Mull
(74) *Attorney, Agent, or Firm* — Fish & Richardson P.C.

(57) ABSTRACT

Devices for separating materials from a host fluid are disclosed. The devices include a flow chamber, an ultrasonic transducer, and a reflector. The ultrasonic transducer and reflector create an angled acoustic standing wave oriented at an angle relative to the direction of mean flow through the flow chamber. The angled acoustic standing wave results in an acoustic radiation force having an axial force component that deflects the materials, so that the materials and the host fluid can thus be separated. The angled acoustic standing wave can be oriented at an angle of about 20° to about 70° relative to the direction of mean flow through the flow chamber to deflect, collect, differentiate, or fractionate the materials from the fluid flowing through the device at flow rates of about 400 mL/min up to about 700 mL/min.

28 Claims, 22 Drawing Sheets

(51) Int. Cl.
- *G01N 29/00* (2006.01)
- *B01D 21/28* (2006.01)
- *A61M 1/36* (2006.01)
- *C12M 1/00* (2006.01)
- *G01N 15/00* (2006.01)
- *G01N 15/10* (2006.01)
- *G01N 15/14* (2006.01)

(52) U.S. Cl.
CPC .. *G01N 15/1484* (2013.01); *B01L 2400/0436* (2013.01); *B01L 2400/0439* (2013.01); *G01N 2015/0053* (2013.01); *G01N 2015/1006* (2013.01); *G01N 2015/149* (2013.01)

(58) Field of Classification Search
USPC .......................................................... 422/128
See application file for complete search history.

(56) References Cited

U.S. PATENT DOCUMENTS

| | | |
|---|---|---|
| 3,372,370 A | 3/1968 | Cyr |
| 3,555,311 A | 1/1971 | Weber |
| 4,032,438 A | 6/1977 | Koblanski |
| 4,055,491 A | 10/1977 | Porath-Furedi |
| 4,065,784 A | 1/1978 | Sma |
| 4,065,875 A | 1/1978 | Srna |
| 4,118,649 A | 10/1978 | Schwartzman et al. |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,280,823 A | 7/1981 | Szonntagh |
| 4,320,659 A | 3/1982 | Lynnworth et al. |
| 4,321,696 A | 3/1982 | Kanda |
| 4,344,448 A | 8/1982 | Potts |
| 4,398,325 A | 8/1983 | Piaget et al. |
| 4,475,921 A | 10/1984 | Barmatz |
| 4,523,682 A | 6/1985 | Barmatz et al. |
| 4,666,595 A | 5/1987 | Graham |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Ju-Zhen |
| 4,821,838 A | 4/1989 | Chen |
| 4,836,684 A | 6/1989 | Javorik et al. |
| 4,878,210 A | 10/1989 | Mitome |
| 4,983,189 A | 1/1991 | Peterson et al. |
| 5,094,758 A | 3/1992 | Chang |
| 5,147,562 A | 9/1992 | Heyman |
| 5,164,094 A | 11/1992 | Stuckart |
| 5,192,450 A | 3/1993 | Heyman |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,608,692 A | 3/1997 | Toda |
| 5,626,767 A | 5/1997 | Trampler et al. |
| 5,679,254 A | 10/1997 | Chakrabarti |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,951,456 A | 9/1999 | Scott |
| 6,051,111 A | 4/2000 | Prestidge |
| 6,090,295 A | 7/2000 | Raghavarao et al. |
| 6,166,231 A | 12/2000 | Hoeksema |
| 6,205,848 B1 | 3/2001 | Faber et al. |
| 6,216,538 B1 | 4/2001 | Yasuda et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,482,327 B1 | 11/2002 | Mori et al. |
| 6,487,095 B1 | 11/2002 | Malik et al. |
| 6,492,762 B1 | 12/2002 | Pant et al. |
| 6,592,821 B1 | 7/2003 | Wada et al. |
| 6,649,069 B2 | 11/2003 | DeAngelis |
| 6,699,711 B1 | 3/2004 | Hahn et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,845,785 B2 | 9/2014 | Kusuura |
| 8,865,476 B2 | 10/2014 | Ward |
| 8,873,051 B2 | 10/2014 | Kaduchak et al. |
| 8,889,388 B2 | 11/2014 | Wang et al. |
| 8,932,520 B2 | 1/2015 | Goddard |
| 8,956,536 B2 | 2/2015 | Yu et al. |
| 8,956,538 B2 | 2/2015 | Rietman et al. |
| 8,991,259 B2 | 3/2015 | Laugharn, Jr. et al. |
| 8,991,614 B2 | 3/2015 | Rose et al. |
| 8,997,998 B2 | 4/2015 | Curran et al. |
| 9,011,699 B2 | 4/2015 | Dionne et al. |
| 9,049,520 B2 | 6/2015 | Korbler et al. |
| 9,079,127 B2 | 7/2015 | Chen et al. |
| 9,090,663 B2 | 7/2015 | Lin et al. |
| 9,096,823 B1 | 8/2015 | Branch et al. |
| 9,101,664 B2 | 8/2015 | Lopez et al. |
| 9,126,177 B2 | 9/2015 | Laugharn, Jr. et al. |
| 9,134,271 B2 | 9/2015 | Ward |
| 9,174,189 B2 | 11/2015 | Wu |
| 9,176,504 B2 | 11/2015 | Chiou |
| 9,180,490 B2 | 11/2015 | Tai |
| 9,207,066 B2 | 12/2015 | Martini et al. |
| 9,228,183 B2 | 1/2016 | Lipkens et al. |
| 9,272,234 B2 | 3/2016 | Lipkens et al. |
| 9,321,050 B2 | 4/2016 | Rose et al. |
| 9,339,744 B2 | 5/2016 | Kaduchak et al. |
| 9,340,435 B2 | 5/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |

(56) References Cited

U.S. PATENT DOCUMENTS

| | | |
|---|---|---|
| 9,391,542 B2 | 7/2016 | Wischnewskiy et al. |
| 9,403,114 B2 | 8/2016 | Kusuura |
| 9,410,256 B2 | 8/2016 | Dionne et al. |
| 9,416,344 B2 | 8/2016 | Lipkens et al. |
| 9,422,328 B2 | 8/2016 | Kennedy, III et al. |
| 9,457,139 B2 | 10/2016 | Ward et al. |
| 9,458,450 B2 | 10/2016 | Lipkens et al. |
| 9,464,303 B2 | 10/2016 | Burke |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller |
| 2003/0195496 A1 | 10/2003 | Maguire et al. |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2007/0272618 A1 | 11/2007 | Gou et al. |
| 2007/0284299 A1 | 12/2007 | Xu et al. |
| 2008/0105625 A1 | 5/2008 | Rosenberg et al. |
| 2008/0217259 A1 | 9/2008 | Siversson |
| 2008/0245709 A1 | 10/2008 | Kaduchak et al. |
| 2008/0272034 A1 | 11/2008 | Ferren et al. |
| 2008/0272065 A1 | 11/2008 | Johnson |
| 2009/0029870 A1 | 1/2009 | Ward et al. |
| 2009/0045107 A1 | 2/2009 | Ward et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0178716 A1 | 7/2009 | Kaduchak et al. |
| 2009/0194420 A1 | 8/2009 | Mariella, Jr. et al. |
| 2009/0226994 A1 | 9/2009 | Lemor et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0163126 A1 | 6/2012 | Campbell et al. |
| 2012/0175012 A1 | 7/2012 | Goodwin et al. |
| 2012/0267288 A1 | 10/2012 | Chen et al. |
| 2012/0325727 A1 | 12/2012 | Dionne et al. |
| 2012/0325747 A1 | 12/2012 | Rietman et al. |
| 2012/0328477 A1 | 12/2012 | Dionne et al. |
| 2012/0329122 A1 | 12/2012 | Lipkens et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1 | 1/2014 | Lipkens et al. |
| 2014/0017758 A1 | 1/2014 | Kniep et al. |
| 2014/0080207 A1 | 3/2014 | Lipkens et al. |
| 2014/0154795 A1 | 6/2014 | Lipkens et al. |
| 2014/0190889 A1 | 7/2014 | Rietman et al. |
| 2014/0202876 A1 | 7/2014 | Dionne et al. |
| 2014/0216992 A1 | 8/2014 | Rose et al. |
| 2014/0230912 A1 | 8/2014 | Aider |
| 2014/0231315 A1 | 8/2014 | Laurell et al. |
| 2014/0319077 A1 | 10/2014 | Lipkens et al. |
| 2014/0329997 A1 | 11/2014 | Kennedy et al. |
| 2014/0339085 A1 | 11/2014 | Bouyer et al. |
| 2014/0377834 A1 | 12/2014 | Presz et al. |
| 2015/0053561 A1 | 2/2015 | Ward |
| 2015/0079655 A1 | 3/2015 | Laugharn, Jr. et al. |
| 2015/0104845 A1 | 4/2015 | Huang et al. |
| 2015/0118692 A1 | 4/2015 | Johnson et al. |
| 2015/0125948 A1 | 5/2015 | Lipkens et al. |
| 2015/0158743 A1 | 6/2015 | Rietman et al. |
| 2015/0160116 A1 | 6/2015 | Yu et al. |
| 2015/0176001 A1 | 6/2015 | Lipkens et al. |
| 2015/0191716 A1 | 7/2015 | Lipkens et al. |
| 2015/0196911 A1 | 7/2015 | Rose et al. |
| 2015/0209695 A1 | 7/2015 | McCarthy et al. |
| 2015/0252317 A1 | 9/2015 | Lipkens et al. |
| 2015/0253226 A1 | 9/2015 | Augustsson et al. |
| 2015/0260689 A1 | 9/2015 | Kaduchak |
| 2015/0265961 A1 | 9/2015 | Davey et al. |
| 2015/0272537 A1 | 10/2015 | Laugharn, Jr. et al. |
| 2015/0274550 A1 | 10/2015 | Lipkens et al. |
| 2015/0308971 A1 | 10/2015 | Bisgaard et al. |
| 2015/0321129 A1 | 11/2015 | Lipkens et al. |
| 2015/0330887 A1 | 11/2015 | Shin |
| 2016/0002070 A1 | 1/2016 | Lipkens et al. |
| 2016/0008532 A1 | 1/2016 | Fiering et al. |
| 2016/0008782 A1 | 1/2016 | Suslick et al. |
| 2016/0016180 A1 | 1/2016 | Lopez et al. |
| 2016/0025116 A1 | 1/2016 | Vulto et al. |
| 2016/0030660 A1 | 2/2016 | Sun et al. |
| 2016/0059206 A1 | 3/2016 | Chen et al. |
| 2016/0089620 A1 | 3/2016 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0129370 A1 | 5/2016 | Lipkens et al. |
| 2016/0145563 A1 | 5/2016 | Berteau et al. |
| 2016/0146797 A1 | 5/2016 | Lin et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0184822 A1 | 6/2016 | Wu et al. |
| 2016/0201024 A1 | 7/2016 | Gadini et al. |
| 2016/0202153 A1 | 7/2016 | Gadini et al. |
| 2016/0208213 A1 | 7/2016 | Doyle et al. |
| 2016/0230168 A1 | 8/2016 | Kaduchak |
| 2016/0237394 A1 | 8/2016 | Lipkens et al. |
| 2016/0237395 A1 | 8/2016 | Lipkens et al. |

FOREIGN PATENT DOCUMENTS

| | | |
|---|---|---|
| DE | 10 2008 006 501 A1 | 9/2008 |
| EP | 0 292 470 B1 | 11/1988 |
| EP | 1 254 669 B1 | 11/2002 |
| GB | 2 420 510 A | 5/2006 |
| JP | 9-136090 | 5/1997 |
| WO | WO 87/07178 A1 | 12/1987 |
| WO | WO 90/05008 | 3/1990 |
| WO | WO 02/072234 A1 | 9/2002 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |

(56) References Cited

FOREIGN PATENT DOCUMENTS

| WO | WO 2011/131947 A2 | 10/2011 |
|---|---|---|
| WO | WO 2011/161463 A2 | 12/2011 |
| WO | WO 2013/043297 A1 | 3/2013 |
| WO | WO 2013/055517 A1 | 4/2013 |
| WO | WO 2014/014941 A1 | 1/2014 |
| WO | WO 2014/055219 A2 | 4/2014 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.
Castro; Tunable gap and quantum quench dynamics in bilayer graphene; Jul. 13, 2010; Mathematica Summer School.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Hill et al.; Ultrasonic Particle Manipulation; Microfluidic Technologies for Miniaturized Analysis Systmes, Jan. 2007, pp. 359-378.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006) 321-328.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et a.; An Industrial-Prototype Acoustic Array for Real-Time Emulsion Layer Detection in Oil Storage Tanks; IEEE Sensors Journal, vol. 9, No. 12, Dec. 2009.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; DOI: 10.1038/NNANO.2009.177.
Seymour et al, J. Chem. Edu., 1990, 67(9), p. 763, published Sep. 1990.
Wang et al.; Retention and Viability Characteristics of Mammalian Cells in an Acoustically Driven Polymer Mesh; Biotechnol. Prog. 2004, pp. 384-387 (2004).
Annex to Form PCT/ISA/206—Communication Relating to the Results of the Partial International Search Report, dated Jul. 18, 2013.
European Search Report of European Application No. 11769474.5 Dated Oct. 10, 2012.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2012/051804 dated Nov. 16, 2012.
International Search Report and Written Opinion of International Application No. PCT/US2013/037404 Dated Jun. 21, 2013.
International Search Report and Written Opinion of International Application No. PCT/US2013/032705 dated Jul. 26, 2013.
International Search Report and Written Opinion of International Application No. PCT/US2013/050729 Dated Sep. 25, 2013.
International Search Report dated Feb. 18, 2014 in corresponding PCT Application No. PCT/US2013/059640.
International Search Report for corresponding PCT Application Serial No. PCT/US2014/015382 dated May 6, 2014.
International Search Report for PCT/US2014/035557 dated Aug. 27, 2014.
International Search Report for PCT/US2014/043930 dated Oct. 22, 2014.
International Search Report for PCT/US2014/046412 dated Oct. 27, 2014.
International Search Report for PCT/US2014/064088 dated Jan. 30, 2015.
Extended European Search Report for Application No. EP 12833859.7 dated Mar. 20, 2015.
International Search Report and Written Opinion for International Application No. PCT/US2015/010595 dated Apr. 15, 2015.
International Search Report for PCT/US2015/019755 dated May 4, 2015.
International Search Report mailed Jul. 30, 2015 for International Application No. PCT/US2015/030009.
International Search Report for PCT/US2015/039125 dated Sep. 30, 2015.
European Search Report of European Application No. 11796470.0 dated Jan. 5, 2016.
phys. org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.
A White Paper Describing Produces Water from Production of Crude Oil, Natural Gas, and Coal Bed Methane, Jan. 2004, 87 pages.
Aboobaker et al., "Mathematical modeling of the movement of suspended particles subjected to acoustic and flow fields," Appled Mathematical Modelling, 2005, 29: 515-532.
Aboobaker et al., "Fractionation and Segregation of Suspended Particles Using Acoustic and Flow Fields," Journal of Environmental Engineering © ASCW, 427-434, May 2003.
Acosta et al., "Acoustic-Structure Interaction Modeling of Piezoelectric Transducer in Fluid Medium," COMSOL Conference, Europe, 2012, 1 page.
ACUSEP Project, Integrated whole blood acoustophoresis and homogeneous nucleic acid detection cartridge for rapid sepsis diagnostics, Dec. 2010-May 2014, 3 pages.
ACUSEP Report Summary, Periodic Report Summary—ACUSEP (Integrated whole blood acoustophoresis and homogeneous nucleic acid detection cartridge for rapid sepsis diagnostics), 2013, 2 pages.
ACUSEP Result in Brief, Rapid diagnosis of sepsis, 2013, 2 pages.
Adams and Soh, "Tunable acoustophoretic band-pass particle sorter," Applied Physics Letters, 2010, 97: 064103.
Adams et al., "High-throughput, temperature-controlled microchannel acoustophoresis device made with rapid prototyping," J. Microchem. Microeng., 2012, 22: 075017.
Adams et al., "Microfluidic Acoustic Plateletpheresis," 14th International Conference on Miniaturized Systems for Chemistry and Life Sciences, Gronigen, The Netherlands, Oct. 2010, 232-234.
Adler and Breazeale, "Generation of Fractional Harmonics in a Resonant Ultrasonic Wave System," The Journal of the Acoustical Society of America, 48: 5, 1077-1083, 1970.

(56) References Cited

OTHER PUBLICATIONS

Adler et al., "Comments on Generation of Fractional Harmonics in a Resonant Ultrasonic Wave System," J. Acoust. Soc. Amer. 48, 429-431, 1970.
Agilent Impedance Measurement Handbook, "A Guide to Measurement Technology and Techniques 4th Edition," Agilent Technologies, Inc. 2013.
Agrawal and Pottsmith, "Instruments for particle size and settling velocity observations in sediment transport," Marine Geology, 2000, 168: 89-114.
Ahmadun et al., "Review of Technologies for Oil and Gas Produced Water Treatment," Journal of Hazardous Materials, 170: 530-551, 2009.
Ai et al., "Separation of *Escherichia coli* Bacteria from Peripheral Blood Mononuclear Cells Using Standing Surface Acoustic Waves," Anal. Chem. 2013, 85: 9126-9134.
Alix-Panabieres and Pantel, "Challenges in circulating tumour cell research," Nature Reviews, Sep. 2014, 14: 623-631.
Allegra and Hawley, "Attenuation of Sound in Suspensions and Emulsions: Theory and Experiments," The Journal of the Acoustical Society of America, 1972, 1545-1564.
Almas Temple Club, "Corporate WaterVision 2010: Draft Agenda," 5 pages, Jun. 7-9, 2010.
Almas Temple Club, "Corporate WaterVision 2010: Sponsorship Offer," 2 pages, Jun. 7-9, 2010.
Amirkulova, "Acoustic and Elastic Multiple Scattering and Radiation from Cylindrical Structures," Graduate School—New Brunswick, Rutgers, The State University of New Jersey, Oct. 2014, 250 pages.
Andersen et al., "Forces Acting on Microparticles in Acoustofluidic Systems," Department of Micro- and Nanotechnology, Technical University of Denmark, Jun. 2009, 167 pages.
Anderson et al., "The effect of large openings on cavity amplification at ultrasonic frequencies," J. Acoust. Soc. Am., Dec. 2002, 112: 2771-2778.
Anderson et al., "The Physics and Technology of Ultrasonic Particle Separation in Air," WCU 2003, Sep. 2003, 1615-1621.
Anderson et al., "Use of a curved reflector to amplify ultrasonic standing waves in an air-filled channel," J. Acoust. Soc. Am., Mar. 2005, 117: 1122-1128.
Andre Bakker., Lecture 14—Multiphase Flows, "Applied Computational Fluid Dynamics," Andre Bakker, 2002-2006.
Andrea Prosperetti., Computational Methods for Multiphase Flow, Jul. 2009.
Antfolk et al., "Focusing of sub-micrometer particles and bacteria enabled by two-dimensional acoustophoresis," Lab Chip, 2014, 14: 2791-2799.
Anthes, "Save Blood, Save Lives," Nature, Apr. 2015, 520: 24-26.
Apfel et al., "Studies of acousto-electrically levitated drop and particle clusters and arrays," J. Acoust. Soc. Am., May 1999, L1-L6.
Aqudo et al., "GFP-specific CD8 T cells enable targeted cell depletion and visualization of T-cell interactions," Nature Biotechnology, Dec. 2015, 33: 1287-1292.
Araz and Lal, "Frequency Addressable Acoustic Collection, Separation and Mixing in a PZT Driven Glass Capillary Microfluidic," 14th International Conference on Miniaturized Systems for Chemistry and Life Sciences, Gronigen, The Netherlands, Oct. 2010, 1919-1921.
Asatekin et al., "Anti-Fouling Ultrafiltration Membranes Containing Polyacrylonitrile-Graft-Poly (ethylene oxide) Comb Copolymer Additives," Journal of Membrane Science, 298: 136-146, 2007.
Asatekin et al., "Oil Industry Wastewater Treatment with Fouling Resistant Membranes Containing Amphiphilic Comb Copolymers," Environ. Sci. Technol. 7 pages, 2009.
ATCC Animal Cell Culture Guide: tips and techniques for continous cell lines, 2014, 39 pages.
ATS Medical, Inc. Annual Report 2005, 76 pages.
ATS Medical/ErySave Questions and Answers, Apr. 2004, 2 pages.

Augustsson et al., "Automated and temperature-controlled micro-PIV measurements enabling long-term-stable microchannel acoustophoresis characterization," Lab Chip, 2011, 4152-4164.
Augustsson et al., "Extraction of Circulating Tumor Cells From Blood Using Acoustophoresis," 14th International Conference on Miniaturized Systems for Chemistry and Life Sciences, Oct. 2010, 1592-1594.
Augustsson et al., "Iso-acoustic focusing of cells for size-insensitive acousto-mechanical phenotyping," Nature Communications, 2016, 7: 11556.
Avlonitis et al, "Energy consumption and membrane replacement cost for seawater RO desalination plants," Desalination, 2003, 157: 151-158.
Baddour and Kolios, "The fluid and elastic nature of nucleated cells: Implications from the cellular backscatter response," J. Acoust. Soc. Am., Jan. 2007, 121: EL16-EL22.
Baddour et al., "High-frequency ultrasound scattering from microspheres and single cells," J. Acoust. Soc. Am., Feb. 2005, 117: 934-943.
Bakken and Olsen, "Buoyant Densities and Dry-Matter Contents of Microorganisms: Conversion of a Measured Biovolume into Biomass," Applied and Environmental Microbiology, Apr. 1983, 45: 1188-1195.
Band et al., "Influence of specially modulated ultrasound on the water desalination process with ion-exchange hollow fibers," Desalination, 1997, 109: 303-313.
Bao et al., "Transfection of a Reporter Plasmid into Cultured Cells by Sonoporation In Vitro," Ultrasound in Med. & Biol., 1997, 23: 953-959.
Bar-Meir, Genick, "Basics of Fluid Mechanics: Chapter 13: Multi-Phase Flow," Version 0.3.4.0, Jul. 25, 2013.
Barnkob et al, "Measuring acoustic energy density in microchannel acoustophoresis using a simple and rapid light-intensity method," Lab Chip, 12: 2337-2344.
Barnkob et al., "Acoustic radiation- and streaming-induced microparticle velocities determined by microparticle image velocimetry in an ultrasound symmetry plane," Physical Review, 2012, 86: 056307.
Barnkob et al., "An Automated Full-Chip Micro-PIV Setup for Measuring Microchannel Acoustophoresis: Simultaneous Determination of Forces From Acoustic Radiation and Acoustic Streaming," 14th International Conference on Miniaturized Systems for Chemistry and Life Sciences, Gronigen, Netherlands, Oct. 2010, 1247-1249.
Barnkob et al., "Measuring the local pressure amplitude in microchannel acoustophoresis," Lab Chip, 2010, 10: 563-570.
Barnkob, "Acoustofluidics in microsystems: investigation of resonances," Department of Micro- and Nanotechnology, Technical University of Denmark, Jun. 2009, 138 pages.
Barnkob, "Physics of Microparticle Acoustophoresis: Bridging Theory and Experiment," Department of Micro- and Nanotechnology, Technical University of Denmark, Aug. 2012, 214 pages.
Bazou et al., "Molecular adhesion development in a neural cell monolayer forming in an ultrasound trap," Molecular Membrane Biology, May-Jun. 2005, 22(3):229-240.
Beenakker et al., "Many-Sphere Hydrodynamic Interactions: III. The Influence of a Plane Wall," Physica, 1984, 127A: 451-472.
Beitinjaneh et al., "Toxic Leukoencephalopathy following Fludarabine-Associated Hematopoietic Cell Transplantation," Biol Blood Marrow Transplant, 2011, 17: 300-308.
Benes et al., "Separation of Dispersed Particels by Drifting Ultrasonic Resonance Fields," Ultrasonics International 91 Conference Proceedings, Oct. 22, 2013, 167-166.
Bertin et al., "Universal morphologies of fluid interfaces deformed by the radiation pressure of acoustic or electromagnetic waves," Physical Review Letters, , Dec. 2012, 109: 244304-1-244304-5.
Beyer, "Radiation pressure—the history of a mislabeled tensor," J. Acoust. Soc. Am., Apr. 1978, 63: 1025-1030.
Bhardwaj et al., "Microfluidic device based on a micro-hydrocyclone for particle-liquid separation," Lab Chip, 2011, 11: 4012-4021.

(56) References Cited

OTHER PUBLICATIONS

Bilgili et al., "Efficiency and Cost Analysis of Cell Saver Auto Transfusion System in Total Knee Arthroplasty," Balkan Med J., 2014, 31: 149-53.
Blackhurst et al., "Direct and Indirect Water Withdrawals for U.S. Industrial Sectors," Environ. Sci. Technol. 44: 6, 2126-2130, 2010.
Blackstock et al., "Thermoviscous Attenuation of Plane, Periodic, Finite-Amplitude Sound Waves," The Journal of the Acoustical Society of America, 36: 3, 1964.
Borgnis, "Theory of Acoustic Radiation Pressure," Jul. 1951, 109 pages.
Bortz et al., "Klebsiella pneumoniae Flocculation Dynamics," Bull Math Biol., Apr. 2008, 70: 745-768.
Brennen., "Fundamentals of Multiphase Flows," California Institute of Technology, Pasadena, California, Cambridge University Press, 2005.
Bromfield, Surgical & Dental Transducers Suitable for Single Use Applications, UIA Symposium San Diego, Mar. 2006, 28 pages.
Bronden et al., "Differential Distribution of Lipid Microemboli After Cardiac Surgery," Ann Thorac Surg, 2006, 81: 643-9.
Brooker et al., "Cardiotomy Suction: A Major Source of Brain Lipid Emboli During Cardiopulmonary Bypass," Ann Thorac Surg., 1998, 65: 1651-1655.
Brown., "Design Considerations for Piezoelectric Polymer Ultrasound Transducers," IEEE Transactions on Ultrasonics, Ferroelectrics, and Frequency Control, 47:6, 1377-1396, 2000.
Brown., "The Effects of Material Selection for Backing and Wear Protection/Quarter-Wave Matching of Piezoelectric Polymer Ultrasound Transducers," IEEE Ultrasonics Symposium, 4 pages, 2000.
Bruckert et al., "Dictyostelium discoideum adhesion and motility under shear flow: experimental and theoretical approaches," Journal of Muscle Research and Cell Motility, 2002, 23: 651-658.
Brus, "Microfuidics and ultrasound acoustophoresis," Lecture notes for the advanced CISM school, Jun. 2010, 64 pages.
Bruus et al., "COMSOL Analysis of Acoustic Streaming and Microparticle Acoustophoresis," Lab Chip, 2011, 11: 4152-4164.
Bryan et al., "Measurement of mass, density, and volume during the cell cycle of yeast," PNAS, 107: 3, 999-1004, 2010.
Budwig et al., "Ultrasonic particle size fractionation in a moving air stream," Ultrasonics, 2010, 50: 26-31.
Buick et al., "Application of the acousto-optic effect to pressure measurements in ultrasound fields in water using a laser vibrometer," Rev. Sci. Intrum., Oct. 2004, 75: 3203-3207.
Bunnell et al., "Adipose-derived Stem Cells: Isolation, Expansion and Differentiation," Methods, Jun. 2008, 45: 115-120.
Burguillos et al., "Microchannel Acoustophoresis does not Impact Survival or Function of Microglia, Leukocytes or Tumor Cells," PLOS One, May 2013, 8: e64233.
Butler, "Separation of a Brewing Yeast Strain of *Saccharomyces cerevisiae* Based on Cellular Age," Department of Food Science and Agricultural Chemistry, 162 pages, 2002.
Buzas et al., "Emerging role of extracellular vesicles in inflammatory diseases," Nat. Rev. Rheumatol, Jun. 2014, 10: 356-364.
Cabañas Sorando et al., "Patterns of Particles Aggregation and Streaming in Resonating Fluids," AIP Conf. Proc., May 2012, 1433(1):757-760; doi: 10.1063/1.3703291.
Cappon and Keesman, "Design basis of industrial acoustic separators," 2013 Joint UFFC, EFTF and PFM Symposium, 2013, 299-302.
Cappon and Keesman, "Numerical Modeling, Calibration, and Validation of an Ultrasonic Separator," IEE Transactions on Ultrasonics, Ferroelectrics, and Frequency Control, Mar. 2013, 60: 614-621.
Cappon et al., "Concentration based flow control in acoustic separation of suspensions," Separation and Purification Technology, 2013, 103: 321-327.
Carugo et al., "Contrast agent-free sonoporation: The use of an ultrasonic standing wave microfluidic system for the delivery of pharmaceutical agents," Biomicrofluidics, 2011, 5: 044108.

Cavitation Technical Study, Novacav, available online on or before Sep. 17, 2012, URL <http://www.corporauk.com/documents/Novacav%20Cavitation.pdf>, 23 pages.
Cents et al., "Measuring Bubble, Drop and Particle Sizes in Multiphase Systems with Ultrasound," AIChE Journal, Nov. 2004, 50: 2750-2762.
Chalikian et al., "Temperature Dependences of the Acoustic Nonlinearity Parameter B/A of Aqueous Solutions of Amino Acids," J. Acoust. Soc. Am. 91: 1, 52-58, 1992.
Charlebois and Pelton, "Quantitative 2D and 3D Schlieren Imaging for Acoustic Power and Intensity Measurements," Medical Electronics, Jun. 1995, 66-73.
Chen et al., "Application of nano $TiO_2$ towards polluted water treatment combined with electro-photochemical method," Water Research, 2003, 37: 3815-3820.
Chen et al., "The effect of surface agitation on ultrasound-mediated gene transfer in vitro," J. Acoust. Soc. Am., Oct. 2004, 116: 2440-2450.
Cheng et al., "Design, Fabrication, and Performance of a Flextensional Transducer Based on Electrostrictive Polyvinylidene Fluoride-Trifluoroethylene Copolymer," IEEE Transactions on Ultrasonics, Ferroelectrics, and Frequency Control, 49:9, 1312-1320, 2002.
Cheng et al., "Dynamic Beam Modification Using Dimples," Journal of Vibration and Acoustics, 130: 9 pages, 2008.
Chhabra et al., "Drag on Chains and Agglomerates of Spheres in Viscous Newtonian and Power Law Fluids," The Canadian Journal of Chemical Engineering, Aug. 1995, 73: 566-571.
Chiang, "Solid-Liquid Separation," 2005, 12 pages.
Chinnely et al., "The schlieren image of two-dimensional ultrasonic fields and cavity resonances," J. Acoust. Soc. Am., Jan. 1997, 101: 250-256.
Cho et al., "Translocation of microparticles in a fluidflow by adjusting the operating frequency of ultrasonic standing wave (USW)," 2011 IEEE International Ultrasonics Symposium Proceedings, 2011, 1510-1513.
Chong et al., "Fouling in reverse osmosis: Detection by non-invasive techniques," Desalination, 2007, 204: 148-154.
Chouaib et al., "Hypoxic stress: obstacles and opportunities for innovative immunotherapy of cancer," Oncogene, 2016, 1-7.
Chun et al., "Biodegradable PLGA Microcarriers for Injectable Delivery of Chondrocytes: Effect of Surface Modification on Cell Attachment and Function," Biotechnol. Prog., 2004, 20: 1797-1801.
Chung et al., "Dynamical System Analysis of *Staphylococcus epidermidis* Bloodstream Infection," Shock, Nov. 2008, 30: 518-526.
Cinbis et al., "Effect of surface tension on the acoustic radiation pressure-induced motion of the water-air interface," J. Acoust. Soc. Am., Oct. 1993, 94: 2365-2372.
Clift and Weber, "Bubbles, Drops and Particles," 1978, 394 pages.
Clincke et al., "Very High Density of CHO Cells in Perfusion by ATF or TFF in WAVE BioreactorTM. Part I. Effect of the Cell Density on the Process," Biotechnol. Prog., 2013, 29: 754-767.
Clincke et al., "Very High Density of Hamster Ovaiy Cells in Perfusion by Alternating Tangential Flow or Tangential Flow Filtration in WAVE Bioreactor™—Part II: Applications for Antibody Production and Cryopreservation," Biotechnol. Prog., 29: 3, 768-777, 2013.
Coakley et al., "Cell Manipulation in Ultrasonic Standing Wave Fields," J. Chem. Tech. Biotechnol., 1989, 44: 43-62.
Collins et al., "Particle separation using virtual deterministic lateral displacement (vDLD)," Lab on a Chip, Mar. 2014, 14: 1595-1603.
Collins, "Problems associated with the massive transfusion of stored blood," Surgery, Feb. 1974, 75: 274-295.
Colombo, "Multiphysics Simulations in the Ultrasonic Industry," COMSOL, 2012, URL <https://www.comsol.com/paper/download/151395/colombo_abstract.pdf>, 1 page (abstract only).
Colombo, "Multiphysics Simulations in the Ultrasonic Industry," COMSOL, 2012, URL <https://www.comsol.com/paper/multiphysics-simulations-in-the-ultrasonic-industry-13201>, 1 page (poster).
Colton et al., "Recommendations for Extractables and Leachables Testing," Extractables and Leachables Subcommittee of the Bio-Process Systems Alliance, Dec. 2007, 5: 36-49.

(56) References Cited

OTHER PUBLICATIONS

Conference Report: International Workshop on Numerical Methods for Non-Newtonian Flows (Blois Castle, Mar. 25-28, 2012), Journal of Non-Newtonian Fluid Mechanics, 2003, 1-2.
Costa-Silva et al., "Pancreatic cancer exosomes initiate pre-metastatic niche formation in the liver," Nature Cell Biology, Jun. 2015, 17: 816-826.
Courtney et al., "Dexterous manipulation of microparticles using Bessel-function acoustic pressure fields," Applied Physics Letter, 2013, 102: 123508.
Courtney et al., "Independent trapping and manipulation of microparticles using dexterous acoustic tweezers," Applied Physics Letters, 2014, 104: 154103.
Courtney et al., "Manipulation of microparticles using phasecontrollable ultrasonic standing waves," J. Acoust. Soc. Am., Oct. 2010, 128: EL195-EL199.
Cousin-Frankel, "The bad luck of cancer," Science, Jan. 2015, 347: 12.
Cousins et al., "Clarification of plasma from whole human blood using ultrasound," Ultrasonics, 2000, 38: 654-656.
Cousins et al., "Plasma Preparation From Whole Blood Using Ultrasound," Ultrasound in Med. & Biol., 2000, 26: 881-888.
Cousmans et al., "Filter Characteristics Influencing Circulating Tumor Cell Enrichment from Whole Blood," PLOS One, Apr. 2013, 8: e61770.
Cox et al., "Super-Resolution Ultrasound," Nature, 527: 451-452, 2015.
Crosby and Lister, "Hydrodynamic diffusion of sedimenting point particles in a vertical shear flow," Jul. 2013, 1-32.
Croughan, "Hydrodynamic Effects on Animal Cells in Microcarrier Bioreactors," Jun. 1988, 240 pages.
Crowley, "Using Sound Waves for cGMP Manufacturing of a Fusion Protein with Mammalian Cells," BioProcess International, Mar. 2004, 2(3):46-50.
Dalecki and Hocking, "Ultrasound Technologies for Biomaterials Fabrication and Imaging," Annals of Biomedical Engineering, 2014, 15 pages.
Dalm et al., "Effect of Feed and Bleed Rate on Hybridoma Cells in an Acoustic Perfusion Bioreactor: Part I. Cell Density, Viability, and Cell-Cycle Distribution," Biotechnology and Bioengineering, Dec. 5, 2004, 88(5):547-557.
Dalm et al., "Stable Hybridoma Cultivation in a Pilot-Scale Acoustic Perfusion System: Long-Term Process Performance and Effect of Recirculation Rate," Biotechnology and Bioengineering, Sep. 30, 2005, 91(7):894-900.
Dalm, "Determining Viability in Perfusion Bioreactors," Genetic Engineering News, Sep. 15, 2003, 23(16):60, 2 pages.
Dalm, "Acoustic Perfusion Processes for Hybridoma Cultures: Viability, cell cycle and metabolic analysis," PhD thesis, Wageningen University with summary in Dutch, 2007, 160 pages.
Danielli et al., "Nonlinear Photoacoustic Spectroscopy of Hemoglobin," Applied Physics Letters, 160, 203701-1-203701-5, 2015.
D'Avino et al., "Rheology of a dilute suspension of spheres in a viscoelastic fluid under LAOS," J. Computational and Theoretical Nanoscience, Apr. 2010, 7(4):780-786.
Dayton et al., "Application of Ultrasound to Selectively Localize Nanodroplets for Targeted Imaging and Therapy," Mol Imaging, Jul. 2006, 5: 160-174.
De Billy et al., "Measurements of Backscattered Leaky Lamb Waves in Plates," J. Acoust. Soc. Am. 75: 3, 996-1001, 1984.
De Moura da Silva et al., "Impact of autologous blood transfusion on the use of pack of red blood cells in coronary artery bypass grafting surgery," Rev Bras Cir Cardiovasc, 2013, 28: 183-9.
Decave et al., "Peeling Process in Living Cell Movement Under Shear Flow," Physical Review Letters, Sep. 2002, 89: 108101.
Decave et al., "Shear Flow-Induced Detachment Kinetics of Dictyostelium discoideum Cells from Solid Substrate," Biophysical Journal, May 2002, 82: 2383-2395.
Decave et al., "Shear flow-induced motility of Dictyostelium discoideum cells on solid substrate," Journal of Cell Science, 2003, 116: 4331-4343.
Demilly et al., "Kinetics of yeast detachment from controlled stainless steel surfaces," Colloids and Surfaces B: Bioinerfaces, 2006, 51: 71-79.
Denney, "An Ultrasonic Resonator for Determining Speed of Sound and Absorption in Small Volumes of Liquid Media," Graduate College of the University of Illinois at Urbana-Champaign, 1972, 55 pages.
DePalma, Continuity Promotes Bioprocessing Intensity: Moving From Batch Mode to Continuous Mode Concentrates Bioprocessing Wonderfully, Genetic Engineering & Biotechnology News, Apr. 2016, 36: 1-5.
Deshmukh et al., "Acoustic radiation forces at liquid interfaces impact the performance of acoustophoresis," Lab Chip, 2014, 14: 3394-3400.
DiCesare et al., "Development, Qualification, and Application of a Bioreactor Scale-Down Process," BioProcess Technical, Jan. 2016, 14: 18-29.
Dijkink et al., "Controlled cavitation-cell interaction: trans-membrane transport and viability studies," Phys. Med. Biol., 2008, 53: 375-390.
Ding et al., Tunable patterning of microparticles and cells using standing surface acoustic waves, Lab Chip, 2012, 12: 2491-2497.
Ding et al., "Cell separation using tilted-angle standing surface acoustic waves," PNAS, 2014, 12992-12997.
Diogo et al., "Separation Technologies for Stem Cell Bioprocessing," Biotechnology and Bioengineering, Nov. 2012, 109: 2699-2709.
Dodds and Naser, The Effect of Particle Concentration on the Coefficient of Drag of a Spherical Particle, 15th Australasian Fluid Mechanics Conference, The University of Sydney, Syney, Australia, Dec. 2004, 4 pages.
Doinikov, "Acoustic radiation force on a spherical particle in a viscous heat-conducting fluid. I. General formula," J. Acoust. Soc. Am., Feb. 1997, 101: 722-740.
Doinikov, Acoustic radiation force on a spherical particle in a viscous heat-conducting fluid. III. Force on a liquid drop, J. Acoust. Soc. Am., Feb. 1997, 101: 731-740.
Doinikov, "Acoustic radiation pressure on a compressible sphere in a viscous fluid," J. Fluid Mech., 1994, 267: 1-21.
Doinikov, "Acoustic radiation pressure on a rigid sphere in a viscous fluid," Proc. R. Soc. Lond. A, 1994, 447: 447-466.
Doinikov, Acoustic radiation force on a spherical particle in a viscous heat-conducting fluid. II. Force on a rigid sphere, J. Acoust. Soc. Am., Feb. 1997, 101: 722-730.
Doyle et al., "Simulation of elastic wave scattering in cells and tissues at the microscopic level," J. Acoust. Soc. Am., Mar. 2009, 125: 1751-1767.
Doyle, "Computational Scattering Models for Elastic and Electromagnetic Waves in Particulate Media," Utah State University, Logan, Utah, 2004, 227 pages.
Doyle, "Iterative simulation of elastic wave scattering in arbitrary dispersions of spherical particles," J. Acoust. Soc. Am., May 2006, 119: 2599-2610.
Dressler, "Inertial theories for dilute viscoelastic polymer blends with a volume preserving microstructure," Journal of Non-Newtonian Fluid Mechanics, 2012, 173-174: 40-48.
Dressler, "Shear flow properties of polymer blend models with and without droplet inertia," Journal of Non-Newtonian Fluid Mechanics, 2013, 200: 147-164.
Drugs and the Pharmaceutical Sciences: Filtration and Purification in the Biopharmaceutical Industry, 2nd ed., 2008, 816 pages.
Drugs and the Pharmaceutical Sciences: Pharmaceutical Process Validation, 3rd ed., revised and expanded, 2003, 883 pages.
Dubrovskii et al., "Mechanism of Erythrocyte Aggregation Enhancement by Ultrasonic Field," Acoustical Physics, 2004, 50: 184-192.
Dukhin and Goetz, Emulsions and Emulsion Stability, Chapter 9: Ultrasound for Characterizing Emulsions and Microemulsions, 43 pages, 2006.

(56) References Cited

OTHER PUBLICATIONS

Dukhin et al., "Ultrasonic characterization of proteins and blood cells," Colliods and Surfaces B, 2006, 53: 121-126.
Dukhin et al., "Use of Ultrasound for Characterizing Dairy Products," J. Dairy Sci., 2005, 88: JDS4463 (15 pages).
Edwards et al., "Modelling Condensation and the Initiation of Chondrogenesis in Chick Wing Bud Medenchymal Cells Levitated in an Ultrasound Trap," European Cells and Materials, 2010, 19: 1-12.
Eggers and Funck, "Ultrasonic Relaxation Spectroscopy in Liquids," Natuwissenschaften, 1976, 63: 280-285.
El Andaloussi et al., "Extracellular vesicles: biology and emerging therapeutic opportunities," Nature Reviews, May 2013, 12: 347-357.
Eldalil, "Improving the performance of solar still using vibratory harmonic effect," Desalination, 2010, 251: 3-11.
Embleton, "Mean Force on a Sphere in a Spherical Sound Field. I. (Theoretical)," The Journal of the Acoustical Society of America, Jan. 1954, 26: 40-45.
Embleton, "Mean Force on a Spherein a Spherical Sound Field. I I. (Experimental)," The Journal of the Acoustical Society of America, Jan. 1954, 26: 46-50.
Environmental News, "Water Uses by Industry Revealed," 1 page, 2010.
Errico et al., "Ultrafast Ultrasound Localization Microscopy for Deep Super-Resolution Vascular Imaging," Nature, 527: 499-507, 2015.
Eyjolfsson et al., "Characterization of Lipid Particles in Shed Mediastinal Blood," Ann.Thorac Surg, 2008, 85: 978-81.
Falou et al., "A study of high frequency ultrasound scattering from non-nucleated biological specimens," J. Acoust. Soc. Am., Nov. 2008, 124: EL278-EL283.
Farid, "UCL 'Decisional Tools' for the design of cost-effective and robust bioprocesses," presented at the Workshop: Vaccine process development—better tools for better vaccines, London, UK, Nov. 5, 2014, 45 pages.
Farokhzad, "Platelet mimicry," Nature, Oct. 2015, 526: 47-48.
Felo et al., "Process Cost and Facility Considerations in the Selection of Primary Cell Culture Clarification Technology," Biotechnol. Prog., 2013, 29: 1239-1245.
Fenton, Is One of the E's in IEEE for Environmental?, The Electrochemical Society Interface, 1998, 1-3.
FFF 2007: 13th International Sympiosium on Field-and Flow-based Separation, Jun. 2007, 92 pages.
Fisher and Miles, "Modeling the acoustic radiation force in microfluidic chambers (L)," J. Acoust. Soc. Am., Apr. 2008, 123: 1862-1865.
Fluid Particle Interactions Basics Presentation, retrieved on Feb. 17, 2017, URL <https://www2.msm.ctw.utwente.nl/sluding/TEACHING/ParticleTechnology/vdHoef_FluidParticleInteractions.pdf>, 37 pages.
Foller and Tobias, "The Anodic Evolution of Ozone," J. Electrochem. Soc., Mar. 1982, 129: 506-515.
Foller and Tobias, "The Mechanism of the Disintegration of Lead Dioxide Anodes under Conditions of Ozone Evolution in Strong Acid Electrolytes," J. Eletrochem. Soc., Mar. 1982, 129: 567-570.
Foods Lipids, 2nd ed., revised and expanded, 2002, 1014 pages.
Frank et al., "Separation of Suspended Particles by use of the Inclined Resonator Concept," International 93 Conference Proceedings, 1993, 519-521.
Franke et al., "Surface acoustic wave actuated cell sorting (SAWACS)," Lab on a Chip, 2010, 10: 789-794.
Frankel, "Acoustic Resonator Aerosol Particle Separation," Jun. 2002, 6 pages.
Friend and Yeo, "Microscale acoustofluidics: Microfluidics driven via acoustics and ultrasonics," Reviews of Modern Physics, Apr.-Jun. 2011, 83: 647-704.
Gaaseidnes and Turbeville, "Separation of oil and water in oil spill recovery operations," Pure Appl. Chem., 1999, 71: 95-101.

Gallego-Juarez et al., "Development of Industrial Models of High-Power Stepped-Plate Sonic and Ultrasonic Transducers for Use in Fluids," IEEE Ultrasonics Symposium, 2001, 571-578.
Gardner et al., "Using Acoustics to Study Stimulate the Coalescence of Oil Drops Surrounded by Water," Journal of Colloid and Interface Science, 159: 226-237, 1993.
Garrivier et al, "Peeling model for cell detachment," Eur. Phys. J. E., 2002, 8: 79-97.
Garvin et al., "Spatial patterning of endothelial cells and vascular network formation using ultrasound standing wave fields," J. Acoust. Soc. Am., Aug. 2013, 134: 1483-1490.
Geer et al., "Effect of Colostrum on Gravity Separation of Milk Somatic Cells in Skim Milk," Journal of Dairy Science, 97: 2, 687-693, 2014.
Gherardini et al., "A New Immobilisation Method to Arrange Particles in a Gel Matrix by Ultrasound Standing Waves," Ultrasound in Med. & Biol., 2005, 31: 261-272.
Ghoshal et al., "Temperature dependent ultrasonic characterization of biological media," J. Accoust. Soc. Am., Oct. 2011, 2203-2211.
Giddings et al., "Flow Field-Flow Fractionation: New Method for Separating, Purifying, and Characterizing the Diffusivity of Viruses," Journal of Virology, Jan. 1977, 21: 131-138.
Gilham et al., "CAR-T cells and solid tumors: tuning T cells to challenge an inveterate foe," Trends in Molecular Medicine, Jul. 2012, 18: 377-384.
Gimble et al.,"Adipose-Derived Stem Cells for Regenerative Medicine," Circulation Research, May 2007, 100: 1249-1260.
Godin et al., "Measuring the mass, density, and size of particles and cells using a suspended microchannel resonator," Applied Physics Letters, 2007, 91: 123121.
Gonzalez, "On the hydrodynamic diffusion of rigid particles," SIAM J. Appl. Math, 2010, 70(7): 2627-2651.
Gorenflo et al., "Characterization and Optimization of Acoustic Filter Performance by Experimental Design Methodology," Biotechnology and Bioengineering, Jun. 20, 2005, 90(6):746-753.
Gorenflo et al., "Scale-Up and Optimization of an Acoustic Filter for 200 L/day Perfusion of a CHO Cell Culture," Biotechnology and Bioengineering, Nov. 20, 2002, 80(4):438-444.
Gor'kov, "On the Forces Acting on a Small Particle in an Acoustical Field in an Ideal Fluid," Physics, Mar. 1962, 6: 773-775.
Gossett et al., "Label-free cell separation and sorting in microfluidic systems," Anal Bioanal Chem, 2010, 397: 3249-3267.
Gotsi et al., "Electrochemical oxidation of olive oil mill wastewaters," Water Research, 2005, 39: 4177-4187.
Grant, "Creating a Cell Therapy Manufacturing System," Invetech, Jan. 2016, 34 pages.
Green et al., "Controlling non-inertial cavitation microstreaming for applications in biomedical research," AIP Conference Proceedings, 2012, 4 pages.
Green, "Micro-scale Fluid Flows: The Application of Acoustic Streaming to Biomedical Research," Engineering Science unit, University of Southampton, Jul. 2013, 274 pages.
Greenleaf et al., "Artificial Cavitation Nuclei Significanty Enhance Acoustically Induced Cell Transfection," Ultrasound in Med. & Biol., 1998, 24: 587-595.
Gregory et al., "Chapter 7: Sedimentation and Flotation", Water Quality and Treatment: A Handbook of Community Water Supplies, 5th Ed., © 1999, 87 pages.
Grinenko et al., "Acoustic radiation force analysis using finite difference time domain method," J. Acoust. Soc. Am., May 2012, 131: 3664-3670.
Grinenko et al., "Efficient counter-propagating wave acoustic micro-particle manipulation," Applied Physics Letter, 2012, 101: 233501.
Groschl, "Ultrasonic Separatiom of Suspended Particles—Pat III: Application in Biotechnology," Acta Acustica united with Acustica, 1998, 815-822.
Groschl, "Ultrasonic Separation of Suspended Particles—Part I: Fundamentals," Acta Acustica united with Acustica, 1998, 84: 432-447.
Groschl, "Ultrasonic Separation of Suspended Particles—Part II: Design and Operation of Separation Devices," Acta Acustica united with Acustica, 1998, 84: 632-642.

(56) References Cited

OTHER PUBLICATIONS

Grossner et al., "Transport Analysis and Model for the Performance of an Ultrasonically Enhanced Filtration Process," Chemical Engineering Science, 2005, 60: 3233-3238.
Grover et al., "Measuring single-cell density," PNAS, Jul. 2011, 108: 10992-10996.
Grover et al., "Supporting Information," PNAS, 2011, 4 pages.
Gu et al., "Understanding Surface Adhesion in Nature: A Peeling Model," Adv. Sci., 2016, 3: 1500327.
Guazzelli and Hinch, "Fluctuations and Instability in Sedimentation," Annu. Rev. Fluid Mech., 2011, 43: 97-116.
Gumerov and Duraiswami, "Computation of scattering from clusters of spheres using the fast multipole method," J. Acoust. Soc. Am., 117: 1744-1761.
Gupta and Feke, "Filtration of Particulate Suspensions in Acoustically Driven Porous Media," AIChE Journal, May 1998, 44: 1005-1014.
Haake, "Manipulation of Small Particles with Ultrasound," A dissertation submitted to the Swiss Federeal Institute of Technology Zurich, 2004, 149 pages.
Haberman et al., "Acoustic Metamaterials," Physics Today, 43-48, 2016.
Hakala et al., "Massive blood transfusion exceeding 50 units of plasma poor red cells or whole blood: the survival rate and the occurrence of leukopenia and acidosis," Injury, Int. J. Care Injured, 1999, 30: 619-622.
Hamilton et al., "Acoustic streaming generated by standing waves in two-dimensional channels of arbitrary width," J. Acoust. Soc. Am., Jan. 2003, 113(1):153-160.
Hamilton et al., "Thermal effects on acoustic streaming in standing waves," J. Acoust. Soc. Am., Dec. 2003, 114 (6, part 1):3092-3101.
Hamilton et al., "Linear and nonlinear frequency shifts in acoustical resonators with varying cross sections," J. Acoust. Soc. Am. 110:1, 109-119, 2001.
Hamine et al., "Modeling Ultrasonic Attenuation Coefficient and Comparative Study with the Principle Theoretical Models of Biphasic Suspensions," IOSR Journal of Applied Physics, 4:5, 18-29, 2013.
Hammarstrom et al., "Frequency tracking in acoustic trapping for improved performance stability and system surveillance," Lab on Chip, 2013, 1-13.
Hammarstrom et al., Non-contact acoustic cell trapping in disposable glass capillaries10: 2251-2257.
Hammarstrom et al., "Seed particle-enabled acoustic trapping of bacteria and nanoparticles in continuous flow systems," Lab Chip, 2012, 12: 4296-4304.
Hammarstrom, "Acoustic Trapping in Biomedical Research," Lund University, Department of Biomedical Engineering, May 2014, 70 pages.
Han et al., "Ultrasonic backscatter coefficient quantitative estimates from high-concentration Chinese hamster ovary cell pellet biophantoms," J. Acoust. Soc. Am., Dec. 2011, 4139-4147.
Harihsa et al., "Arsenic removal from drinking water using thin film composite nanofiltration membrane," Desalination, 2010, 252: 75-80.
Harris et al., "A Lateral Mode Flow-through PMMA Ultrasonic Separator," International Journal of Applied Biomedical Engineering, 5:1, 8 pages, 2012.
Hartono et al., "On-chip measurements of cell compressibility via acoustic radiation," Lab Chip, 2011, 11: 4072-4080.
Hatch et al., "Tag-Free Microfluidic Separation of Cells Against Multiple Markers," Anal. Chem., May 2012, 84: 4618-4621.
Hawkes and Coakley, "A continuous flow ultrasonic cell-filtering method," Enzyme and Microbial Technology, 1996, 19: 57-62.
Hawkes et al., "A laminar flow expansion chamber facilitating downstream manipulation of particles concentrated using an ultrasonic standing wave," Ultrasonics, 1998, 36: 901-903.
Hawkes et al., "Continuous cell washing and mixing driven by an ultrasound standing wave within a microfluidic channel," Lab Chip, 2004, 4: 446-452.
Hawkes et al., "Filtration of bacteria and yeast by ultrasound-enhanced sedimentation," Journal of Applied Microbiology, 1997, 82: 39-47.
Hawkes et al., "Single half-wavelength ultrasonic particle filter: Predictions of the transfer matrix multilayer resonator model and experimental filtration results," J. Acoust. Soc. Am., Mar. 2002, 111: 1259-1266.
Hawkes et al., "Ultrasonic deposition of cells on a surface," Biosensors and Bioelectronics, 2004, 19: 1021-1028.
Hawkes et al., "Ultrasonic manipulation of particles in microgravity," J. Phys.D: Appl. Phys., 1998, 1673-1680.
Hawley, "Ultrasonic Absorption in Aqueous Suspension of Small Elastic Particles," Graduate College of the University of Illinios, 1967, 137 pages.
High Efficiency Liquid/Liquid Hydrocyclone, Siemens Water Technologies, 2009, 2 pages.
Hill and Harris, Chapter 9: Ultrasonic Particle Manipulation. In Microfluidic technologies for miniaturized analysis systems, 2007, 357-293.
Hollyman et al., "Manufacturing Validation of Biologically Functional T Cells Targeted to CD19 Antigen for Autologous Adoptive Cell Therapy," J Immunother, 2009, 32: 169-180.
Hsu et al., "Seawater desalination by direct contact membrane distillation," Desalination, 2002, 143: 279-287.
Hu et al., "Nanoparticle biointerfacing by platelet membrane cloaking," Nature, Oct. 2015, 526: 118-121.
Hultstrom et al., Proliferation and Viability of Adherent Cells Manipulated by Standing-Wave Utrasound in a Microfluidic Chip, Ultrasound in Med. & Biol., 2007, 33: 145-151.
Hydrocyclone, V& T Group, available online on or before Feb. 16, 2017, URL<http://www.v-tfiltergroup.com/VTFiltergroup/download/196145Cycloon_EN.pdf>, 4 pages.
Im et al., "Label-free detection and molecular profiling of exosomes with a nano-plasmonic sensor," Nature Biotechnology, May 2014, 490.
innovativeultrasonics.com' [online] "Ultrasonic Innovations in the Food Industry: From the Laboratory to Commercial Production," Oct. 2007, [retrieved on Nov. 6, 2013]. Retrieved from the internet: URL <http://www.innovativeultmsonics.com/publications/Ultrasonic-Innovations-in-the-Food-Industry-From-the-Laboratory-to-Commercial-Production/>. 10 pages.
Iranmanesh et al., "Tunable-angle wedge transducer for improved acoustophoretic control in a microfluidic chip," J. Micromech. Microeng., 2013, 23: 105002.
Jack et al., "Influence of the acousto-optic effect on laser Doppler anemometry signals," Review of Scientific Instruments, 1998, 69: 4074-4081.
Jayanthi et al., "Influence of Post Curing Conditions on the Mechanical Properties of Stereolithographic Photopolymers," University of Texas, 1995, URL: https://sffsymposium.engr.utexas.edu/Manuscripts/1995/1995-14-Jayanthi.pdf, 107-117.
Jensen and Bruus, Proceedings of Meetings on Acoustics, ICA 2013 Montreal, 2013, 19: 045001.
Jeong et al., High-pressure acoustic properties of glycerol studied by Brillouin spectroscopy, Physica B, 2015, 478: 27-30.
Jewell et al., "A prospective randomised comparison of cardiotomy suction and cell saver for recycling shed blood during cardiac surgery," European Journal of Cardio-thoracic Surgery, 2003, 23: 633-636.
Jia et al., "Building the isotropic acoustic potential well with strong constraint boundary to improve the stability of ultrasonic transportation," Journal of Applied Science, 2013, 113: 064903.
Johansson et al., "Cavitation and non-cavitation regime for large-scale ultrasonic standing wave particle separation systems—In situ gentle cavitation threshold determination and free radical related oxidation," Ultrasonics Sonochemistry, 2016, 28: 346-356.
Johansson et al., "Effective Mixing of Laminar Flows at a Density Interface by an Integrated Ultrasonic Transducer," Twelfth International Conference on Miniaturized Systems for Chemistry and Life Sciences, San Diego, California, Oct. 2008, 80-82.
Johansson et al., "Temperature and trapping characterization of an acoustic trap with miniaturized integrated transducers—towards in-trap temperature regulation," Ultrasonics, 2013, 53: 1020-1032.

(56) References Cited

OTHER PUBLICATIONS

Johansson et al., "Temperature control and resonance mode analysis of an acoustic trap for µTAS," 2009, 1-11.
Johansson, "Accoustic Manipulation of Particles and Fluids in Microfluidic Systems," Digital Comprehensive Summaries of Uppsala Dissertations from the Faculty of Science and Technology 641, 2009, 82 pages.
Johnsen et al., "A comprehensive overview of exosomes as drug delivery vehicles—Endogenous nanocarriers for targeted cancer therapy," Biochima et Biophysica Acta, 2014, 1846: 75-87.
Johnson, "Using Vibrating Membranes to Treat Oily Wastewater," New Logic Research, available on or before Sep. 16, 2003, retrieved from URL <http://www.vsep.com/pdf/OilyWastewater.pdf>, 7 pages.
Juliano et al., "Creaming Enhancement in a Liter Scale Ultrasonic Reactor as Selected Transducer Configurations and Frequencies," Ultrasonics Sonochemistry, 20: 52-62, 2013.
Junge et al., "Cell Detachment Method Using Shock-Wave-Induced Cavitation," Ultrasound in Med. & Biol., 2003, 29: 1769-1776.
Juniel, "Practical Application of Produced Water Treating Technology for Land-Based Injection Operations," May 2003, 21 pages.
Jurgen Bereiter-Hahn and Christopher Blase, Ultrasonic Nondestructive Evaluation: Engineering and Biological Material, Chapter 12: Ultrasonic Characterization of Biological Cells, 35 pages, 2004.
Kaiser et al., "Towards a commercial process for the manufacture of genetically modified T cells for therapy," Cancer Gene Therapy, 2015, 22: 72-78.
Kang et al., "An extracorporeal blood-cleansing device for sepsis therapy," Nature Medicine, 2014, 20: 1211-1216.
Karn et al., "Nano Particles Without Macroproblems," IEEE Spectrum, 55-58, 2007.
Karpul et al., "Limiting factors in acoustic separation of carbon particles in air," J. Acoust. Soc. Am., Apr. 2010, 2153-2158.
Keesman et al., "Ultrasound Standing-wave Bio-Reactor design and testing," 2013 Joint UFFC, EFTF and PFM Symposium, 2013, 1331-1332.
Kersaudy-Kerhoas and Sollier, "Micro-scale blood plasma separation: from acoustophoresis to egg-beaters," Lab Chip, 2013, 13: 3323-3346.
Kirouac and Zandstra, "The Systematic Production of Cells for Cell Therapies," Cell Stem Cell, Oct. 2008, 3: 370-381.
Klara, "Final Report of the Coalescing Tubes Test for Oil/Water Separators (OWSs)," Sep. 1998, 60 pages.
Knoop and Fritsching, "Dynamic forces on agglomerated particles caused by high-intensity ultrasound," Ultrasonics, 2013, 1-7.
Knoop and Fritsching, "Simulation and verification of forces on particles in ultrasound agitated gases," Piko Workshop, 2012, 25 pages.
Kotz et al., "Electrochemical waste water treatment using high overvoltage anodes. Part I: Physical and electrochemical properties of SnO2 anodes," Journal of Applied Electrochemistry, 1991, 21: 14-20.
Kristensen, "Theory and application of ultrasound diagnostics of aqueous solutions," Department of Micro- and Nanotechnology, Technical University of Denmark, Jul. 2010, 122 pages.
Kuang et al., "Resonance Tracking and Vibration Stabilization for High Power Ultrasonic Transducers," Ultrasonics, 54: 187-194, 2013.
Kumar et al., "Fractionation of Cell Mixtures Using Acoustic and Laminar Flow Fields," Biotechnology and Bioengineering, Jan. 2005, 89: 130-137.
Kuznetsova et al., "Cavitation bubble-driven cell and particle behavior in an ultrasound standing wave," J. Acoust. Soc. Am., Jan. 2005, 117: 104-112.
Kwiatkowski and Marston, "Resonator frequency shift due to ultrasonically induced microparticle migration in an aqueous suspension: Observations and model for the maximum frequency shift," J. Acoust. Soc. Am., Jun. 1998, 103: 3290-3300.
Kyllonen et al., "Membrane filtration enhanced by ultrasound: a review," Desalination, 2005, 181: 319-335.
Kytomaa, "Theory of sound propagation in suspensions: a guide to size and concentration characterization," Powder Technology, 1995, 82: 115-121.
Lackner et al., "Detachment Kinetics of Eukaryote Cells From Biocompatible PVD Coatings," Society of Vacuum Coaters, 50th Annual Technical Conference Proceedings, 2007, 74-77.
Laurell et al., "Chip integrated strategies for acoustic separation and manipulation of cells and particles," Chem. Soc. Rev., 2007, 36: 492-506.
Law, "Droplet Collision in Liquid Propellant Combustion," 1997, 28 pages.
Lee et al., "Acoustic Purification of Extracellular Microvesicles," ACS Nano, Mar. 2015, 9: 2321-2327.
Lee et al., "Outer acoustic streaming," J. Acoust. Soc. Am., Nov. 1990, 88(5):2367-2375.
Leibacher et al., "Impedance matched channel walls in acoustofluidic systems," Lab Chip, 2014, 14: 463-470.
Leighton et al., "Primary Bjerknes forces," Eur. J. Phys., 1990, 11: 47-50.
Lenshof and Laurell, "Emerging Clinical Applications of Microchip-Based Acoustophoresis," JALA, Dec. 2011, 443-449.
Lenshof et al., "Efficient Purification of CD41 Lymphocytes from Peripheral Blood Progenitor Cell Products Using Affinity Bead Acoustophoresis," Cytometry Part A., 2014, 85A: 933-941.
Leong et al., "Design Parameters for the Separation of Fat from Natural Whole Milk in an Ultrasonic Litre-Scale Vessel," Ultrasonics Sonochemsitry, 10 pages, 2014.
Leong et al., "Ultrasonic Separation of Particulate Fluids in Small and Large Scale Systems: A Review," Industrial and Engineering Chemistry Research, 52: 16555-16576, 2013.
Lesko, Chemical Effects of Acoustic Cavitation, California Institute of Technology, 2004, 198 pages.
Lewis et al., "Cost-effective broad-band electrical impedance spectroscopy measurement circuit and signal analysis for piezo-materials and ultrasound transducers," Meas Sci Technol., Oct. 2008, 19: 105102.
Li and You, "Simulation of Acoustic Energy Harvesting Using Piezoelectric Plates in a Quarter-wavelength Straight-tube Resonator," Excerpt from the Proceedings of the 2012 COMSOL Conference in Boston, 2012, 16 pages.
Li and You, "Simulation of Acoustic Energy Harvesting Using Piezoelectric Plates in a Quarter-wavelength Straight-tube Resonator," Excerpt from the Proceedings of the 2012 COMSOL Conference in Boston, 2012, 7 pages.
Li et al., "Application of an acoustofluidic perfusion bioreactor for cartilage tissue engineering," Lab Chip, 2014, 14: 4475-4485.
Li et al., "Direct numerical simulation of a particle-laden low Reynolds number turbulent round jet," International Journal of Multiphase Flow, 2011, 37: 539-554.
Li et al., "Probing circulating tumor cells in microfluidics," Lab on a Chip, 2013, 13: 602-609.
Liang., "The Magnitude of Basset Forces in Unsteady Multiphase Flow Computations," Journal of Fluids Engineering, 114: 417-419, Sep. 1992.
Lim and Hoon, "Circulating tumor cells: Cancer's deadly couriers," Physics Today, Feb. 2014, 67: 26-29.
Lim, Jr. et al., "Platelet Response and Coagulation Changes Following Massive Blood Replacement," The Journal of Trauma, 13: 577-582.
Lin and Peng, "Treatment of Textile Wastewater by Electrochemical Method," Wat. Res., 1994, 28: 2747-282.
Lin et al., "Surface acoustic wave (SAW) acoustophoresis: now and beyond," Lab Chip, 2012, 12: 2766-2770.
Lipsitz et al., "Quality cell therapy manufacturing by design," Nature Biotechnology, Apr. 2016, 34: 393-400.
Liquid/Liquid Hydrocyclones: Oilspin AV Hydrocyclone, NATCOGROUP, Jun. 2002, A-1-A-2.
Liu et al., "Effects of fluid medium flow and spatial temperature variation on acoustophoretic motion of microparticles in microfluidic channels," J. Acoust. Soc. Am., Jan. 2016, 139: 332-349.
Liu et al., "Cell separation and transporation between two miscible fluid streams using ultrasound," Biomicrofluidics, 2012, 6: 012802.

(56) References Cited

OTHER PUBLICATIONS

Liu et al., "Proceedings of Meetings on Acoustics," ICA 2013 Montreal, 2013, 19: 1-5.
Lloyd and Berry, "Wave propagation through an assembly of spheres IV. Relations between different multiple scattering theories," Proc. Phys. Soc., 1967, 91: 678-688.
Lochab et al., "Acoustic Behavior of Plastics for Medical Applications," Indian Journal of Pure and Applied Physics, 42: 595-599, 2004.
Longsine-Parker et al., "Microfluidic electro-sonoporation: a multimodal cell poration methodology through simultaneous application of electric field and ultrasonic wave," Lab Chip, 2013, 13: 2144-2152.
Lopez et al., "Enhanced Acoustic Separation of Oil-Water Emulsion in Resonant Cavities," The Open Acoustics Journal, 1: 66-71, 2008.
Lu and Zhong, "Ultrasound-induced cell detachment and gene transfection in adherent cells," Accoustical Society of America, Jul. 2005, 195-200.
Malers, "Fundamentals of bubble transportation in an ultrasonically assisted separation project," Case Western Reserve University School of Graduate Studies, May 2008, 174 pages.
Mandralis and Feke, "Fractionation of Suspensions Using Synchronized Ultrasonic and Flow Fields," AIChE Journal, Feb. 1993, 39: 197-206.
Manneberg et al., "Spatial confinement of ultrasonic force fields in microfluidic channels," Ultrasonics, 2009, 49: 112-119.
Manneberg et al., "Wedge Transducer Design for Two-Dimensional Ultrasonic Manipulation in a Microfluidic Chip," J. Micromech. Microeng. 18: 10 pages, 2008.
Mannenberg, "Multidimensional Ultrasonic Standing Wave Manipulation in Microfluidic Chips," Department of Applied Physics, Royal Institute of Technology, 2009, 95 pages.
Marchetti, "Frictionless fluids from bacterial teamwork," Nature, Sep. 2015, 525: 37-39.
Marston and Apfel, "Acoustically Forced Shape Oscillation of Hydrocarbon Drops Levitated in Water," Journal of Colloid and Interface Science, Feb. 1979, 68: 280-286.
Marston and Thiessen, "Manipulation of Fluid Objects with Acoustic Radiation Pressure," Ann. N.Y. Acad. Sci., 2004, 1027: 414-434.
Masudo and Okada, "Microparticle Separation with an Acoustic-gravity Field Controlled by Phase-shift Operation," Analytical Sciences, Apr. 2007, 23: 385-387.
Masudo and Okada, "Particle Characterization and Separation by a Coupled Acoustic-Gravity Field," Anal. Chem., 2001, 73: 3467-3471 (abstract only).
Mathioulakis et al., "Desalination by using alternative energy: Review and state-of-the-art," Desalination, 2007, 203: 346-365.
Matula and Chen, "Microbubbles as Ultrasound Contrast Agents," Acoustics Today, Jan. 2013, 9: 14-20.
Mazur and Van Saarloos, "Many-Sphere Hydrodynamic Interactions and Mobilities in a Suspension," Physica, 1982, 115A: 21-57.
McClements, Comparison of multiple scattering theories with experimental measurements in emulsions, J. Acoust. Soc. Am., Feb. 1992, 91: 849-853.
McClements., "The Use of Ultrasonics for Characterising Fats and Emulsions," Procter Department of Food Science, University of Leeds, LS29JT, 239 pages, Nov. 1988.
McDonnell et al., "Motility induced changes in viscosity of suspensions of swimming microbes in extensional flows," Soft Matter, 2015, 11: 4658-4668.
McHugh et al., "Characterisation of Epoxy Materials Used in the Development of Ultrasonic Arrays," 8 pages.
McIntyre, "On the 'wave momentum' myth," J. Fluid Mech., 1981, 106: 331-347.
Mehigh, "Lysis of *E.coli* for the Purification of Soluble Recombinant Proteins using CelLytic-BTM and CelLytic-BTM II" Molecular Biology, Sigma Origins 3, 2001, 16-17.
Melde et al., "Holograms for Acoustics," Nature, 537: 518-532, 2016.

Menssen et al., "Rapid dissociation of adherent human tumor cells by ultrasound," Journal of Immunological Methods, 1987, 104: 1-6.
Miller and Battaglia, "The Relevance of Cell Size on Ultrasound-Induced Hemolysis in Mouse and Human Blood in Vitro," Ultrasound in Med. & Biol., 2003, 29: 1479-1485.
Miller and Dou, "Induction of Apoptosis in Sonoporation and Ultrasonic Gene Transfer," Ultrasound Med Biol., Jan. 2009, 35: 144-154.
Mishra et al., "Deformation of red blood cells using acoustic radiation forces," Biomicrofluidics, 2014, 8: 034109.
Mitri et al., "Theoretical calculation of the acoustic radiation force acting on elastic and viscoelastic cylinders placed in a plane standing or quasistanding wave field," Eur. Phys. J. B, 2005, 44: 71-78.
Mitri, "Axial acoustic radiation force on rigid oblate and prolate spheroids in Bessel vortex beams of progressive, standing and quasi-standing waves," Ultrasonics, 2017, 12 pages.
Moller et al., "Schlieren visualization of ultrasonic standing waves in mm-sized chambers for ultrasonic particle manipulation," Journal of Nanobiotechnology, 2013, 11: 21.
Moosai et al., "Oily Wastewater Cleanup by Gas Flotation," West Indian Journal of Engineering, 25: 1, 25-41, Jul. 2002.
Morais et al., "Turbidimetric and Nephelometric Flow Analysis: Concepts and Applications," Spectroscopy Letters, 39: 547-579, 2006.
Muller and Bruus, "Numerical study of thermoviscous effects in ultrasound-induced acoustic streaming in microchannels," Physical Review E, 2014, 90: 043016.
Muller and Bruus, "Theoretical study of time-dependent, ultrasound-induced acoustic streaming in microchannels," Physical Review E, 2015, 92: 063018.
Muller et al., "A numerical study of microparticle acoustophoresis driven by acoustic radiation forces and streaming-induced drag forces," Lab Chip, 12: 4617-4627.
Muller et al., "COMSOL Analysis of Acoustic Streaming and Microparticle Acoustophoresis," Excerpt from the Proceedings of the 2012 COMSOL Conference in Milan, 2012, 4 pages.
Muller et al., "COMSOL analysis of acoustic streaming and microparticle acoustophoresis," COMSOL Conference, Milano Italy, Oct. 2012, 18 pages.
Muller et al., "Ultrasound-induced acoustophoretic motion of microparticles in three dimensions," Physical Review E, 2013, 88: 023006.
Murdoch et al., Oil/Water Separator Test and Evaluation, Nov. 1995, 278 pages.
Murphy et al., "Direct Electrochemical Oxidation of Organics for Wastewater Treatment," Wat. Res., 1992, 26: 443-451.
Murray et al., "Quantitative Magnetic Separation of Particles and Cells Using Gradient Magnetic Ratcheting," Small, 2016, 1891-1899.
Nasiri et al., "Flocculation and Separation of Oil Droplets in Ultrasonic Standing Wave Field," Separation Science and Technology, 47: 1985-1990, 2012.
Nature Publishing Group., "A Fresh Approach to Water," Nature, 452: 7185, 1 page, 2008.
Nature Publishing Group., "A Long Dry Summer," Nature, 452: 4 pages, 2008.
Nature Publishing Group., "More Crop Per Drop," Nature, 452: 5 pages, 2008.
Nature Publishing Group., "Water Under Pressure," Nature, 452: 1 page, 2008.
Nawaz et al., "The emerging role of extracellular vesicles as biomarkers for urogenital cancers," Nature Reviews, Dec. 2014, 11: 688-701.
Neild et al., "A micro-particle positioning technique combining an ultrasonic manipulator and a microgripper," J. Micromech. Microeng., 2006, 16: 1562-1570.
Neild et al., "Design, modeling and characterization of microfluidic devices for ultrasonic manipulation," Sensors and Actuators B, 2007, 121: 452-461.
Neild., "Motion Controlled by Sound," Nature, 537: 493-494, 2016.
Nicolas Ratkovich., "Understanding Hydrodynamics in Membrane Bioreactor Systems for Wastewater Treatment: Two-Phase Empiri-

(56) References Cited

OTHER PUBLICATIONS cal and Numerical Modeling and Experimental Validation," Faculty of Bioscience Engineering, Ghent University, May 3, 2010, Ghent—Belgium.

Nilsson et al., "Acoustic control of suspended particles in micro fluidic chips," Lab Chip, 2004, 4: 131-135.

Nilsson et al., "Acoustic Trapping of Cells in a Microfluidic Format," 9th International Conference on Miniaturized Systems for Chemistry and Life Sciences, 2005, 3 pages.

Nordin and Laurell, "Hundred-Fold Volume Concentration of Cells and particles Using Continuous Flow Multistage acoustophoresis," 16th International Conference on Miniaturized Systems for Chemistry and Life Sciences, Okininawa, Japan, 2012, 512-514.

Nowotny et al., "General one-dimensional treatment of the layered piezoelectric resonator with two electrodes," J. Acoust. Soc. Am., Aug. 1987, 82(2):513-521.

Nuzzo., "Fooling Ourselves," Nature, 526: 182-185, 2015.

Nyborg, "Radiation Pressure on a Small Rigid Sphere," The Journal of the Acoustical Society of America, May 1967, 42: 947-952.

Oberti et al., "Manipulation of micrometer sized particles within a micromachined fluidic device to form two-dimensional patterns using ultrasound," J. Acoust. Soc. Am., Feb. 2007, 121: 778-785.

Ohigashi et al., "Analysis of Frequency Response Characteristics of Polymer Ultrasonic Transducers," Japanese Journal of Applied Physics, 27:3, 354-360, 1988.

Ohl and Wolfram, "Detachment and sonoporation of adherent HeLa-cells by shock wave-induced cavitation," Biochimica and Biophysica Acta, 2003, 1624: 131-138.

Optimal Bioaerosol Sampler, Contract No. DAAD13-03-9-0076, Manning Applied Technology, available online on or before Feb. 20, 2015, retrieved from URL< http://www.appl-tech.com/Briefing_Charts/Bioaerosol.pdf>, 1 page.

Otsuka et al., "Ultrasonic Levitation by Stepped Circular Vibrating Plate," Proceedings of 10th Symposium on Ultrasonic Electronics, Tokyo, 1989, Japanese Journal of Applied Physics, 1990, 29(Supplement 29-1):170-172.

Pamphilon and Szczepiorkowski, "Regulation and accreditation in cellular therapy," Practical Transfusion Medicine, 2009, 409-496.

Panizza and Cerisola, "Olive mill wastewater treatment by anodic oxidation with parallel plate electrodes," Water Research, 2006, 40: 1179-1184.

Parrales et al., "Acoustic characterization of monodisperse lipid-coated microbubbles: Relationship between size and shell viscoelastic properties," J. Acoust. Soc. Am., Sep. 2014, 136: 1077-1084.

Perales and Gonzalez, "On the Forces in Micromanipulation of Particles at Low Frequencies," Ultrasonics Symposium, 2005 IEEE, 2005, 4: 2108-2111.

Petersson et al., "Continuous separation of lipid particles from erythrocytes by means of laminar flow and acoustic standing wave forces," Lab on a Chip, 2005, 5: 20-22.

Petersson et al., "Free Flow Acoustophoresis: Microfluidic-Based Mode of Particle and Cell Separation," Anal. Chem., 2007, 79: 5117-5123.

Petersson et al., "Integrated Acoustic Sample Preparation for Rapid Sepsis Diagnostics," 18th International Conference on Miniaturized Systems for Chemistry and Life Sciences, San Antonio, Texas, Oct. 2014, 294-296.

Pethrick, "The swept frequency acoustic resonant interferometer: measurement of acoustic dispersion parameters in the low megahertz frequency range," Journal of Physics E: Scientific Instruments, 1972, 56: 571-574.

Pinfield, "Acoustic scattering in dispersions: Improvements in the calculation of single particle scattering coefficients," J. Acoust. Soc. Am., Jul. 2007, 122: 205-221.

Pinfield, "Thermo-elastic multiple scattering in random dispersions of spherical scatterers," J. Acoust. Soc. Am., Dec. 2014, 136: 3008-3017.

Pinto et al., "Separation of CHO cells using hydrocyclones," Cytotechnoloy, 2008, 56: 57-67.

Piyasena et al., "Multinode acoustic focusing for parallel flow cytometry," Anal. Chem., Jan. 2012, 1-35.

Placzek et al., "Stem cell bioprocessing: fundamentals and principles," J. R. Soc. Interface, 2009, 6: 209-232.

Plaksin et al., "Intramembrane Cavitation as a Predictive Bio-Piezoelectric Mechanism for Ultrasonic Brain Stimulation," Physical Review, 2014, 4: 011004.

Plebon et al., "Further Advances in Produced Water De-Oiling Utilizing a Technology That Removes and Recovers Dispersed Oil in Produced Water 2 Microns and Larger," Earth (Canada) Corporation, available online on or before Feb. 19, 2006, URL <http://ipec.utulsa.edu/Conf2005/Papers/Plebon_Further_Advances.pdf>, 20 pages.

Prado et al., Viscoelastic Transient of Confined Red Blood Cells, Biophysical Journal, May 2015, 108: 2126-2136.

Prest et al., "Scaling-up ultrasound standing wave enhanced sedimentation filters," Ultrasonics, 2014, 1-11.

Prowse et al., "Commercially available blood storage containers," Vox Sanguinis, 2014, 106: 1-13.

Pui et al., "Batch and Semicontinuous Aggregation and Sedimentation of Hybridoma Cells by Acoustic Resonance Fields," Biotechnol. Prog., Mar. 1, 1995, 11(2):146-152.

Radel, "Influence of biomass, throughput and true electric power input on the separation efficiency of a 60mL acoustic filter," Elektrotechnik and Informationstechnik, Feb. 1, 2009, 126 (1-2):51-57.

Ramirez-Munoz et al., "Hydrodynamic force on interactive spherical particles due to the wake effect," International Journal of Multiphase Flow, 2007, 33: 802-807.

Ran and Saylor, "The directional sensitivity of the acoustic radiation force to particle diameter," J. Acoust. Soc. Am., Jun. 2015, 137: 3288-3298.

Razvi, GENReports: Market & Tech Analysis, "Biofluid Biopsies Deploying Circulating Biomarkers," 2015, 13 pages.

Read et al., "Conditioning out-of-date bank-stored red blood cells using a cell-saver auto-transfusion device: effects on numbers of red cells and quality of suspension fluid," Anaesthesia, 2014, 69: 1206-1213.

Rebound et al., "Shaping acoustic fields as a toolset for microfluidic manipulations in diagnostic technologies," PNAS, Sep. 2012, 109: 15162-15167.

Ren et al., "Isolation, expansion, and differentiation of goat adipose-derived stem cells," Veterinary Science, 2012, 93: 404-411.

Rezeli et al., "Comparative Proteomic Analysis of Extracellular Vesicles Isolated by Acoustic Trapping or Differential Centrifugation," Anal. Chem., 2016, 88: 8577-8586.

Rios, "Efforts Toward the Harmonization of Single-Use Standards," BioProcess International, Apr. 2014, 12: 4-11.

Rose et al., "Hybridoma culture using New Brunswick™ CelliGen® 310 with Packed-bed Fibra-Cel® Basket Impeller," Application Note, Jul. 2013, 1-3.

Roy, "Quantitative Particle Characterization by Scattered Ultrasound," Graduate School Yale University, 1987, 148 pages.

Rushton et al., "Solid-Liquid Filtration and Separation Technology," 1996, 551 pages.

Ryll et al., "Performance of Small-Scale CHO Perfusion Cultures Using an Acoustic Cell Filtration Device for Cell Retention: Characterization of Separation Efficiency and Impact of Perfusion on Product Quality," Biotechnology and Bioengineering, Aug. 2000, 69: 440-449.

Sadelain et al., "The promise and potential pitfalls of chimeric antigen receptors," Current Opinion in Immunology, 2009, 21: 215-223.

Sadikova et al., "Cell Concentration and Separation in the Field of a Standing Ultrasonic Wave for Medicine and Biotechnology," Open Journal of Biophysics, 2013, 3: 70-75.

Safdar et al., "The potential of endurance exercise-derived exosomes to treat metabolic diseases," Nature Reviews, 2016, 1-14.

Salmikangas et al., "Manufacturing, characterization and control of cell-based medicinal products: challenging paradigms toward commercial use," Regen. Med., 2015, 10: 64-78.

(56) References Cited

OTHER PUBLICATIONS

Sapozhnikov and Bailey, "Radiation force of an arbitrary acoustic beam on an elastic sphere in a fluid," J. Acoust. Soc. Am., Feb. 2013, 661-676.
Sarvazyan et al., "Acoustic Nonlinearity Parameter B/A of Aqueous Solutions of Some Amino Acids and Proteins," J. Acoust. Soc. Am. 88:3, 1555-1561, 1990.
Saxena et al., "Molecular Interactions in Binary Mixture of Polymethylmethaciylate with Acetic Acid," International Journal of Chemistry, 2:2, 9 pages, 2010.
Schliephake et al., "Overview of Treatment Processes for the Production of Fit for Purpose Water: Desalination and Membrane Technologies," Desalination and Membrane Technologies, Jul. 2005, 157 pages.
Schmidt et al., "Applying the Analytic Hierarchy Process in healthcare research: A systematic literature review and evaluation of reporting," BMC Medical Informatics and Decision Making, 2015, 15: 112.
Schnegas et al., "3D modeling and Computational Fluid Dynamics simulations of surface-attached CHO—K1 cells going to detach from a microchannel wall," Powder Technology, 2013, 237: 529-536.
Senapati et al., "Predicting Viscosity of Limestone-Water Slurry," Journal of Minerals & Materials Characterization & Engineering, 2009, 8: 203-221.
Sepehrirahnama, "Computation of Acoustic Radiation and Interparticle Forces for Spheres in Microfluidic Devices," Department of Mechanical Engineering, National University of Singapore, 2015, 156 pages.
Setayeshgar et al., "Particle Motion in a Macroscale, Multiwavelength Acoustic Field," Journal of Fluids Engineering, Jan. 2015, 137: 011302.
Settnes and Bruus, "Forces acting on a small particle in an acoustical field in a viscous fluid," Physical Review E, 2012, 85: 016327.
Settness and Bruus, "On the forces acting on a small particle in an acoustical field in a viscous fluid," Department of Micro- and Nanotechnology, Technical University of Denmark, Oct. 2011, 12 pages.
Shi et al., "Isolation of Rare Tumor Cells from Blood Cells with Buoyant Immuno-Microbubbles," PLOS One, Mar. 2013, 8: e58017.
Shimeta and Jumars, Physical mechanisms and rates of particle capture by suspension-feeders, Oceanogr. Mar. Biol. Annu. Rev., 1991, 29: 191-257.
Shirgaonkar et al., "Acoustic cell filter: a proven cell retention technology for perfusion of animal cell cultures," Biotechnology Advances, 2004, 22: 433-444.
SingleUse Chromatography: Where Promise Meets Reality, Bioprocessing Perspective, Mar. 2015, 35: 1-3.
Sinha and Kaduchak, "Noninvasive Determination of Sound Speed and Attenuation in Liquids," Experimental Methods in the Physical Sciences, 2001, 39: 307-333.
Sinha et al., "Applications of Swept-Frequency Acoustic Interferometry Technique in Chemical Diagnostics," DNA Sponsored Conference, Orlando, Florida, Jan. 25, 1996, 9 pages.
Sitters et al., "Acoustic force spectroscopy," Nature Methods, Jan. 2015, 12(1):47-50, doi: 10.1038/nmeth.3183, 7 pages.
Smith et al., "Creating a Completely "Cell-free" System for Protein Synthesis," Biotechnol. Prog., 2015, 1716-1719.
Smith et al., "In vitro comparison of two different methods of cell washing," Perfusion, 2012, 28: 34-37.
Spelt et al., "Attenuation of Sound in Concentrated Suspensions: Theory and Experiments," J. Fluid Mech. 430: 51-86, 2001.
Spengler et al., "Microstreaming Effects on Particle Concentration in an Ultrasonic Standing Wave," AIChE Journal, Nov. 2003, 49: 2773-2782.
Spengler and Jekel, "Ultrasonically Enhanced Sedimentation—Results of a Semi-Empirical Scale-Up Approach," 137th Meeting Acoustical Society of America and 2nd Convention European Acoustics Association: Forum Acusticum, Berlin, Germany, 1999, 4 pages.
Spengler et al., "Ultrasound conditioning of suspensions—studies of streaming influence on particle aggregation on a lab- and pilot-plant scale," Ultrasonics, Mar. 2000, 38(1-8):624-628.
Spiegler and El-Sayed, "The energetics of desalination processes," Desalination, 2001, 134: 109-128.
Stack et al., "Factors Influencing the Ultrasonic Separation of oil-in-water emulsions," Ultrasonics Somochemistry, 12: 153-160, 2005.
Startz et al., "Expansion of T-Cells in an Automated, Functionally Closed Hollow-Fiber Bioreactor System," TERUMOBCT, May 2016, 8 pages.
Steeg, "Targeting metastasis," Nature Reviws, Apr. 2016, 16: 201-218.
Stefano Oberti and Jurg Dual, Micro and Nano Techniques for the Handling of Biological Samples, Ultrasonic Manipulation Techniques, 39 pages, 2012.
Stride and Saffari, "Microbubble ultrasound contrast agents: a review," Proc. Instn Mech. Engrs, 2003, 217: 429-447.
Strom-Jensen, "Ultrasonic Absorption in Solutions of Proteins and Peptides and in Suspensions of Liposomes," Graduate College of the University of Illinios at Urbana-Champaign, 1983, 152 pages.
Stucki et al., "Electrochemical waste water treatment using high overvoltage anodes Part II: Anode performance and applications," Journal of Applied Biochemistry, 1991, 21: 99-104.
Stucki et al., "In Situ Production of Ozone in Water Using a Membrel Electrolyzer," J. Electrochem. Soc., Feb. 1985, 132: 367-371.
Sturtevant et al., "An acoustic resonance measurement cell for liquid property determinations up to 250° C.," Review of Scientific Instruments, 2012, 83: 115106.
Stuyfzand and Kappelhof, "Floating, high-capacity desalting islands on renewable multi-energy supply," Desalination, 2005, 177: 259-266.
Su et al., Ultrasound-based and Non-viral Technologies in Gene Therapy, J Intern Med Taiwan, 2007, 18: 167-181.
Swartz et al., "On the Generation of High-Frequency Acoustic Energy with Polyvinylidene Fluoride," IEEE Transactions on Sonics and Ultrasonics, 27:6, 295-303, 1980.
Szpyrkowicz et al., "Influence of anode material on electrochemical oxidation for the treatment of tannery wastewater," Water Research, 2005, 39: 1601-1613.
Takagi et al., "Continuous particle separation in a microchannel having asymmetrically arranged multiple branches," Lab on a Chip, 2005, 5: 778-784.
Tandiono et al., "Resonant stretching of cells and other elastic objects from transient cavitation," Soft Matter, 2013, 9: 8687-8696.
Teisseire et al., Ultrasonic backscatter coefficient quantitative estimates from Chinese hamster ovary cell pellet biophantoms, J. Acoust. Soc. Am., Nov. 2010, 3175-3180.
Temkin, "Attenuation and dispersion of sound in dilute suspensions of spherical particles," J. Acoust. Soc. Am., Jul. 2000, 108: 126-146.
Temkin, "Erratum: "Attenuation and dispersion of sound in dilute suspensions of spherical particles" [J. Acoust. Soc. Am. 108, 126-146 (2000)]," J. Acoust. Soc. Am., Feb. 2002, 111: 1126-1128.
Temkin, "Sound propagation in dilute suspensions of rigid particles," J. Scoust. Soc. Am., Feb. 1998, 103: 838-849.
Teng et al., "Effect of ultrasound on the separation of binary protein mixtures by cross-flow ultrafiltration," Desalination, 2006, 200: 280-282.
Tenneti et al., "Drag law for monodisperse gas-solid systems using particle-resolved direct numerical simulation of flow past fixed assemblies of spheres," International Journal of Multiphase Flow, 2011, 37: 1072-1092.
Tenneti, "Momentum, energy and scalar transport in polydisperse gas-solid flows using particle-resolved direct numerical simulations," Graduate Theses and Dissertations, 2013, 273 pages.
Teppo, "Screening of cell-drug interactions using acoustic trapping and MALDI MS," Lund University, Department of Biomedical Engineering, 2014, 65 pages.

(56) References Cited

OTHER PUBLICATIONS

Thormahlen et al., "Refractive Index of Water and Its Dependence on Wavelength, Temperature, and Density," J. Phys. Chem. Ref. Data., 1985, 14: 933-945.
Timm et al., "Toward Microfl uidic Reactors for Cell-Free Protein Synthesis at the Point-of-Care," small, 2014, 8 pages.
Tomizawa et al., "Sonoporation: Gene transfer using ultrasound," World Journal of Methodology, 2013, 3: 39-44.
Torres-Palma et al., "An innovative ultrasound, Fe2D and TiO2 photoassisted process for bisphenol a mineralization," Water Research, 2010, 1-8.
Tostoes et al., "A novel filtration system for point of care washing of cellular therapy products," J Tissue Eng Regen Med, 2016, 11 pages.
Townsend, "Investigation of two-dimensional acoustic resonant modes in a particle separator," Ultrasonics, 2006, 44: e467-e471.
Townsend, "Modelling of a Microfluidic Ultrasonic Particle Separator," Thesis for the degree of Doctor of Philosophy, University of Southampton, School of Engineering Sciences, Feb. 2006, 261 pages.
Trampler et al., "Acoustic Cell Filter for High Density Perfusion Culture of Hybridoma Cells," Bio/technology Mar. 1, 1994, 12(3):281-284.
Tran et al., "Fast acoustic tweezers for the two-dimensional manipulation of individual particles in microfluidic channels," Applied Physics Letters, 2012, 1-4.
Treindl et al., "A bead-based western for high-throughput cellular signal transduction analyses," Nature Communications, 2016, 7: 12852.
Trendowski, "Using the Promise of Sonodynamic Therapy in the Clinical Setting against Disseminated Cancers," Chemotherapy Research and Practice, 2015: 316015 (16 pages).
Tribler, "Acoustic streaming in microchannels: The trinity of analytics, numerics and experiments," Deparment of Physics, Technical University of Denmark, Sep. 2015, 148 pages.
Trujillo et al., "Multiphysics modelling of the separation of suspended particles via frequency ramping of ultrasonic standing waves," Ultrasonics, 2013, 20: 655-666.
Trujillo et al., "Separation of Suspensions and Emulsions via Ultrasonic Standing Waves—A Review," Ultrasonics Sonochemistry, 21: 2151-2164, 2014.
Tsutsui and Ho, "Cell separation by non-inertial force fields in microfluidic systems," Mechanics Research Communications, 2009, 36: 92-103.
Tuziuti et al., "Measurement of Distribution of Acoustic Radiation Force Perpendicular to Sound Beam Axis," Jpn. J. Appl. Phys., 1999, 38: 3297-3301.
Urban et al.,"Generalized response of a sphere embedded in a viscoelastic medium excited by an ultrasonic radiation force," J. Acoust. Soc. Am., Sep. 2011, 130: 1133-1141.
Van Saarloos and Mazur, "Many-Shere Hydrodynamic Interaction: Mobilities at Finite Frequencies," Physica, 1983, 120A: 77-102.
Van Wijhe, "Acoustic coagulation of aerosols," 2013, 68 pages.
Vanherberghen et al., "Ultrasound-controlled cell aggregation in a multi-well chip," Lab on a Chip, 2010, 10: 2727-2732.
Veerasamy et al., "Evaluating the use of in-situ ultrasonication to reduce fouling during natural rubber skim latex (waste latex) recovery by ultrafiltration," Desalination, 2009, 236: 202-207.
Vonk et al., "Intraoperative cell salvage is associated with reduced postoperative blood loss and transfusion requirements in cardiac surgery: a cohort study," Transfusion, Nov. 2013, 53: 2782-2789.
Wang and Ahe, "Recent advances in particle and droplet manipulation for lab-on-a-chip devices based on surface acoustic waves," Lab Chip, 2011, 11: 1280-1285.
Wang et al, "A linear relation between the compressibility and density of blood," J. Acoust. Soc. Am., Jan. 2001, 109: 390-396.
Wang et al., "Electronic Controlled Piezoelectric Array for Ultrasonic Particle Manipulation in an Acoustic Resonator," Acoustofluidics, Sep. 2013, 30 pages.
Wang et al., "Microfluidic acoustophoretic force based low-concentration oil separation and detection from the environment," Lab Chip, 2014, 14: 947-956.
Wang et al., "Simple Filter Microchip for Rapid Separation of Plasma and Viruses from Whole Blood," International Journal of Nanomedicine, 7: 5019-5028, 2012.
Wang et al., Proceedings of Meetings on Acoustics, 2013, 19: 045019.
Wang, "Study of High-Throughput Particle Separation Deveice Based on Standing Surface Acoustic Wave (SSAW) Technology," The University of Akron, Aug. 2012, 98 pages.
Wang, "Two Approaches for Cell Retention in Perfusion Culture Systems," Department of Chemical and Biomedical Engineering and the College of Graduate Studies, Cleveland State University, Dec. 2009, 167 pages.
Ward et al., "Ultrasound-induced cell lysis and sonoporation enhanced by contrast agents," J. Acoust. Soc. Am., May 1999, 105: 2951-2957.
Warkiani et al., "Next-Generation Microfilter: Large Scale, Continuous Mammalian Cell Retention for Perfusion Bioreactors," 18th International Conference on Miniaturized Systems for Chemistry and Life Sciences, Oct. 26-30, 2014, 3 pages.
Weaver et al., "Entrainment and Stimulated Emission of Ultrasonic Piezoelectric Auto-Oscillators," J. Acoust. Soc. Am. 122: 6, 3409-3418, 2007.
Weiser and Apfel, "Extension of acoustic levitation to include the study of micron-size particles in a more compressible host liquid," J. Acoust. Soc. Am., May 1982, 71: 1261-1268.
Western New England University Site Supervisor Evaluation, Aug. 2016, 1 page.
Westervelt, "The Theory of Steady Forces Caused by Sound Waves," The Journal of the Acoustical Society of America, May 1951, 23: 312-315.
Whitehill et al., "Collection of suspended particles in a drop using low frequency vibration," Applied Physics letter, 2010, 96: 053501.
Whitworth and Coakley, "Particle column formation in a stationary ultrasonic field," J. Acoust. Soc. Am., Jan. 1992, 91: 79-85.
Whitworth and Nyborg, "A rotating ultrasonic waveguide for studying acoustic radiation forces on particles," J. Acoust. Soc. Am., Oct. 1991, 90: 2091-2096.
Wijshoff, "The dynamics of the piezo inkjet printhead operation," Physics Report, 2010, 491: 77-177.
Wiklund an Hertz, "Ultrasonic enhancement of bead-based bioaffinity assays," Lab on a Chip, 2006, 6: 1279-1292.
Williams et al., "Field-Flow Fractionation: Addressing the Nano Challenge," Anal. Chem., 2011, 83: 634-642.
Williams, "What is field-flow fractionation?," available online on or before Aug. 2, 2010, Colorado School of Mines, retrieved from URL <http://inside.mines.edu/~krwillia/FFF_basics.pdf>, 3 pages.
Willis, "When size matters: Researchers are using field flow fractionation to determine the size of everything from colloids to polymers to human cells," Today's Chemist at Work, Jul. 2002, 21-24.
Wilson and Davis, "The viscosity of a dilute suspension of rough spheres," J. Fluid Mech., 2000, 421: 339-367.
Woodside et al., "Measurement of Ultrasonic Forces for Particle-Liquid Separations," AIChE Journal, Jul. 1997, 43: 1728-1736.
Wortham et al., "A Brief History of Blood Filtration: Clot Screens, Microaggregate Removal, and Leukocyte Reduction," Transfusion Medicine Reviews, Jul. 2003, 17: 216-222.
Xia and Lam, "Velocity and Concentration Measurements in Initial Region of Submerged Round Jets in Stagnant Environment and in Coflow," Journal of Hydro-Environment Research, 2009, 3: 21-34.
Yang et al., "Perfusion Seed Cultures Improve Biopharmaceutical Fed-Batch Production Capacity and Product Quality," Biotechnol. Prog., 2014, 30: 616-625.
Yasuda et al., "Deoxyribonucleic acid concentration using acoustic radiation force," J. Acoust. Soc. Am., Feb. 1996, 1248-1251.
Yasuda et al., "Using acoustic radiation force as a concentration method for erythrocytes," J. Acoust. Soc. Am., Jul. 1997, 102: 642-645.

(56) References Cited

OTHER PUBLICATIONS

Yen., "Experimental Investigation of Subharmonic Generation in an Acoustic Interferometer," J. Acoust. Soc. Am., 57:6, 1357-1360, 1975.

Yildiz et al., "Aligned carbon nanotube sheet high efficiency particulate air filters," Carbon, Nov. 2013, 64: 295-304.

Yong et al., "Microbubble-mediated sonoporation for highly efficient transfection of recalcitrant human B-cell lines," Biotechnol. J., 2014, 9: 1081-1087.

Yosioka and Kawasima, "Acoustic Radiation Pressure on a Compressible Sphere," Acustica, 1955, 5: 168-173.

Yue et al., "Miniature Field-Flow Fractionation System for Analysis of Blood Cells," Clin. Chem., 1994, 40: 1810-1814.

Zauhar et al., "Studies of acoustic streaming in biological fluids with an ultrasound Doppler technique," The British Journal of Radiology, Mar. 1998, 71(843):297-302.

Zavtrak., "Acoustical Laser with Mechanical Pumping," J. Acoust. Soc. Am. 99: 2, 730-733, 1996.

Zemella et al., "Cell-Free Protein Synthesis: Pros and Cons of Prokaryotic and Eukaryotic Systems," ChemBioChem, 2015, 16: 2420-2431.

Zhang, "Orientation of Piezoelectric Crystals and Acoustic Wave Propagation," Excerpt from the Proceedings of the 2012 COMSOL Conference in Boston, 2012, 18 pages.

Zhang, "Orientation of Piezoelectric Crystals and Acoustic Wave Propagation," Excerpt from the Proceedings of the 2012 COMSOL Conference in Boston, 2012, 4 pages.

Zheng et al., "3D microfilter device for viable circulating tumor cell (CTC) enrichment from blood," Biomed Microdevices, Feb. 2011, 13: 1-22.

Zhou et al., "Impact of instantaneous uniformity of SonoVue microbubbles on binding characteristics of a new contrast agent targeted to choriocarcinoma cells in vitro," Chinese Journal of Cancer, Jul. 2008, 27: 21-25.

Zhu et al., "Microfluidic Enrichment of Mouse Epidermal Stem Cells and Validation of Stem Cell Proliferation In Vitro," Tissue Engineering: Part C, 2013, 19: 765-773.

Zhu et al., "Particle Wake Effects on the Drag Force of an Interactive Particle," Int. J. Multiphase Flow, 1994, 20: 117-129.

Zhu et al., "Microfluidic Enrichment of Mouse Epidermal Stem Cells and Validation of Stem Cell Proliferation in Vitro," Tissue Engineering: Part C, 19:10, 10 pages, 2013.

Ziegler and Groscurth, "Morphological Features of Cell Death," News Physiol Sci, 2004, 19: 124-128.

Zipursky et al., "Leukocyte Density and Volume in Normal Subjects and in Patients with Acute Lymphoblastic Leukemia," Blood, Sep. 1976, 48: 361-371.

ACOUSTOPHORETIC DEVICE FOR ANGLED WAVE PARTICLE DEFLECTION

CROSS-REFERENCE TO RELATED APPLICATIONS

This application claims priority to U.S. Provisional Patent Application Ser. No. 62/316,933, filed on Apr. 1, 2016; and to U.S. Provisional Patent Application Ser. No. 62/154,690, filed on Apr. 29, 2015, the disclosures of which are hereby fully incorporated by reference in their entireties.

BACKGROUND

In the medical field, it often is desirable to separate low concentration cells from a fluid mixture with no harm to the cells, wash cells, concentrate cells in a fluid mixture, differentiate cells based on key parameters, or even fractionate many different types of cells. Such processes are key in the development of possible cures to many common diseases. It may also be desirable to separate particles or cells different in size, density and or acoustic contrast factor through the use of an acoustic field where the particles may be separated from each other as well. Examples include the separation of live from dead cells, and the separation of differentiated from undifferentiated cells. The methods described herein provide for such a separation or fractionation method that is label-free.

In the food and beverage industry, filter cartridges and filter membranes have conventionally been used to filter particles from liquids. Such filters are expensive and become clogged and non-functional as material is processed. In contrast, acoustophoresis provides, among other possible advantages, a solid-state, low-cost alternative to filter cartridges and filter membranes that is capable of processing large quantities of a host medium, for example water or beer, that is laden with yeast or other suspended particles.

In the food and beverage industry, host fluid is flowed through filters at flow rates up to ten times greater than those through conventional acoustophoresis devices. At these higher flow rates, trapping of the particles in the host fluid is decreased, thereby leading to decreased separation efficiency. It would therefore be desirable to provide systems and methods capable of separating a second fluid or a particulate from a host fluid at much higher flowrates, or at much lower concentrations, than conventional macro-scale acoustic separators.

In the oil and water industry, efficiently and economically separating oil and other contaminants from water has become an important process. The rise of fracking techniques has led to many settling ponds and large costs for transportation of contaminated water. These settling ponds are a challenge to the environment and better means are needed to more effectively clarify fracking water. Acoustophoresis provides, among other possible advantages, a solid-state, effective means of clarifying fracking, but the flow rates associated with such macro-scale acoustophoresis devices is still too low to be feasible. It would therefore be desirable to provide systems and methods capable of separating a second fluid, cell, or particulate from a host fluid at much higher flowrates.

BRIEF DESCRIPTION

The present disclosure relates, in various embodiments, to mini to macro-scale systems, devices, and methods for acoustophoresis to separate, fractionate, isolate, concentrate, wash, detect, or even differentiate cells or particles in fluid suspension. The devices and methods include a flow chamber containing an ultrasonic transducer and reflector that set up an angled acoustic standing wave oriented at an acute angle relative to the direction of mean flow through the flow chamber, which includes the particle path through the angled acoustic standing wave. At higher flow rates, acoustic standing waves may be used to deflect the particles in a desired direction, without causing the particles to become trapped in the standing wave. By applying the acoustic standing wave to the host fluid at an angle thereto, desired deflection of the particles can be achieved.

Disclosed herein is an acoustophoresis device comprising: a flow chamber through which is flowed an initial mixture of a host fluid and at least one of a second fluid, a cell, or a particulate, the flow chamber defining a direction of mean flow; at least one ultrasonic transducer located on a wall of the flow chamber, the transducer including a piezoelectric material driven by a voltage signal to create an angled acoustic standing wave in the flow chamber oriented at an acute angle relative to the direction of mean flow through the flow chamber; and a reflector located on a wall on an opposite side of the flow chamber from the at least one ultrasonic transducer, and the reflector is designed and positioned to create a standing wave along the acute angle direction. As examples, the transducer may be in direct contact with the fluid in the chamber, it may be adhesively attached to a polymer film, or it may be used to excite a second material to generate acoustic standing waves. Further, the transducer may utilize a piezoelectric material that is ceramic, such as a PZT-8, or polymer such as polyvinylidene fluoride (PVDF).

In particular embodiments of the device, the angled acoustic standing wave is oriented at an angle of about 20° to about 70° relative to the direction of mean flow through the flow chamber. The multi-dimensional acoustic standing wave can be a three-dimensional acoustic standing wave. The angled acoustic standing wave may also be a planar acoustic standing wave, or a combination of planar acoustic standing waves and multi-dimensional acoustic standing waves.

In certain embodiments of the device, the acoustophoresis device further comprises an inlet at a first end of the flow chamber and a clarified fluid outlet at a second end of the flow chamber opposite the first end. The acoustophoresis device may further comprise a concentrate outlet at the second end of the flow chamber. The at least one concentrate outlet at the second end of the flow chamber may lead to a further process such as cell washing, cell concentration or cell fractionation where the cells are biological cells such as T cells, B cells and NK cells. In certain embodiments, the cells separated are Chinese hamster ovary (CHO) cells, NSO hybridoma cells, baby hamster kidney (BHK) cells, or human cells. The use of mammalian cell cultures including the aforementioned cell types has proven to be a very efficacious way of producing/expressing the recombinant proteins and monoclonal antibodies required of today's pharmaceuticals.

In certain embodiments of the device, the acoustophoresis device further comprises a deflection wall below the clarified fluid outlet, the deflection wall extending substantially perpendicular to the direction of mean flow through the flow chamber. The acoustophoresis device can include a concentrate outlet at a lower end of the deflection wall. The angled acoustic standing wave can be a multi-dimensional acoustic standing wave that results in an acoustic radiation force having an axial force component that deflects the second fluid, cell, or particulate into the deflection wall. The angled acoustic standing wave can be a three-dimensional acoustic standing wave.

In certain embodiments of the device, the acoustophoresis device can include a plurality of ultrasonic transducers arranged in series, each transducer including a piezoelectric material driven by a voltage signal to create an angled acoustic standing wave in the flow chamber oriented at an angle of about 20° to about 70° relative to the direction of mean flow through the flow chamber. Each transducer of the plurality of transducers can be oriented at the same angle relative to the direction of mean flow through the flow chamber.

In particular embodiments, the acoustophoresis device can further comprise an upper inlet duct through which the initial mixture of the host fluid and at least one of the second fluid, cell, or particulate flows into the acoustophoresis device; a lower inlet duct through which a cell wash flows into the acoustophoresis device; an upper duct exit through which the host fluid of the initial mixture flows out of the acoustophoresis device; a middle duct exit through which the wash fluid flows out of the acoustophoresis device; and a lower duct exit where the second fluid, cell, or particulate concentrates after passing from the flow of the initial mixture through the upper inlet duct through the cell wash flow.

The acoustic chamber or chambers may also incorporate a straight path, such as that generated by a glass tube that runs down the center line of the angled wave acoustic device. In this instance, the acoustic wave is transmitted through the wall of the glass tube and the main flow through the acoustic device is not disrupted by the angular portions of the transducers and reflectors at the edges of the acoustic device.

Also disclosed is a method of separating a second fluid, a cell, or a particulate from a host fluid. The method comprises: flowing an initial mixture of the host fluid and at least one of the second fluid, the cell, or particulate through an acoustophoresis device; sending a voltage signal to drive the at least one ultrasonic transducer to create the angled standing wave in the flow chamber to deflect the second fluid, cell, or particulate; and collecting the second fluid, cell, or particulate from the acoustophoresis device. The acoustophoresis device comprises a flow chamber through which is flowed the initial mixture of the host fluid and at least one of the second fluid, the cell, or the particulate, the flow chamber defining a direction of mean flow; at least one ultrasonic transducer located on a wall of the flow chamber, the transducer including a piezoelectric material driven by a voltage signal to create an angled acoustic standing wave in the flow chamber oriented at an acute angle relative to the direction of mean flow through the flow chamber; and a reflector located on a wall on an opposite side of the flow chamber from the at least one ultrasonic transducer. In particular embodiments of the method, the angled standing wave is oriented at an angle of about 20° to about 70° relative to the direction of mean flow through the flow chamber. The angled acoustic standing wave can be a multi-dimensional acoustic standing wave, such as a three-dimensional acoustic standing wave. The angled acoustic standing wave can be a three-dimensional acoustic standing wave. The flow chamber of the acoustophoresis device can further include an upper inlet duct through which the initial mixture of the host fluid and at least one of the second fluid, cell, or particulate flows into the acoustophoresis device; a lower inlet duct through which a cell wash flows into the acoustophoresis device; an upper duct exit through which the host fluid of the initial mixture flows out of the acoustophoresis device; a middle duct exit through which the wash fluid flows out of the acoustophoresis device; and a lower duct exit where the second fluid, cell, or particulate concentrates after passing from the flow of the initial mixture through the upper inlet duct through the cell wash flow.

In certain embodiments of the method, the acoustophoresis device further comprises an inlet at a first end of the flow chamber and a clarified fluid outlet at a second end of the flow chamber opposite the first end. The acoustophoresis device used in the disclosed method may further comprise a concentrate outlet at the second end of the flow chamber.

In yet another embodiment, there may be two parallel inlets, one containing a fluid and cell mixture, e.g., from a cell culture, and the second a washing fluid. The device also contains two outlets, one for the cell culture fluid, and the other for the washing fluid. The action of the angled acoustic standing wave is to move all suspended cells from the original cell culture fluid into the washing fluid, thereby accomplishing a washing process.

In another embodiment, there is a single inlet to the device containing a fluid mixture containing microcarriers, e.g., cytodex beads, and cells in suspension, e.g., from an adherent cell culture after cells have been separated from the microcarriers through, e.g., a trypsinization process. The action of the angled acoustic standing wave results in the separation of the fluid into two streams, one a fluid stream containing all the cells, and the other a fluid stream containing all the microcarriers.

In certain embodiments of the method, the acoustophoresis device can include a plurality of parallel collection ducts designed to collect cells or particulates of different properties that were fractionated by the angled acoustic wave forces.

In certain embodiments of the method, the acoustophoresis device can include an operating mode coupled to at least two exit ducts used to collect cells or particles differentiated by the angled wave as a result of property differences.

In certain embodiments of the method, the acoustophoresis device further comprises a deflection wall below the clarified fluid outlet, the deflection wall extending substantially perpendicular to the direction of mean flow through the flow chamber. The acoustophoresis device used in the disclosed method can include a concentrate outlet at a lower end of the deflection wall. The angled acoustic standing wave can be a multi-dimensional acoustic standing wave that results in an acoustic radiation force having an axial force component that deflects the second fluid, cell, or particulate into the deflection wall. The second fluid, cell, or particulate can be collected from the acoustophoresis device via the concentrate outlet after deflection into the deflection wall.

In certain embodiments of the method, the acoustophoresis device can include a plurality of ultrasonic transducers arranged in series, each transducer including a piezoelectric material driven by a voltage signal to create an angled acoustic standing wave in the flow chamber oriented at an angle of about 20° to about 70° relative to the direction of mean flow through the flow chamber. Each transducer of the plurality of transducers can be oriented at the same angle relative to the direction of mean flow through the flow chamber.

The second fluid, cell, or particulate can be collected from the acoustophoresis device at a draw rate of about 200 to about 350 milliliters per minute.

The mixture of the host fluid and at least one of the second fluid, cell, or particulate can be flowed through the acoustophoresis device at a flow rate of about 400 to about 700 milliliters per minute. The voltage signal sent to the at least one ultrasonic transducer can be from about 5 V to about 200 V, or, more preferably, from about 5 V to about 50 V. The ultrasonic transducer can be operated at a frequency of about 0.2 MHz to about 200 MHz, or, more preferably, from about 0.5 MHz to about 10 MHz.

In particular embodiments of the method, the angled acoustic standing wave results in an acoustic radiation force on the second fluid, cell, or particulate; the flow of the mixture of the host fluid and at least one of the second fluid, cell, or particulate through the acoustophoresis device results in a viscous drag force on the second fluid, cell, or particulate; and a ratio of the acoustic radiation force to the viscous drag force is about 0.1 to about 0.9. In some embodiments, the acoustophoresis device is operated such that the acoustic radiation force is large enough to retard the second fluid, cell, or particulate from passing through the angled acoustic standing wave. In other embodiments, the acoustophoresis device is operated such that the second fluid, cell, or particulate passes through the angled acoustic standing wave.

In some constructions, the at least one ultrasonic transducer includes a plurality of ultrasonic transducers arranged in series and rotated relative to each other at an angle such that their acoustic standing waves are not parallel to each other. For example, the transducers may be angled 90° from each other. Each transducer includes a piezoelectric material driven by a voltage signal to create an angled three-dimensional acoustic standing wave in the flow chamber oriented at an angle of about 20° to about 70° relative to the direction of mean flow through the flow chamber to benefit differentiation, separation, concentration or fractionization of the second fluid, cell, or particulate.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
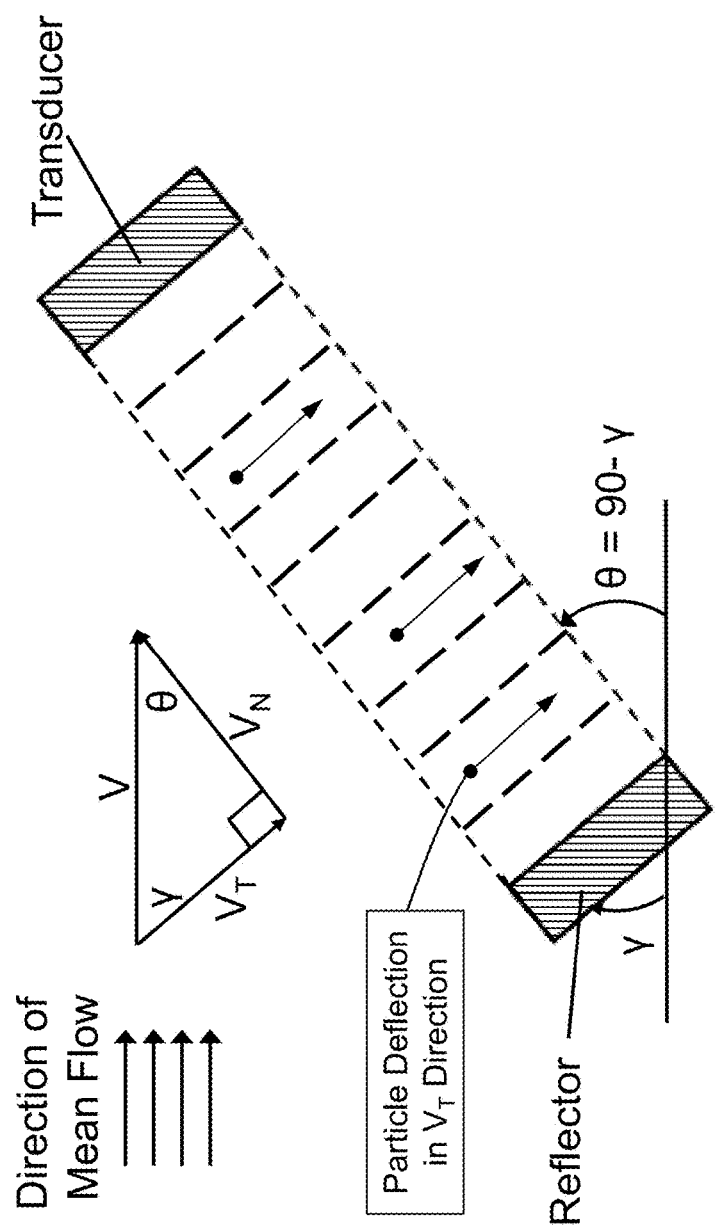
FIG. 1 schematically illustrates the flow velocity components of a particle as it approaches a left-running acoustic standing wave that deflects the particle in the direction of the velocity component $V_T$.
Figure 1A:
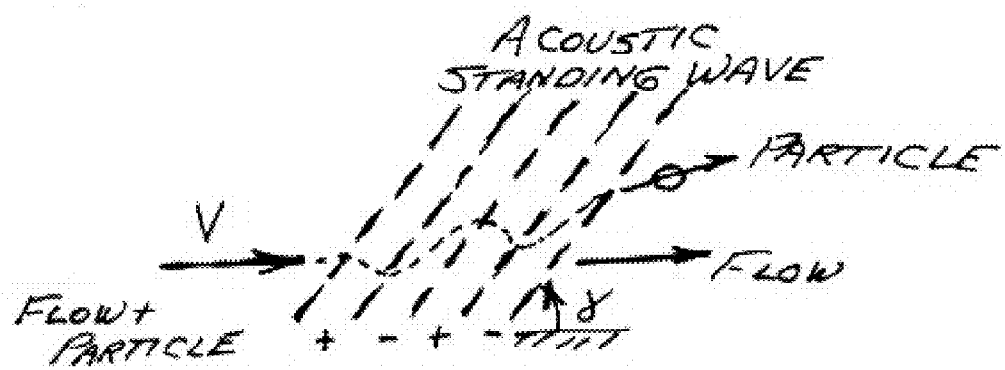

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that some of the terms used herein may be relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth. It is to be understood that gravity, or the effects of gravity, are negligible in the angled wave deflection process described herein, because the process works on individual particles, not much larger particle clusters as used in other systems.

The term "parallel" should be construed in its lay sense of two surfaces that maintain a generally constant distance between them, and not in the strict mathematical sense that such surfaces will never intersect when extended to infinity.

The present application may refer to "the same order of magnitude." Two numbers are of the same order of magnitude if the quotient of the larger number divided by the smaller number is a value of at least 1 and less than 10.

As explained previously, in conventional acoustophoresis devices, acoustic standing waves cause particles in a host fluid to collect, agglomerate, aggregate, clump, cluster, or coalesce at the nodes or anti-nodes of the acoustic standing wave, depending on the particles' acoustic contrast factor relative to the host fluid, forming clusters that eventually fall out of the standing wave due to enhanced gravity when the clusters have grown to a size large enough to overcome the holding force of the standing wave (e.g. by coalescence, clustering, or agglomeration). For fluids/particles that are more dense than the host fluid (e.g., cells), the clusters sink to the bottom of the device and can be collected separately from the clarified host fluid. For fluids/cells/particles that are less dense than the host fluid, the buoyant clusters float upwards to the top of the device and can be collected therefrom. In conventional acoustophoresis devices, the acoustic standing waves created therein generate acoustic radiation forces in the axial direction (i.e., in the direction of the standing wave) and in the lateral directions (i.e., perpendicular to the direction of the standing wave). In these devices, the axial force typically is perpendicular to the flow direction, and, as the mixture flows through the flow chamber, particles in suspension experience a strong axial force component in the direction of the standing wave. Since this acoustic force is perpendicular to the flow direction and the drag force, it quickly moves the particles to pressure nodal planes or anti-nodal planes, depending on the contrast factor of the particle. The clusters of particles form quickly as a result of lateral radiation forces and then drop out of the mixture due to enhanced gravity.

The present disclosure relates to acoustophoretic devices that employ multi-dimensional ultrasonic acoustic standing waves, planar acoustic standing waves or combinations of planar and multidimensional acoustic standing waves (collectively referred to herein as angled acoustic standing waves) oriented at an angle relative to the direction of mean flow through the device. The direction of mean flow through the chamber is to be understood to include the path traveled by a second fluid, cell, or particulate that is flowed through an angled acoustic standing wave generated in the device. These angled acoustic standing waves deflect particles in a host fluid stream, rather than trapping the particles for agglomeration. This is an important distinction from many current acoustophoresis devices. These devices disclosed herein can operate at high flowrates and can be used to replace costly and clog-prone filter cartridges and filter membranes in various industries. The devices and methods of the present disclosure rely primarily on the axial force component to deflect the particles out of the acoustic field, rather than relying on trapping, agglomeration, and gravitational and buoyancy forces. The devices and methods presented herein are capable of being operated independent of gravity (i.e., in any orientation), and do not rely on gravitational settling. In this way, the axial force of an angled acoustic standing wave oriented at an angle relative to the flow direction is capable of advantageously deflecting particles in fluid streams at high flow rates of up to about 400 mL/min, and more preferably up to about 600 mL/min or about 700 mL/min in devices with a cross section of 1 inch by 1 inch.

Thus, bulk acoustic standing waves angled relative to a direction of flow through a device can be used to deflect, collect, differentiate, or fractionate particles or cells from a fluid flowing through the device. The angled acoustic standing waves can be used to separate or fractionate particles in the fluid by size, density, speed of sound, or shape. The angled acoustic standing wave can be a three-dimensional acoustic standing wave. The acoustic standing wave may also be a planar wave where the piezoelectric material is excited in a piston fashion or the acoustic standing waves may be a combination of the planar acoustic standing waves and the multidimensional acoustic standing waves. For purposes of this disclosure, a standing wave where the lateral force is not the same order of magnitude as the axial force is considered a "planar acoustic standing wave." This can be used to separate live cells from dead cells, damaged cells from healthy cells, or differentiated from undifferentiated cells. The deflection of the particles by the standing wave can also be controlled or amplified by the strength of the acoustic field, the angle of the acoustic field, the properties of the fluid, the three dimensionality of the standing wave, the frequency of the standing wave, the acoustic chamber shape, and the mixture flow velocity.

When acoustic standing waves propagate in liquids, the fast oscillations may generate a non-oscillating force on particles suspended in the liquid or on an interface between liquids. This force is known as the acoustic radiation force. The force originates from the non-linearity of the propagating wave. As a result of the non-linearity, the wave is distorted as it propagates and the time-averages are nonzero. By serial expansion (according to perturbation theory), the first non-zero term will be the second-order term, which accounts for the acoustic radiation force. The acoustic radiation force on a particle, or a cell, in a fluid suspension is a function of the difference in radiation pressure on either side of the particle or cell. The physical description of the radiation force is a superposition of the incident wave and a scattered wave, in addition to the effect of the non-rigid particle oscillating with a different speed compared to the surrounding medium thereby radiating a wave. The following equation presents an analytical expression for the acoustic radiation force on a particle, or cell, in a fluid suspension in a standing wave.

$$F_R = \frac{3\pi P_0^2 V_P \beta_m}{2\lambda} \varphi(\beta, \rho) \sin(2kx) \quad (1)$$

where $\beta_m$ is the compressibility of the fluid medium, $\rho$ is density, $\phi$ is acoustic contrast factor, $V_p$ is particle volume, $\lambda$ is wavelength, k is $2\pi/\lambda$, $P_0$ is acoustic pressure amplitude, x is the axial distance along the standing wave (i.e., perpendicular to the wave front), and $$\varphi(\beta, \rho) = \frac{5\rho_p - 2\rho_m}{2\rho_p + \rho_m} - \frac{\beta_p}{\beta_m}$$

where $\rho_p$ is the particle density, $\rho_m$ is the fluid medium density, $\beta_p$ is the compressibility of the particle, and $\beta_m$ is the compressibility of the fluid medium.

For a multi-dimensional standing wave, the acoustic radiation force is a three-dimensional force field, and one method to calculate the forces is Gor'kov's method, where the primary acoustic radiation force $F_R$ is defined as a function of a field potential U, $F_R=-\Box(U)$, where the field potential U is defined as $$U = V_0 \left[ \frac{\langle p^2(x, y, z, t) \rangle}{2\rho_f c_f^2} f_1 - \frac{3\rho_f \langle v^2(x, y, z, t) \rangle}{4} f_2 \right]$$

and $f_1$ and $f_2$ are the monopole and dipole contributions defined by $$f_1 = 1 - \frac{1}{\Lambda \sigma^2} \quad f_2 = \frac{2(\Lambda - 1)}{2\Lambda + 1},$$

where $$\sigma = \frac{c_p}{c_f} \quad \Lambda = \frac{\rho_p}{\rho_f} \quad \beta_f = \frac{1}{\rho_f c_f^2}$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o$ is the volume of the cell, and < > indicates time averaging over the period of the wave.

Gork'ov's model is for a single particle in a standing wave and is limited to particle sizes that are small with respect to the wavelength of the sound fields in the fluid and the particle. It also does not take into account the effect of viscosity of the fluid and the particle on the radiation force. As a result, this model cannot be used for the macro-scale ultrasonic separators discussed herein since particle clusters can grow quite large. A more complex and complete model for acoustic radiation forces that is not limited by particle size was therefore used. The models that were implemented are based on the theoretical work of Yurii Ilinskii and Evgenia Zabolotskaya as described in AIP Conference Proceedings, Vol. 1474-1, pp. 255-258 (2012). These models also include the effect of fluid and particle viscosity, and therefore are a more accurate calculation of the acoustic radiation force.

The acoustic radiation force on a particle is seen to be a symmetric function having a period that is one half the acoustic wavelength. This means a particle will be accelerated and decelerated exactly the same by the radiation force. FIG. 1 schematically shows a mixture flowing through a standing wave, with the standing wave oriented at an angle relative to the direction of mean flow. The angled acoustic standing wave can be a three-dimensional acoustic standing wave. The acoustic standing wave may also be a planar wave where the piezoelectric material is excited in a piston fashion or the acoustic standing waves may be a combination of the planar acoustic standing waves and the multidimensional acoustic standing waves.

In FIG. 1, V is the velocity of an initial mixture of a host fluid and particles or particulates. The particles are deflected toward the wave front, or away from the wave axial direction as shown. FIG. 1 depicts a left running wave (i.e., the wave moves to the left when looking in the direction of the fluid flow). The fluid velocity can be decomposed into a velocity component $V_T$ parallel to the left running wave, and a velocity component $V_N$ normal to the wave, as shown in FIG. 1. In this case, a particle in suspension will be deflected in the $V_T$ direction. The direction of mean flow through the chamber is to be understood to follow the path traveled by the bulk mixture that is flowed through an angled acoustic standing wave generated in the device. In this regard, it is noted that when $V_T$ is in the upward direction (such as in FIG. 1), the acute angle γ is on the lower downstream portion of the acoustic standing wave.

Figure 2:
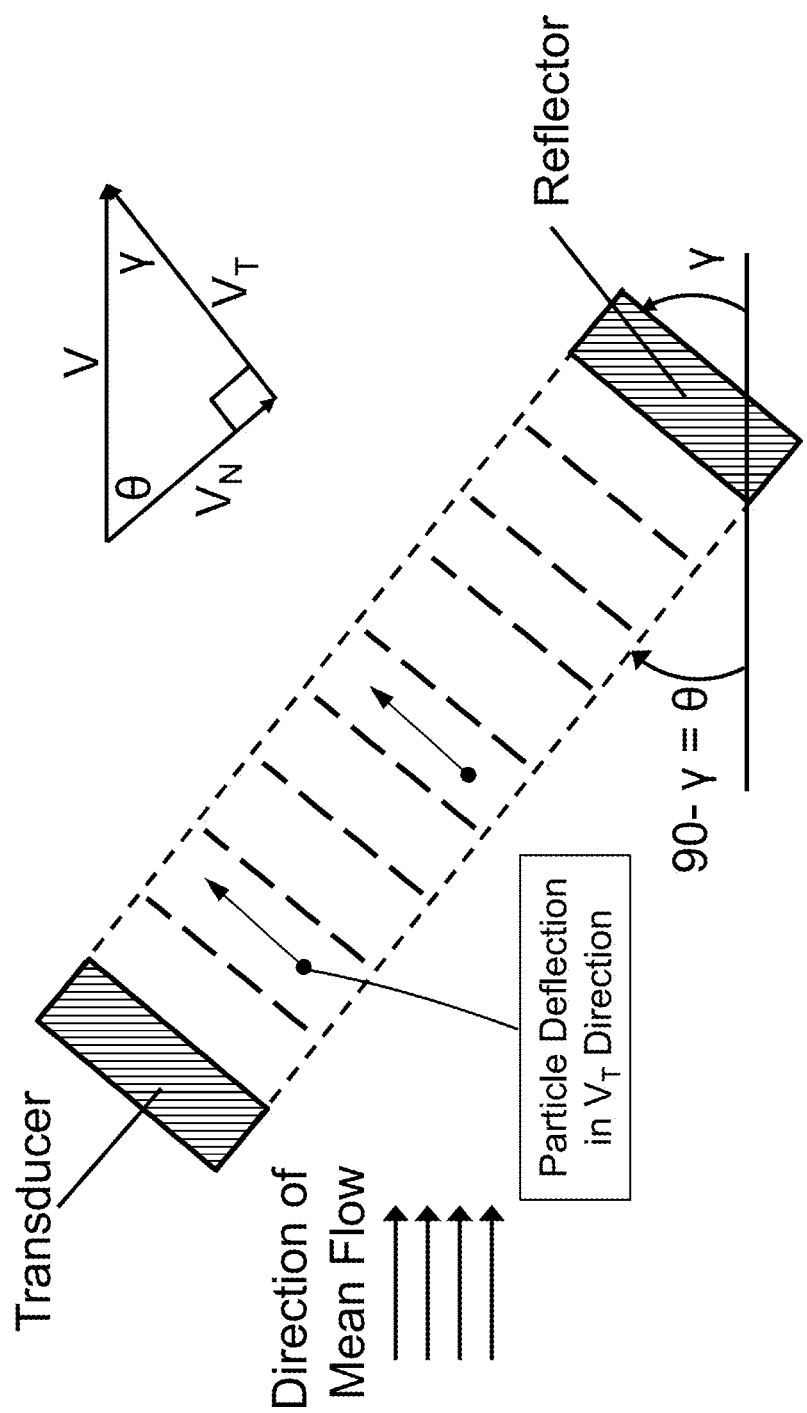
FIG. 2 schematically illustrates the flow velocity components of a particle as it approaches a right-running acoustic standing wave that deflects the particle in the direction of the velocity component $V_T$.

The particles are deflected in the direction of the tangential velocity component. FIG. 2 depicts a right running wave (i.e., the wave moves to the right when looking in the direction of the fluid flow). In this case, any particle in suspension will again be deflected in the $V_T$ direction. Again, the direction of mean flow through the chamber is to be understood to follow the path traveled by the bulk mixture that is flowed through an angled acoustic standing wave generated in the device. In this regard, it is noted that when $V_T$ is in the downward direction (such as in FIG. 2), the acute angle γ remains on the lower downstream portion of the acoustic standing wave. In other words, the angle γ (i.e., the angle of the acoustic standing wave relative to the direction of mean flow) is always measured from the lower downstream portion of the acoustic standing wave in the $V_T$ direction.

An angled acoustic standing wave, such as those shown in FIG. 1 and FIG. 2, can often be analyzed more simply by using a Galilean transformation. This transformation amounts to looking at the same problem while running along the wave at a velocity $V_T$ (i.e., parallel to the wave). Thus, the velocity component $V_T$ plus V (along the direction of mean flow) is equivalent to the velocity component $V_N$ (normal to the wave, irrespective of the wave angle). In other words, the physics of the problem do not change with such a transformation, which resultantly amounts to solving the flow through a standing wave with the flow direction perpendicular to the wave, or in the axial direction of the wave. In this direction, the acoustic radiation force variation, as presented in Equation 1, will result in a symmetrical series of velocity increases and decreases in the normal flow direction. Using v as the particle perturbation velocity resulting from the acoustic radiation forces on a particle as the mixture flows through a normal acoustic standing wave, the following governing equation can be generated (i.e., from Newton's second law, Equation 1 and Stokes drag):

$$\rho_P V_P \left( \frac{dv}{dt} \right) 6\pi\mu r_p v = \frac{3\pi P_0^2 V_P \beta_m}{2\lambda} \varphi(\beta, \rho) \sin(2kx) \quad (2)$$

The same expression was used to generate the net particle deflection angles at different As such, v is actually $\Delta V_N$, or the change in particle velocity normal to the standing wave resulting from the effects of the acoustic radiation forces on the particles as generated by the standing wave. The viscosity effects oppose the perturbation velocity, and act in a direction toward the mean velocity. As a result, the viscosity drives the particle perturbation velocity to fluctuate about the mean flow velocity with an amplitude of $\Delta V_N$. This effect is further verified by assuming the inertial term in Equation 2 is small. This assumption infers that the particles in suspension are small enough to instantly react to the viscous and radiation forces. With this assumption, the first term on the left side drops out, and Equation 2 can be reduced to:

$$v = C \sin(2kx) \quad (3)$$

where $$C = \frac{\pi}{3} \frac{r_p^2 \beta_m \varphi}{\mu \lambda} P_0^2$$

where C is a function of the acoustic pressure amplitude, $r_p$ is the particle radius, φ is the particle contrast factor, μ is the fluid viscosity, and λ is the acoustic wavelength. With this assumption, the particle velocity instantly adjusts to the Stokes velocity generated by the radiation force.

Figure 3:
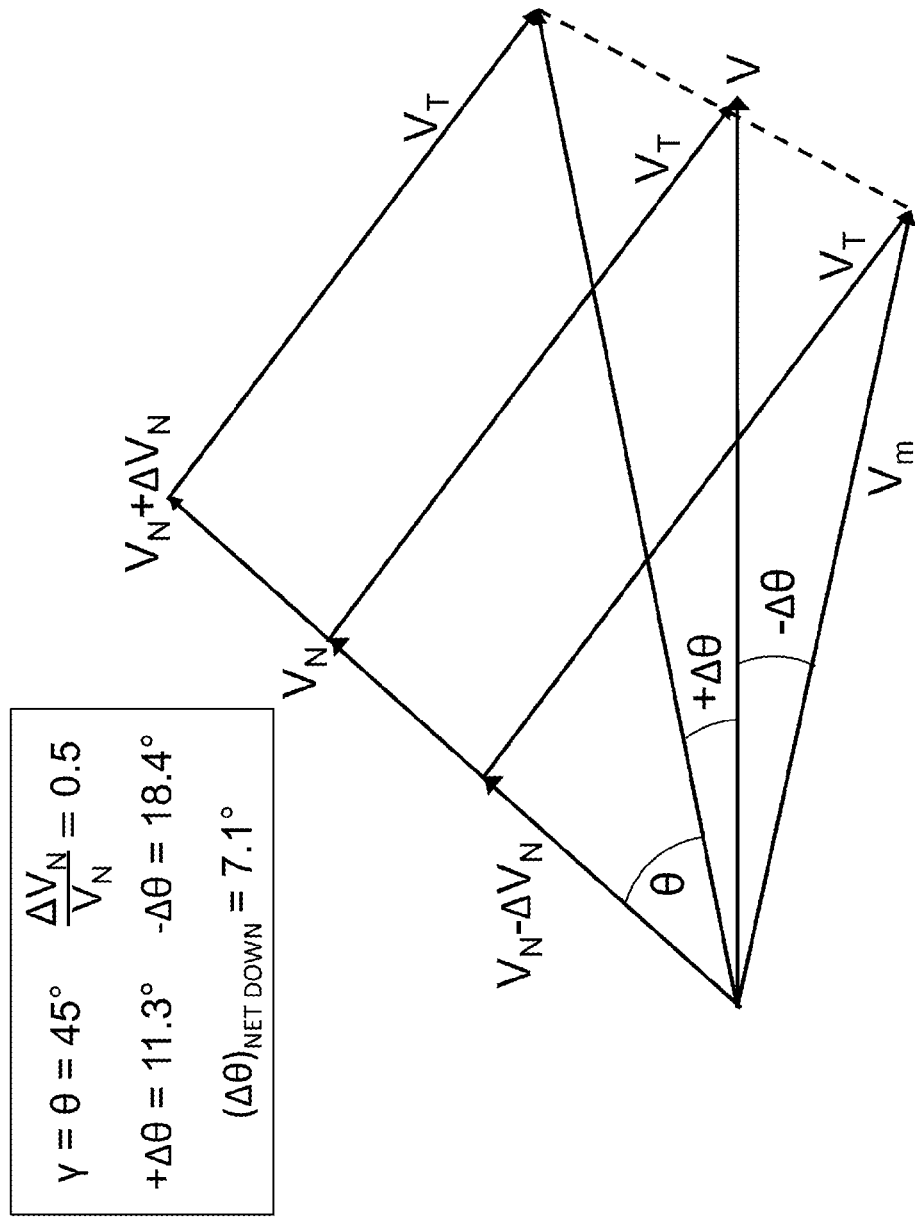
FIG. 3 schematically illustrates the particle deflection effect caused by increasing and decreasing the velocity component of a particle as it approaches an acoustic standing wave normal thereto and is deflected away from the standing wave axial direction (i.e., $V_T$).

Turning now to FIG. 3, the particle deflection effect caused by the decrease and increase of the velocity component normal to the acoustic standing wave is presented when the standing wave is at a 45-degree angle to the flow. As inferred by the Galilean transformation, the tangential velocity component has to remain constant as the velocity component normal to the acoustic standing wave varies symmetrically about the mean normal velocity. There are no forces tangent to the waves. Therefore, the tangential velocity component has to remain constant.

As seen by the flow triangles depicted in FIG. 3, this results in a visible difference in the particle deflection by the alternating normal velocity variation. The particle will have a net deflection angle away from the standing wave axial direction. Neglecting gravity effects, this will be true for both left and right running waves. Using this phenomena and the resulting geometry in FIG. 3, the following expression was generated for the change in particle flow angle ΔΘ (measured from the mixture flow velocity direction entering the standing wave) as a function of the change in normal velocity of the particle:

$$\pm \Delta\theta = \theta - \tan^{-1}\left[ \frac{1}{\left(1 \pm \frac{\Delta V_N}{V_N}\right)} \tan\theta \right] \quad (4)$$

The expression in Equation 4 was used to generate both the maximum upward deflection (+Δθ=11.3°) and the maximum downward deflection (−Δθ=18.4°), as shown in FIG. 3. These two deflections can be combined to generate the net deflection (Δθ=7.1°), as presented in FIG. 3.

Figure 4:
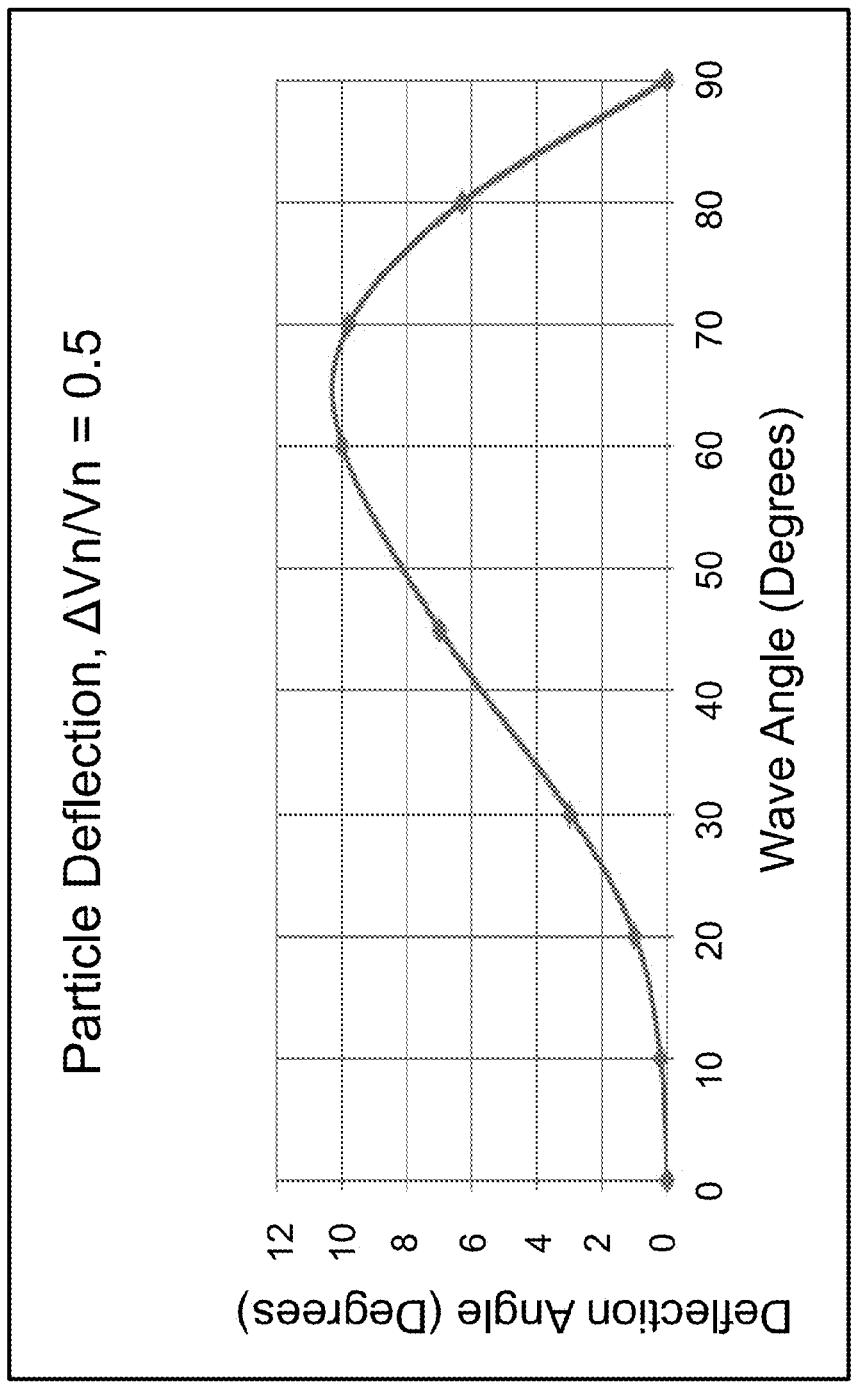
FIG. 4 is a graph illustrating the net particle deflection angles of a particle at different wave angles with a fixed acoustic radiation force ratio of 0.5.

The same expression was used to generate the net particle deflection angles at different wave angles. These results are presented in the graph of FIG. 4. Rotating the standing wave angle γ up or down can generate this effect. FIG. 4 shows, for the condition analyzed, that maximum particle deflection occurs with a wave angle between about 50° and about 75°. At an angle of 90°, no deflection occurs because the tangential velocity component, $V_T$, is zero.

Figure 5:
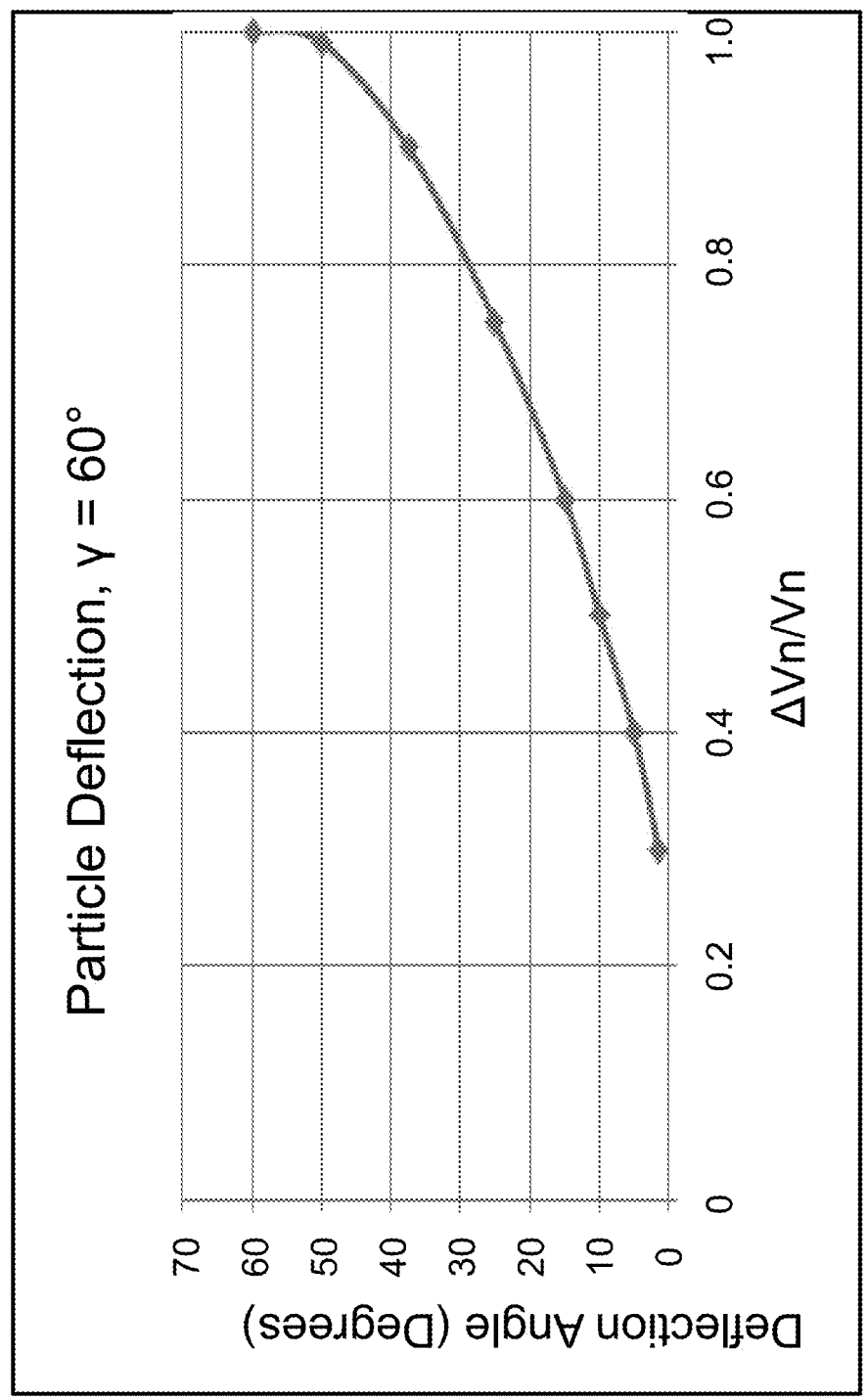
FIG. 5 is a graph illustrating the net particle deflection angles of a particle at different fluid velocities with a fixed wave angle of 60°.

A similar study was conducted by fixing the wave angle and changing the fraction of normal velocity variation about the mean fluid velocity component. Either increasing the flow velocity with fixed acoustics or changing the acoustic radiation force on the particle with fixed flow velocity can generate this effect. FIG. 5 shows a graph generated with these parameters. As can be seen in the graph of FIG. 5, the particle deflection increases with increases in $\Delta V_N/V_N$ and reaches a maximum when $\Delta V_N/V_N=1.0$.

When $\Delta V_N/V_N=1.0$, the normal velocity reaches zero in the standing wave and the particle travels along the wave. For further clarification, with a constant velocity mixture approaching an acoustic standing wave oriented at an angle of 60° relative to the direction of mean flow of the mixture, any particle that is stopped in the normal direction by the standing wave radiation forces is deflected at an angle upwards of 60°, or travels parallel to the wave front. The particle that is only slowed down by the standing wave will be deflected at a constant angle away from the normal direction, or axial direction of the standing wave.

A universal solution for particle or cell deflection by angled acoustic waves was generated using a newly developed, non-dimensional parameter M. It is defined as follows:

$$M = \frac{C}{V}\frac{\pi}{3}\frac{r_p^2 \beta P_0^2 \varphi}{\mu \lambda V} \quad (5)$$

$$M = \frac{\Delta V_N}{V} \quad (6)$$

$$M \sim \frac{\text{Particle Radiation Force}}{\text{Viscous Drag Force}}$$

where C is the maximum normal velocity perturbation ($\Delta V_N$) from Equation 3 and V is the fluid free stream velocity. This non-dimensional parameter, M, is extremely important because it represents the ratio of acoustic radiation force on a particle to the viscous drag force on the particle. M is the key parameter for particle deflection by an angled standing wave. Both acoustic power and particle size are squared in the expression. This means they are the most dominant factors for determining particle deflection. An accurate expression for any particle deflection in an angled wave, in terms of M, can be obtained by solving particle movement with the normal wave exactly, and then transforming the results to the angled wave flowfield.

Figure 6:
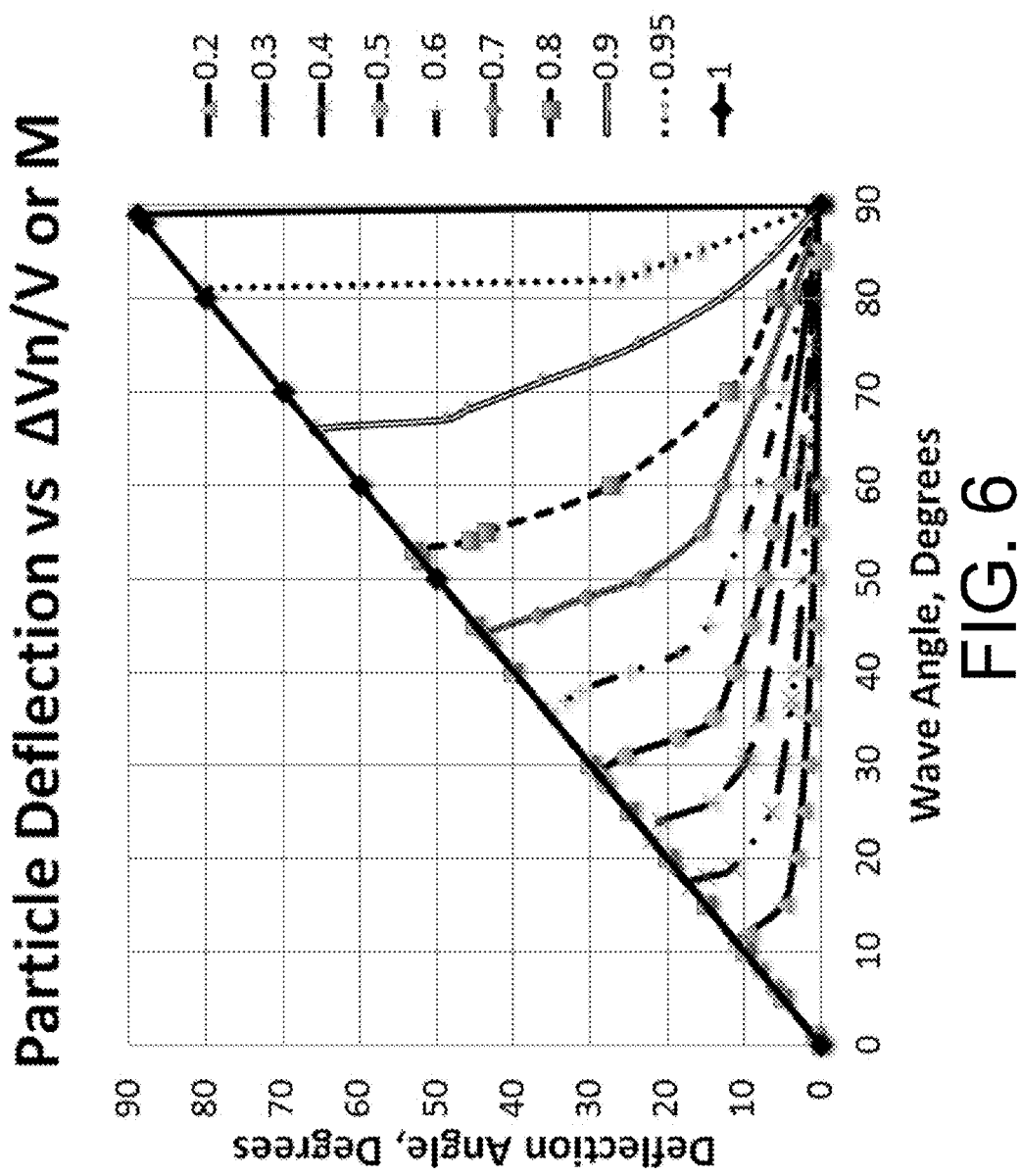
FIG. 6 represents universal operating characteristics of any angled wave acoustic chamber presenting particle or cell deflection versus wave angle for any operating parameter M.

Calculated particle deflection angles are presented in FIG. 6 versus wave angle and the non-dimensional deflection parameter M. All possible particle deflection angles are seen to fall on, or lie on curves below the 45-degree line as shown in FIG. 6. The forty-five degree line represents maximum particle deflections for any angled acoustic wave. The maximum deflections represent a particle deflection angle equal to the acoustic wave angle, and always fall on the forty-five degree line. Each M curve in FIG. 6 is seen to have a discontinuity near the maximum deflection value where the particle deflection jumps from the difference between the up and down deflection regions shown in FIG. 3, to the down deflection only. This steep gradient represents a change in the physical mode of the deflection process. This occurs when the radiation force in the downward deflection region reaches a value large enough to stop the particle motion through the wave, which is described in greater detail herein. The results show that particles flowing in a fluid suspension can be deflected down an acoustic standing wave of any strength, if the wave angle is small enough. The different M curves in FIG. 6 can represent the effects of power on particle deflection versus wave angle while particle size, fluid compressibility factor, acoustic wavelength, fluid viscosity, and fluid velocity are all held constant at the baseline condition. The baseline condition in FIG. 7 is at M=0.8 which represents: mixture free stream velocity, V=7.75× $10^{-4}$ m/sec; acoustic standing wave wavelength λ=7.4×$10^{-4}$ m; mixture viscosity, μ=1.0×$10^{-3}$ Pa-sec; contrast factor, X=0.12; mixture compressibility, β=4.06×$10^{-10}$ $m^2$/N; particle radius, r=3×$10^{-6}$ m; and acoustic pressure amplitude, Po=1.0 MPa.

The particle deflection curve presented in FIG. 6 for M=0.8 is for all wave angles. The wave angles are varied from zero to ninety degrees. The particle deflection, at any constant M value, becomes equal to the wave angle as the wave angle is increased. At this point, the particle is stopped from moving through the waves by the normal radiation forces, and moves along the wave front direction. The particle deflection reaches a maximum of 53.1°, for M=0.8, at a wave angle of 53.1°. At a wave angle of 55° with M=0.8, the particle deflection angle drops to 28°. At a wave angle of 60° with M=0.8, the particle deflection is 23°.

Figure 7:
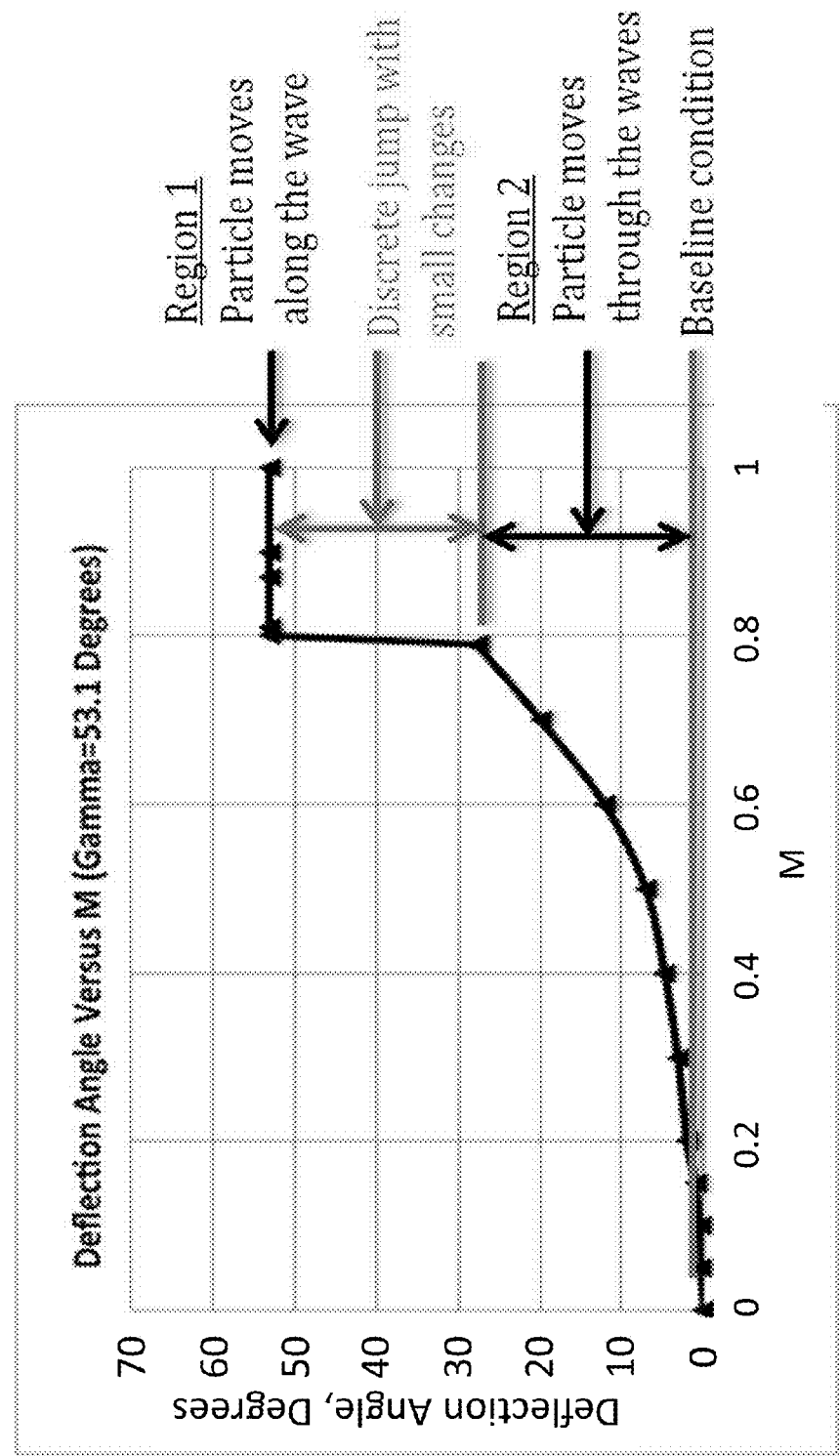
FIG. 7 represents a plot from FIG. 6 giving both the deflection angle versus M for a fixed wave angle, as well as defining the operating regions of such a system.

FIG. 7 presents the particle deflection variation with M that occurs through waves angled at 53.1°. M is varied from 0 to 1 in FIG. 7. The discontinuity in the deflection curve near maximum deflection is evident in the curve. The magnitude of the discontinuity increases with increasing M. This discontinuity is extremely useful, since it can allow for the separation of particles due to slight property differences. The differences could represent live versus dead cells, tagged versus untagged cells, mutated versus original cells, or even healthy versus unhealthy cells. Region 1 shown in FIG. 7 is where the acoustic radiation force is large enough to stop the particles from moving through the waves. The particles are seen to move parallel to the wave front and $\Delta\Theta_M=\gamma$ in Region 1. Theoretically, in Region 1, all the particles will be deflected down the wavefront in the first wave. In Region 2, the particles pass through all the waves, and get deflected down (for the right running wave shown) a constant angle, $\Delta\Theta_M$, which is significantly lower than γ. The particle net deflection in Region 2 is the difference between the downward deflection (particle slowed down by the radiation forces) and upward deflection regions (particle sped up by the radiation forces). Region 1 and Region 2 represent two different modes of operation. This discontinuity is extremely useful, since it could allow the separation of particles with very small size, stiffness, or density differences.

FIGS. 8-11 present particle trajectory computational results for yeast particles and CHO cells showing the effect on the particle deflection experienced under different particle/cell sizes and varied flow rates. In FIGS. 8-11, the shaded and lined area represents the angled acoustic standing wave. In this regard, the flow from right to left in FIGS. 8-11, and all of the particles/cells enter the angled acoustic standing wave at the same point on the left side of the right-running wave. The lines then represent the deflection trajectories of the different sized cells/particles and/or the cells/particles flowed at varied flow rates.

Figure 8:
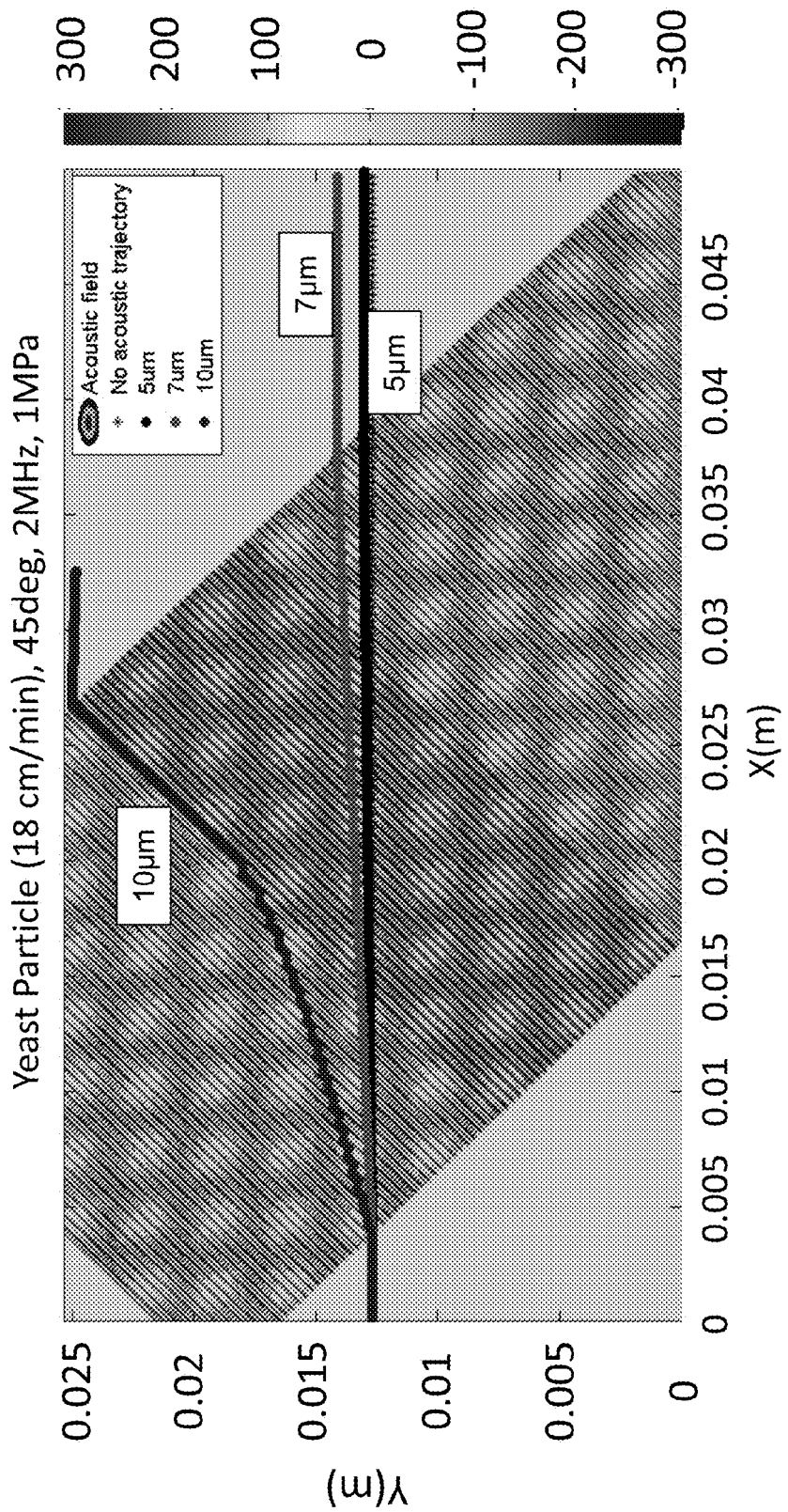
FIG. 8 illustrates particle trajectory computational results showing predicted particle deflections versus particle size for a yeast particle in a device operating at a flow velocity of 18 cm/min, at a frequency of 2 MHz, and at an acoustic pressure amplitude of 1 MPa, with an acoustic standing wave oriented at an angle of 45° relative to the direction of mean flow. Three lines are shown: the uppermost line represents a particle size of 10 µm, the middle line represents a particle size of 7 µm, and the lowermost line represents a particle size of 5 µm. The numbers on the right hand side represent particle axial acceleration in $(m^2/s)$.
Figure 10:
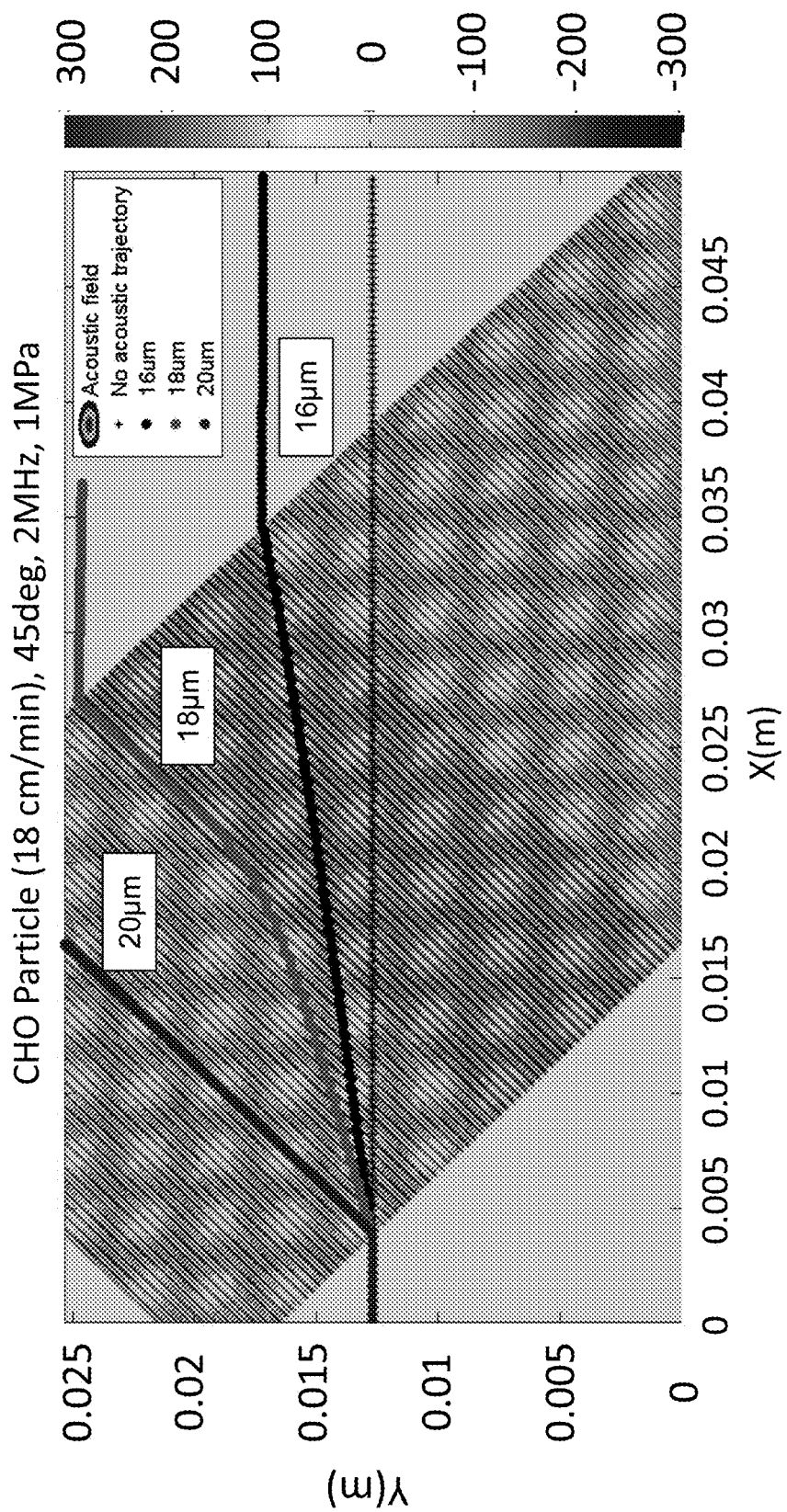
FIG. 10 illustrates particle trajectory computational results showing predicted particle deflections versus particle size for a Chinese hamster ovary (CHO) cell in a device operating at a flow velocity of 18 cm/min, at a frequency of 2 MHz, and at a pressure of 1 MPa, with an acoustic standing wave oriented at an angle of 45° relative to the direction of mean flow. Three lines are shown: the uppermost line represents a cell size of 20 µm, the middle line represents a cell size of 18 µm, and the lowermost line represents a cell size of 16 µm. The numbers on the right hand side represent particle axial acceleration in $(m^2/s)$.
Figure 11:
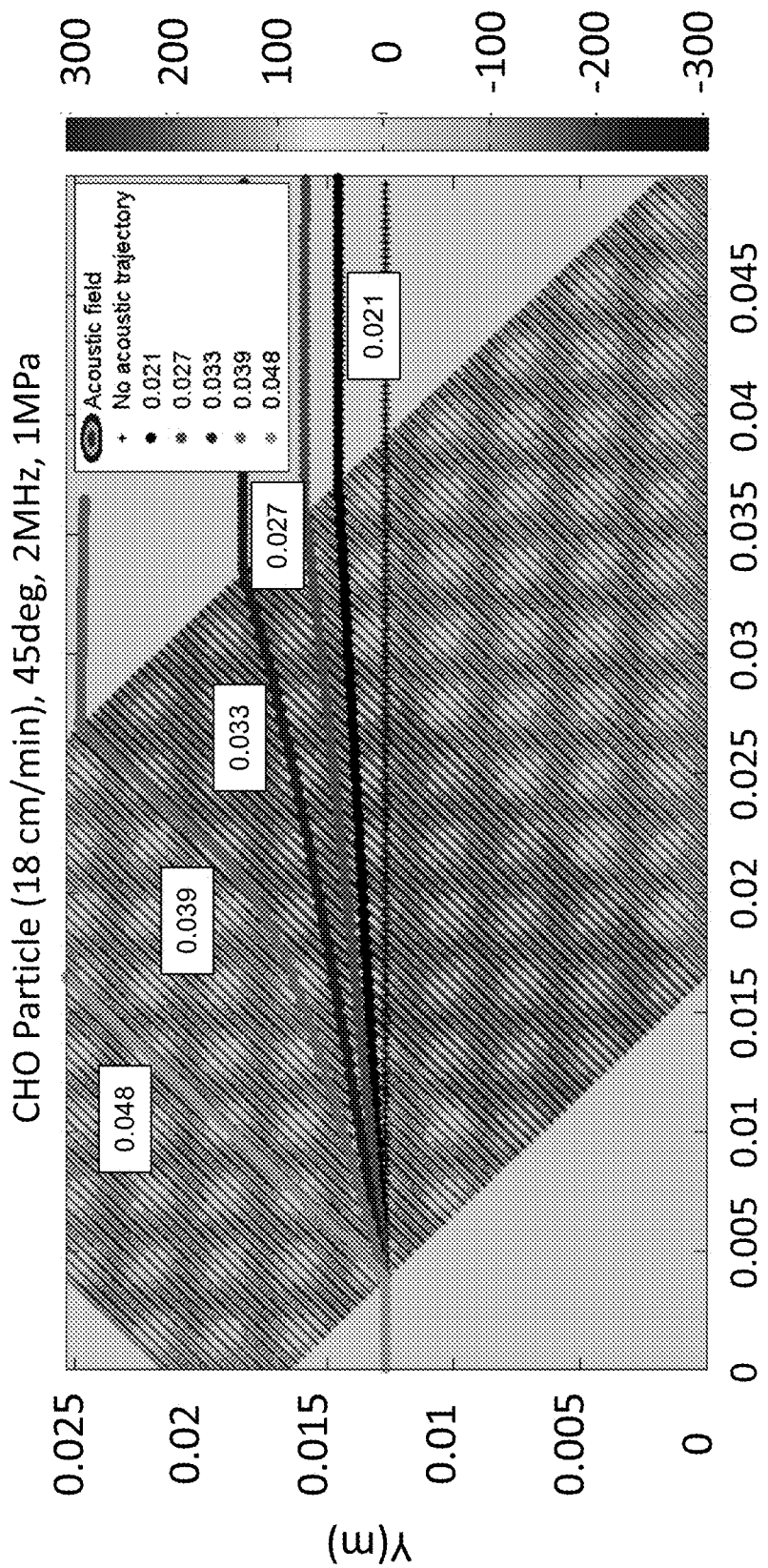
FIG. 11 illustrates particle trajectory computational results showing predicted particle deflections versus flow velocities for Chinese hamster ovary (CHO) cells having different contrast factors in a device operating at a flow velocity of 18 cm/min, at a frequency of 2 MHz, and at a pressure of 1 MPa, with an acoustic standing wave oriented at an angle of 45° relative to the direction of mean flow.

FIG. 8 presents particle trajectory computational results to further verify the physics of angled standing waves and the predictions presented. These results were obtained by numerically solving Equation 2 in its entirety and include inertial effects. Viscosity modifies inertial effects to generate a symmetrical perturbation velocity about the mean normal velocity component, to obtain a constant deflection as shown in FIG. 8.

FIG. 8 presents particle trajectory computational deflection results of different size yeast particles (i.e., CFD predicted particle deflection versus particle size). The smaller particles deflect less since they have lower magnitude radiation forces acting on them. In addition to varying the size of the particles, lower radiation forces can be generated in many different ways, as will be appreciated by those skilled in the art. As a result, angled standing waves can be used to separate or fractionate particles in suspension by size, density, speed of sound, and shape. This technique may allow live cells to be separated from dead cells, or even damaged cells from healthy cells. The deflection of the particle by the standing wave can also be controlled or amplified by the strength of the acoustic field, the angle of the acoustic field, the properties of the fluid, the three dimensionality of the standing wave, the frequency of the standing wave, the acoustic chamber shape, and the mixture flow velocity. As can be seen beginning from the left side of FIG. 8, particle deflection in the first few wavelengths can vary depending on the exact location where the particle enters the standing wave (referred to as a length effect). The viscosity damps this initial length effect out quickly. The CFD results verify the constant angle of deflection across a large number of waves, as presented above. Based on the theory presented, the deflection of the particle will be a function of the non-dimensional deflection parameter, M.

Figure 9:
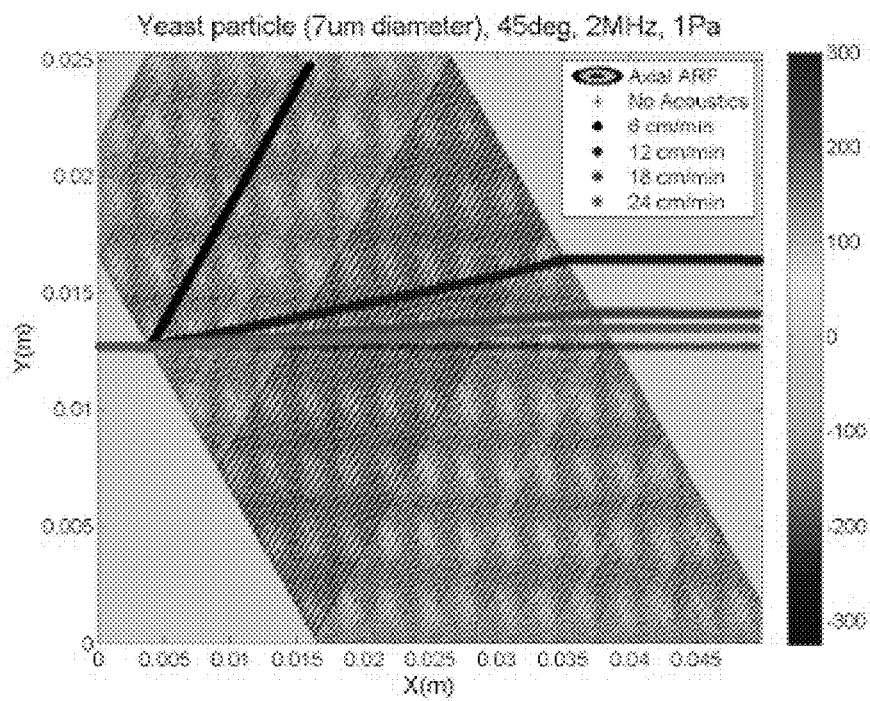
FIG. 9 illustrates particle trajectory computational results showing predicted particle deflections versus flow velocities for a 7 micron yeast particle in a device operating at flow velocities of 6 cm/min, 12 cm/min, 18 cm/min, and 24 cm/min, at a frequency of 2 MHz, and at an acoustic pressure amplitude of 1 MPa, with an acoustic standing wave oriented at an angle of 45° relative to the direction of mean flow.

Turning now to FIG. 9, particle trajectory computational results are presented, which verify the effects of normal velocity variation on the particle deflection resulting from a mixture flowing into an acoustic standing wave at an angle of 45 degrees (i.e., predicted particle deflection versus flow velocity). As the flow velocity increases, $\Delta V_N/V_N$ decreases and particle deflection angles are shown to decrease. This effect provides another means to increase the ability to detect minor differences in particle properties based on this procedure. As the flow velocity was increased (from about 0 cm/min to about 24 cm/min in FIG. 9), $\Delta V_n/V_n$ decreased and particle deflection angles were shown to decrease. This effect provides another means to increase the ability to detect minor differences in particle properties using the methods and devices according to the present disclosure.

The particle trajectory computational results verify that particles in a fluid flowing through an acoustic standing wave, with the acoustic standing wave oriented at an angle relative to the fluid flow with a constant velocity, will be deflected a constant angle from the fluid flow direction. It is expected that this angular deflection phenomena will have a short (few waves), initial development region where viscous dissipation will force any non-symmetrical perturbation velocity distribution generated by either inertia effects, or the location at which the particle enters the standing wave, to be symmetrical about the fluid mean flow. The flow angle deflection can vary in this initial region, but the region is so short that the result is insignificant to the overall particle deflection for a macro-scale system, such as those systems specifically disclosed herein.

The computational framework discussed above can easily be extended in three dimensions. For small cells or emulsions the drag force $F_V$ can be expressed as:

$$\vec{F}_V = 4\pi\mu_f R_p (\vec{U}_f - \vec{U}_p) \left[ \frac{1 + \frac{3}{2}\hat{\mu}}{1 + \hat{\mu}} \right],$$

where $U_f$ and $U_p$ are the fluid and cell velocity, $R_p$ is the particle radius, $\mu_f$ and $\mu_p$ are the dynamic viscosity of the fluid and the cells, and $\hat{\mu} = \mu_p/\mu_f$ is the ratio of dynamic viscosities. The gravity/buoyancy force $F_B$ is expressed as:

$$\vec{F}_B = \frac{4}{3}\pi R_p^3 (\rho_f - \rho_p)\vec{g}.$$

For small particles, this force can typically be neglected as it is several orders of magnitude smaller than the other force components, making this disclosure essentially gravity independent. The primary acoustic radiation force FA has been defined before.

A general particle trajectory model then becomes:

$$m_p \frac{d^2\vec{x}_p}{dt^2} = \vec{F}_V + \vec{F}_A + \vec{F}_B$$

where $m_p$ is the mass of the particle, $F_V$ is the drag force of the fluid on the particle, $F_R$ is the acoustic radiation force, and $F_B$ is the gravity/buoyancy force which can typically be neglected. These equations can then be integrated to find the particle trajectories for a given fluid flow, particle, and initial conditions.

In another embodiment, the angled acoustic standing wave field can be oriented such that it has both a polar and azimuthal angle with respect to the fluid flow, which then would result in particle deflections to a corner of the fluid channel.

Figure 12:
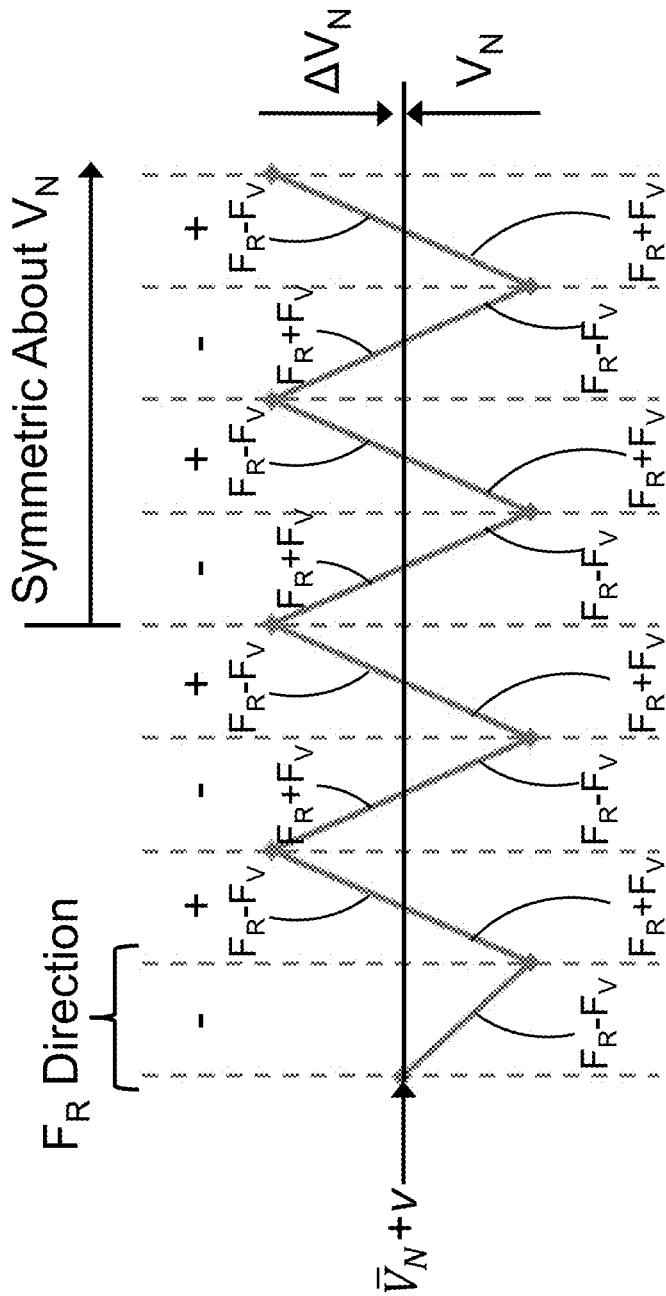
FIG. 12 illustrates the initial, or development length region, for a particle entering an acoustic standing wave at the start of a negative force region.
Figure 13:
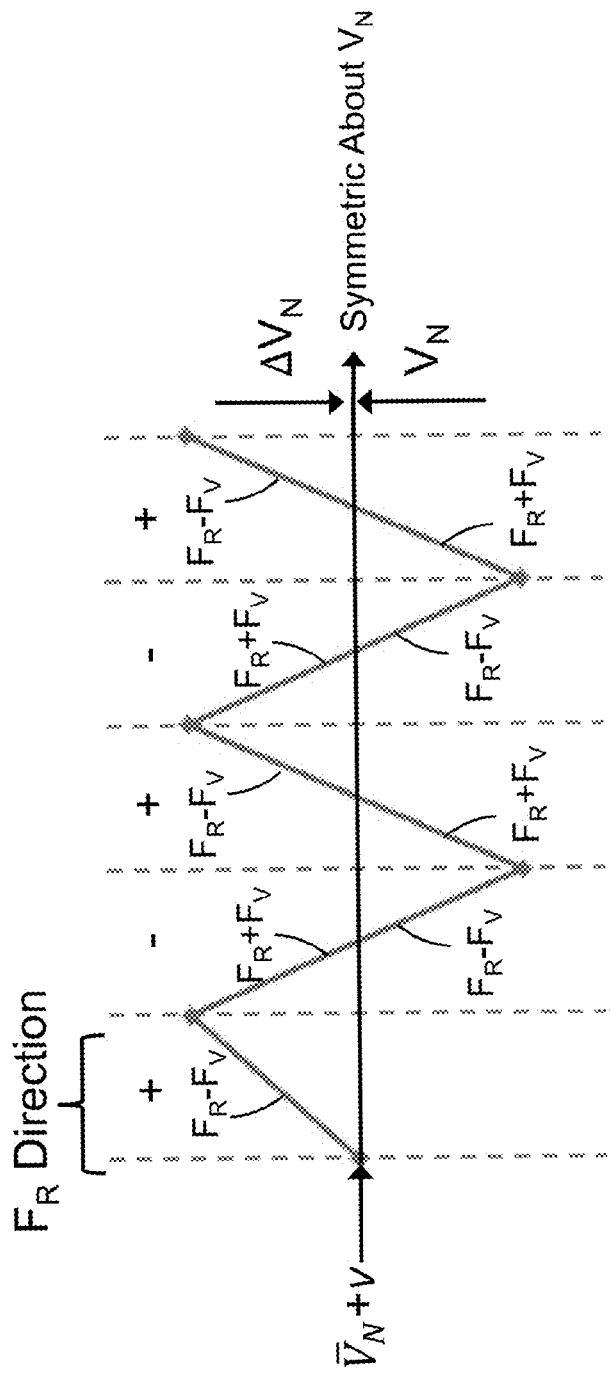
FIG. 13 illustrates the initial, or development length region, for a particle entering an acoustic standing wave at the start of a positive force region.

FIG. 12 and FIG. 13 schematically present the initial, or development length region, for a particle that enters a standing wave at different locations. The pluses and minuses represent acoustic radiation force directions, from Equation 1, that slow or speed up a particle, respectively. A zero radiation force occurs at each dashed vertical line shown. The force varies as a sine wave between these dashed lines. FIG. 12 represents a particle entering the wave system at the start of a negative force region. The solid staggered lines represent residual perturbation velocities generated due to particle inertia. As seen in FIG. 12, the particle is still moving down due to inertia when the radiation force approaches zero at the second vertical dashed line. This effect is exaggerated to explain the physics present. In most cases, inertia effects can be neglected from a macro sense. A similar effect is shown in FIG. 13, but in the opposite direction. FIG. 13 represents a particle entering the wave system at the start of a positive force region. Again, the solid staggered lines represent residual perturbation velocities generated due to particle inertia. These inertial effects generate different force regions where the viscous and radiation forces add or subtract as shown by $F_R+F_V$ and $F_R-F_V$. In this manner, these schematics in FIG. 12 and FIG. 13 show how these different flow regions force the perturbation velocity to be repetitive and symmetric about the mean flow velocity. This symmetrical perturbation about the mean velocity results in a constant angle deflection of the particle. This effect distinguishes the macro devices and systems disclosed herein from previous MEMS work, which operated in the development region and which can have many different deflections of the same particle. Additionally, the processes and devices disclosed herein use bulk acoustic standing waves, not surface waves used previously in other work.

It is contemplated that a specific velocity profile can be used to enhance particle diffraction. For example, the flow velocity may decrease with height (i.e., the flow rate is progressively lower at the top of the flow chamber than at the bottom). The resulting particle deflections by the angled standing wave would thereby be amplified because the percent normal velocity variations would increase dramatically with height because of the incoming velocity profile. As will be appreciated by those skilled in the art, coupling the velocity profile to the angle of the standing wave can be tuned to any specific, desired fractionation output. In this regard, the velocity profiles of the incoming mixture can be generated by any suitable means, including screens, ducts, plenums, or diffusers.

Figure 14:
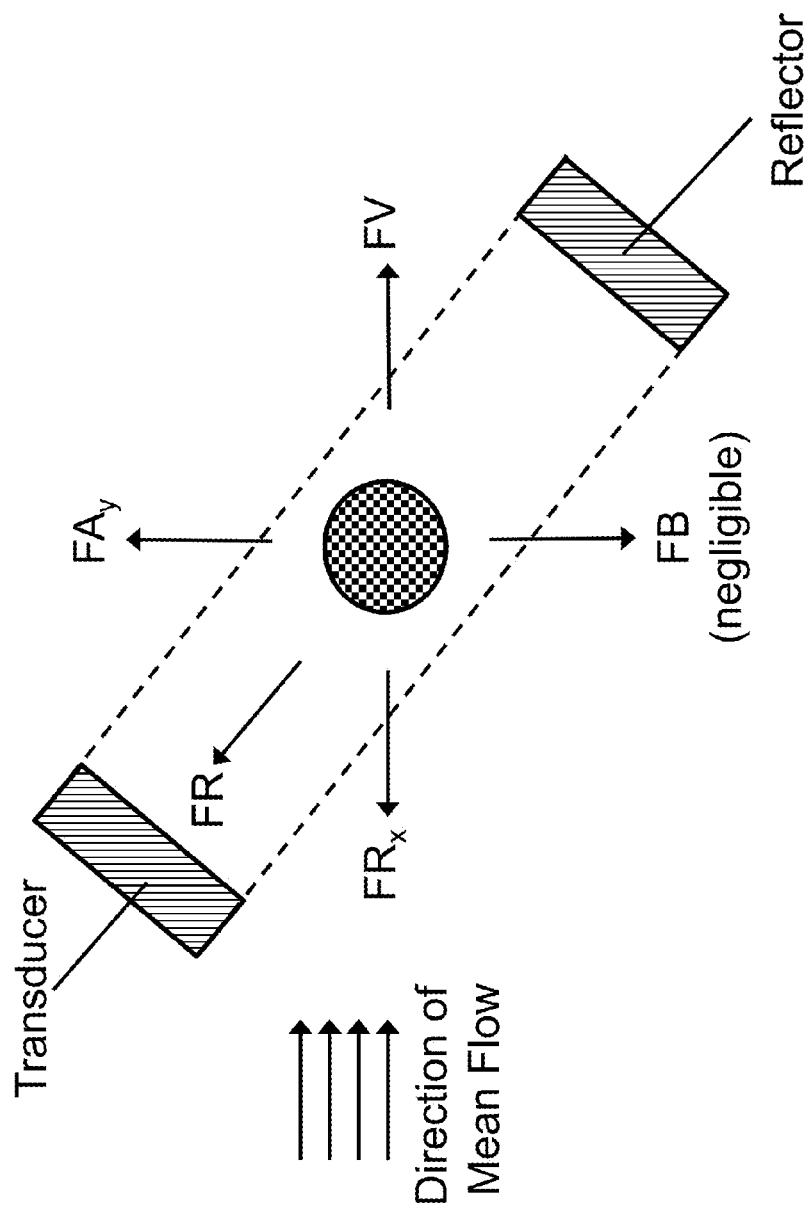
FIG. 14 illustrates a free body diagram showing the forces experienced by a particle suspended in an acoustic standing wave that is oriented at an angle relative to a direction of mean flow through a flow chamber.

As another means of explaining many of the same concepts presented above, FIG. 14 provides a free body diagram showing the forces experienced by a particle suspended in an acoustic standing wave that is oriented at an angle relative to a direction of mean flow through a flow chamber. In FIG. 14, FV represents the drag force in the direction of mean flow, FB represents the force due to gravity/buoyancy forces, which is generally negligible, and FR represents the acoustic force in the direction of the acoustic standing wave, which has force components in the x and y directions. It is to be understood that reliance on gravitational or buoyancy forces for settling or rising is not necessary for efficient separation using the devices and methods according to the present disclosure Conventional macro-scale ultrasonic separators use acoustic standing waves to generate tightly packed clusters of suspended fluid or particulate, which continuously drops out of a flowing fluid mixture. Such conventional macro-scale separators generally operate with flow Reynolds numbers less than 50, particle concentrations up to 20%, ultrasonic standing wave field frequencies of 1-3 MHz, and acoustic pressure amplitudes of about 1 MPa. Although these systems are effective, their flow rates are limited by the strength of the lateral acoustic radiation forces. Consequently, such systems are undesirable for applications requiring high flow rates. For example, as explained above, applications in the food and beverage industry require flow rates up to ten times faster than these conventional separators can support.

The present disclosure relates to acoustophoretic devices that employ angled ultrasonic acoustic standing waves that are angled relative to the flow direction and, as a result, deflect cells, particulates, or a second fluid in a host fluid stream. The acoustophoresis devices and methods disclosed herein utilize the axial radiation forces of a multi-dimensional acoustic standing wave. The axial radiation forces in a standing wave can be significantly higher than the lateral forces, though they are within an order of magnitude. Thus, significant performance improvements can be generated by using axial, rather than lateral, radiation forces to collect particles or cells in a fluid suspension.

Figure 15:
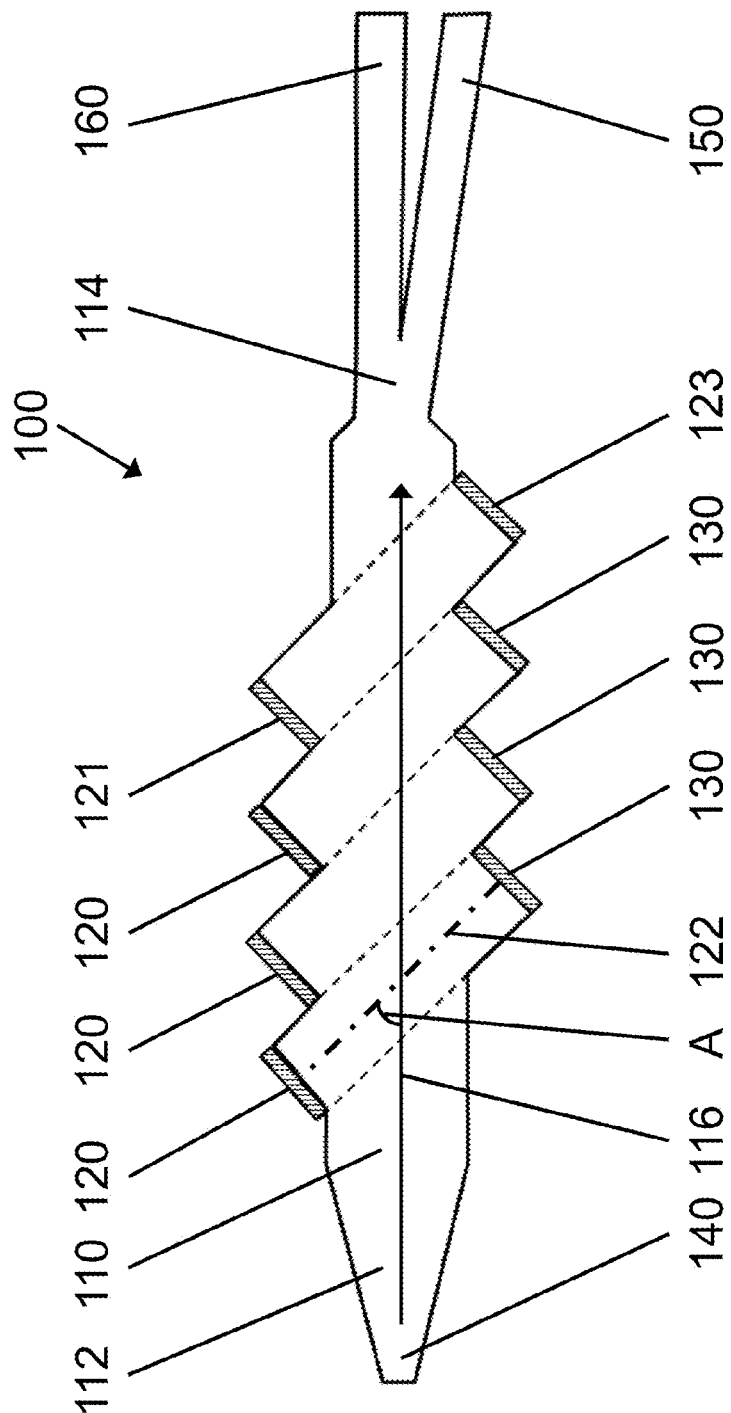
FIG. 15 illustrates an exemplary acoustophoresis device according to a first embodiment of the present disclosure.

FIG. 15 presents a first exemplary embodiment of such an axial force, macro-scale acoustophoretic device designated generally as 100. The acoustophoretic device 100 generally operates so as to use the axial radiation forces from an angled acoustic standing wave oriented at an angle relative to the direction of mean flow through the device 100. The acoustophoretic device 100 depicted in FIG. 15 includes a flow chamber 110, an ultrasonic transducer 120, and a reflector 130.

The flow chamber 110 is the region of the device 100 through which is flowed an initial mixture of the host fluid and a second fluid or particulate and defines a direction of mean flow therethrough. The direction of mean flow is designated generally as 116 in FIG. 15. In particular embodiments, the initial mixture of the host fluid and at least one of the second fluid or particulate is flowed through the device 100 at a flow rate of about 400 mL/min to about 700 mL/min. The flow chamber is formed by a sidewall, and has a cross section of 1 inch by 1 inch.

In certain embodiments, the initial mixture of the host fluid and second fluid or particulate enters the flow chamber 110 through an inlet 140. As shown in FIG. 15, the inlet 140 is generally located at a first end 112 of the flow chamber 110 (i.e., upstream of the ultrasonic transducer 120 and reflector 130).

In particular embodiments, such as that shown in FIG. 15, the device 100 also includes a clarified fluid outlet 150, which is generally located at a second end 114 of the flow chamber 110. As seen in FIG. 15, the second end 114 of the flow chamber 110 is opposite the first end 112 of the flow chamber 110 (i.e., the second end 114 is downstream of the ultrasonic transducer 120 and reflector 130). In this way, the inlet 140 permits fluid ingress into the device 100, and the clarified fluid outlet 150 permits fluid egress from the device 100.

The device 100 further includes at least one ultrasonic transducer 120. The ultrasonic transducer 120 may generally be located within or on the sidewall of the flow chamber 110, and the sidewall is shaped to hold the transducer at an acute angle relative to the direction of mean flow 116. In FIG. 15, the device 100 includes four ultrasonic transducers 120. In this regard, it is to be understood that the device 100 includes at least one ultrasonic transducer, but may otherwise include as many or as few transducers as is desired for a particular application. Each ultrasonic transducer 120 is driven by a voltage signal to create an angled acoustic standing wave 122 in the flow chamber 110 between the ultrasonic transducer 120 and a reflector 130 located on the sidewall on an opposite side of the flow chamber 110 from the transducer 120. In particular embodiments, the voltage signal sent to the ultrasonic transducer 120 is from about 25 V to about 50 V. The ultrasonic transducer 120 is generally operated at a frequency of about 2 MHz to about 3 MHz. The angled acoustic standing wave 122 created by the ultrasonic transducer 120 results in an acoustic radiation force having an axial force component (i.e., in the direction of the standing wave, between the transducer and the reflector, angled relative to the flow direction). It is to be understood that the angled acoustic standing waves utilized herein can be generated between a transducer 120 and a reflector 130 such as is shown in the first, leftmost acoustic chamber depicted in FIG. 15, or can be generated between two transducers positioned opposite one another, such as between transducer 121 and transducer 123, as depicted in the last, rightmost acoustic chamber depicted in FIG. 15.

Due to the orientation of the ultrasonic transducer 110 relative to the flow chamber 110, the angled acoustic standing wave 122 created by the ultrasonic transducer 110 is oriented at an angle A relative to the direction of mean flow 116 through the flow chamber 110. As shown in FIG. 13, the angle A at which the angled acoustic standing wave 122 is oriented relative to the direction of mean flow 116 through the flow chamber 110 is generally an acute angle (i.e., less than 90°). In certain embodiments, the angle A at which the angled acoustic standing wave 122 is oriented relative to the direction of mean flow 116 through the flow chamber 110 is about 20° to about 70°. In particular, it has been found that maximum deflection of particulates entrained in the host fluid occurs at an angle of about 60° to about 70°.

As previously explained, in certain embodiments the device 100 includes a plurality of ultrasonic transducers. In the embodiment shown in FIG. 15, all four of the transducers 120 have the same angle relative to the direction of mean flow 116 through the flow chamber 110. It is also contemplated that when a plurality of transducers are provided, the transducers can create angled acoustic standing waves that are oriented at different angles relative to the direction of mean flow 116 through the flow chamber 110. For example, each transducer may create angled acoustic standing waves in the flow chamber 100 oriented at an angle of about 20° to about 70° relative to the direction of mean flow 116 through the flow chamber 110, which angle may be the same or different than the other transducers present within the device 100. Moreover, each transducer can be operated so as to create different standing waves (e.g., of different frequencies) in the flow chamber.

In particular embodiments, the acoustophoresis device further includes a concentrate outlet 160. The concentrate outlet 160 is also located at the second end 114 of the flow chamber 110, adjacent to but spaced apart from the clarified fluid outlet 150. The concentrate outlet 160 and the clarified fluid outlet 150 have flow paths that are angled apart from each other at a relatively shallow acute angle. In operation, the transducers 120 cause desired particles to be deflected into the concentrate outlet 160, permitting clarified fluid to flow out through the clarified fluid outlet 150. The clarified fluid has a relatively lower concentration of the particles compared to the fluid entering through inlet 140. Please note that although here the concentrate outlet 160 is shown above the clarified fluid outlet 150, their locations can be reversed if desired.

In the device of FIG. 15, the M operation point can be set for the device to operate in Region 1 described with respect to FIG. 7. As a result, the particle, cell, or second fluid is deflected down the wave angle as shown. Some particles may collide and/or pass through several waves, but eventually most particles will be deflected down toward the lower chamber wall. In this way, the concentrate outlet 160 will collect concentrated mixture, while the clarified fluid outlet 150 will collect clarified fluid. In this manner, the device depicted in FIG. 15 will provide high speed separation, clarification, or concentration of the mixture.

Figure 16:
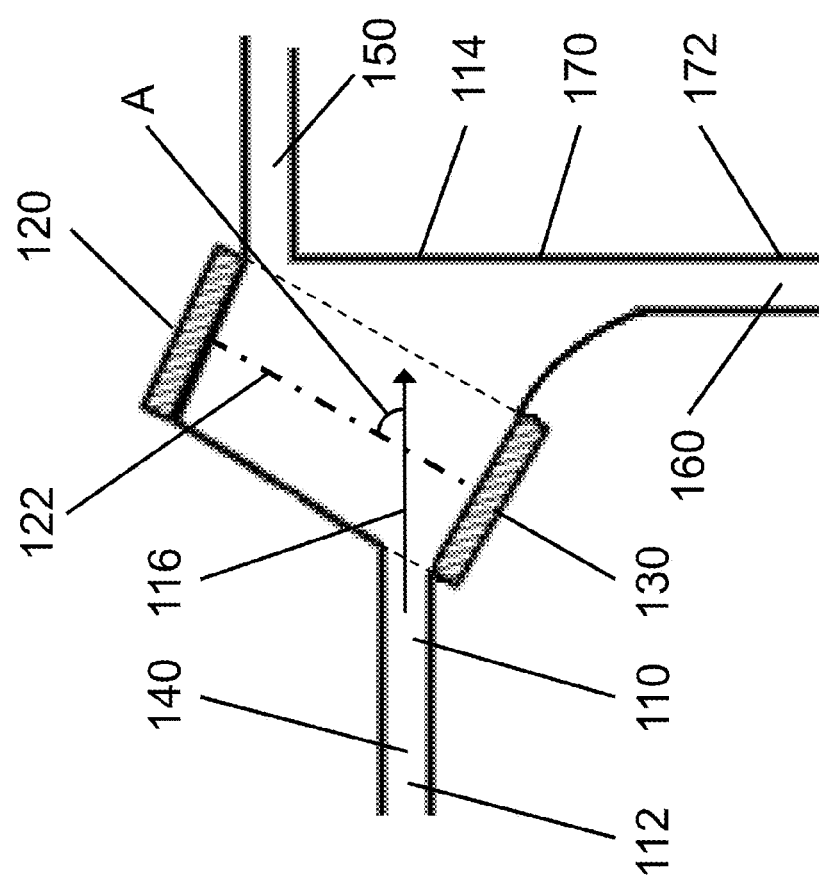
FIG. 16 illustrates an exemplary acoustophoresis device according to a second embodiment of the present disclosure.

In certain other embodiments, such as that shown in FIG. 16, the device 100 includes a deflection wall 170 below the clarified fluid outlet 150. In such embodiments, the concentrate outlet 160 is generally located at a lower end 172 of the deflection wall 170. In the embodiment shown in FIG. 14, the deflection wall extends substantially perpendicular to the direction of mean flow 116 through the flow chamber 100. In other embodiments, the deflection wall 140 can be angled or tilted relative to the mean direction of fluid flow. In the embodiment of the device 100 depicted in FIG. 16, the deflection wall 170 further serves as the second end 114 of the flow chamber 110, opposite the first end 112 of the flow chamber 110, which is generally defined by the inlet 140.

As explained above, the angled acoustic standing wave 122 results in an acoustic radiation force having an axial force component (i.e., in the direction of the standing wave, between the transducer and the reflector, angled relative to the flow direction). The axial force component deflects the second fluid or particulate into the deflection wall, as explained in great detail herein. Upon being deflected, the second fluid or particulate can then be collected from the device 100. As will be appreciated by those skilled in the art, the second fluid or particulate may be collected from the device by any suitable means, such as via the concentrate outlet 160 after deflection into the deflection wall 170. In particular embodiments, the second fluid or particulate is collected from the device 100 via the concentrate outlet 160 at a draw rate of about 200 to about 300 mL/min. While the transducers 120 are depicted at the top end of the flow chamber 110 (i.e., above the reflectors 130), it is to be understood that their locations can be reversed, such that the reflector 130 is located above the transducer 120. It is specifically contemplated, for example, that the device of FIG. 16 could be inverted, such that the reflector 130 is located at an upper end of the device and the transducer 120 is located at a lower end of the device. The device could then be operated so as to deflect particles in a host fluid flowing therethrough upward in the direction of the angled acoustic standing wave (i.e., upward toward the reflector 130) and to the concentrate outlet 160, which can be located at the upper end of the device (e.g., where the clarified fluid outlet 150 is located in FIG. 16). Resultantly, the clarified fluid outlet 150 could be located at a lower end of the device (e.g., where the concentrate outlet 160 is located in FIG. 16), and the deflection wall 170 could be repositioned as necessary to achieve the desired deflection.

Figure 17:
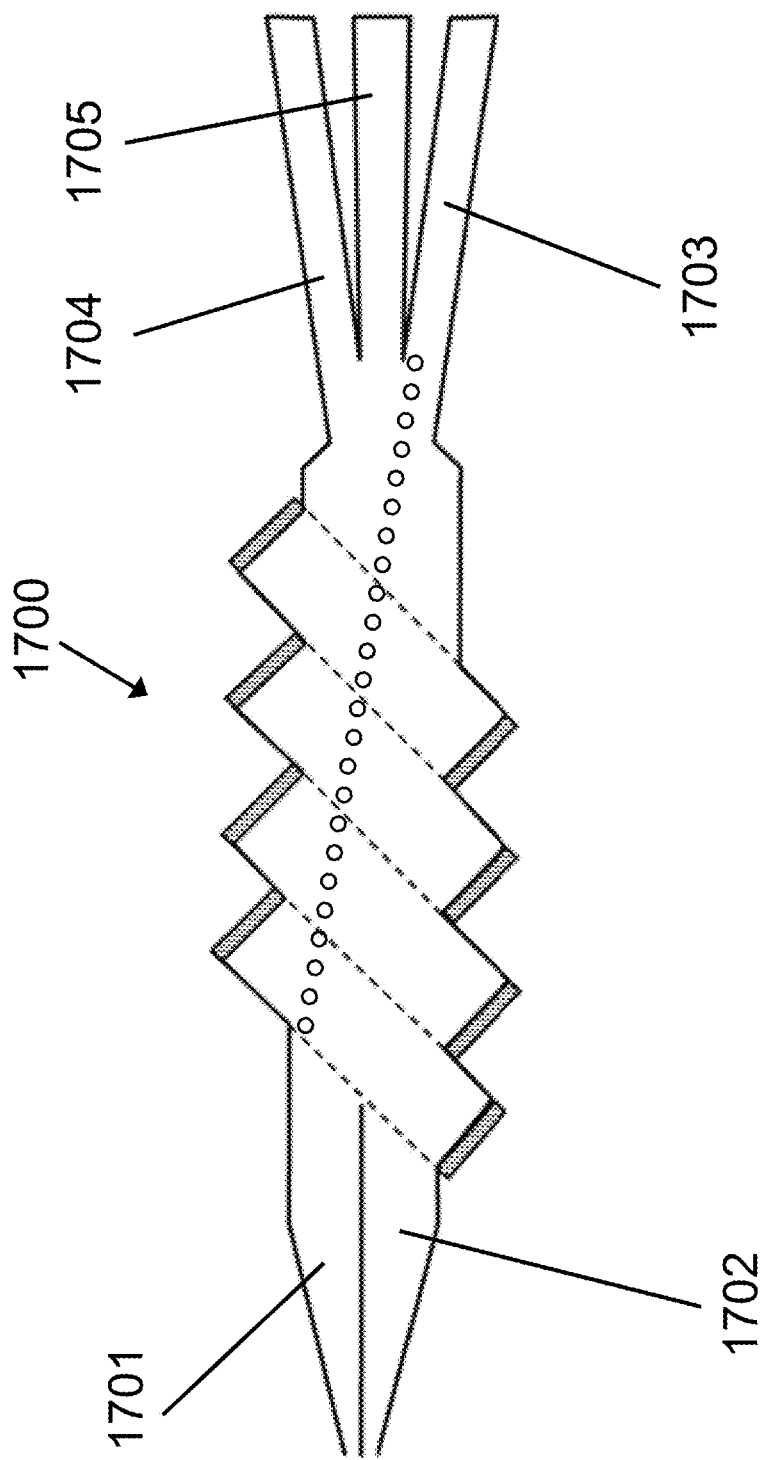
FIG. 17 illustrates an exemplary acoustophoresis device according to a third embodiment of the present disclosure.

In certain other embodiments, such as that shown in FIG. 17, a device 1700 according to the present disclosure may include one or more inlet ducts and one or more outlet ducts from the flow chamber. As can be seen, device 1700 is substantially similar to device 100 of FIG. 15, except as otherwise explained herein. For example, the device 1700 in FIG. 17 includes two inlet ducts and three outlet ducts. An initial mixture of a host fluid and at least one of a second fluid, cell, or particulate flows into the angled waves through an upper inlet duct 1701. A cell wash flows into the device via a lower inlet duct 1702. The angled wave is designed to operate at an M that generates the Region 1 process described above with reference to FIG. 7. As a result, the particles/cells are deflected along the wave angle as shown. The cells/particles pass from the mixture flow, through the wash flow, and concentrate in a lower duct exit 1703. The host fluid of the mixture primarily leaves the chamber through an upper exit duct 1704. The wash fluid primarily exits the chamber through a middle duct exit 1705. In this manner, particles/cells in a mixture can be isolated, washed, and concentrated in a single process. It is further contemplated that any of these steps could also be done separately through a different angled wave process, where the M operation point is set for the system to operate in Region 1 described above with reference to FIG. 7.

In certain other embodiments, the initial mixture of a host fluid and at least one of a second fluid, cell, or particulate can be flowed through a device according to the present disclosure with M set to operate the device either in Region 2, or in the steep gradient region described above with reference to FIG. 7. If operating in Region 2, multiple angled transducer-reflector pairs arranged in series may be necessary, such as is shown in device 100 of FIG. 15, with multiple outlets. In this mode, the different particles are deflected at different angles and the device fractionates many particles based on property differences. The same device can be operated with at least two outlets and with an M such that it is in the steep gradient region between 1 and 2, as described above with reference to FIG. 7. In this operation mode, very small differences will cause the particle to enter different outlets and the device can be operated as a property differentiator, such as by differentiating between live cells versus dead cells.

Figure 18:
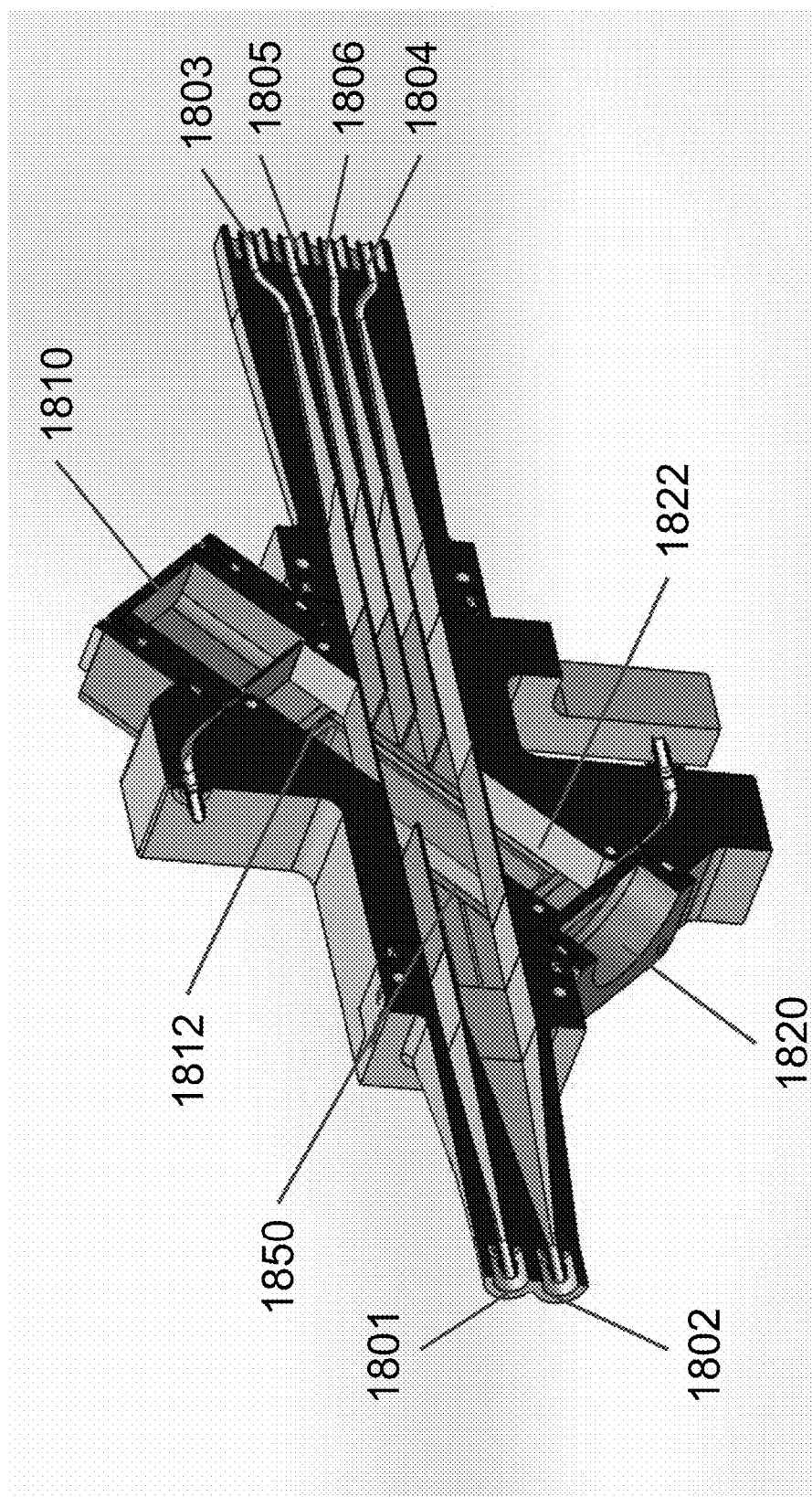
FIG. 18 illustrates an exemplary acoustophoresis device according to a fourth embodiment of the present disclosure.

As previously explained, the acoustophoresis devices according to the present disclosure can be used for various purposes, including cell washing, cell concentration or cell fractionation. FIG. 18 depicts a cross-sectional view of one such embodiment of a device according to the present disclosure including at least two inlets and at least two outlets. The device in FIG. 18 is depicted with two inlets 1801, 1802 and four outlets 1803, 1804, 1805, 1806. The first inlet 1801 can be of any suitable size and shape and is generally used as the inlet through which a mixture of a host fluid and at least one of a second fluid, cell, or particulate is introduced to the device. The second inlet 1802 can likewise be of any suitable size and shape and may have a cross-sectional width that is greater than a cross-sectional width of the first inlet 1801, such as is shown in FIG. 18. The first inlet 1801 is located above the second inlet 1802. The second inlet 1802 generally serves as the inlet through which a wash fluid can be introduced into the device. Alternatively, the second inlet 1802 can be used to carry another host fluid containing cells or particulates therein that can be the same or different than the first host fluid, with the cells or particulates having the same or different properties as one another.

The device further includes cavities 1810, 1820 in which transducers/reflectors can be located. As explained herein, the device can include one transducer and one reflector or two opposing transducers to create the angled acoustic standing wave. For example, cavity 1810 could hold a transducer and cavity 1820 could hold a reflector, cavity 1810 could hold a reflector and cavity 1820 could hold a transducer, or both cavity 1810 and 1820 could hold transducers. As can be further seen from FIG. 18, the cavities 1810, 1820 can be separated from the flow chamber by secondary chambers 1812 and 1822, respectively. In this way, secondary chamber 1812 separates cavity 1810 from the flow chamber 1850 and secondary chamber 1822 separates cavity 1820 from the flow chamber. The secondary chambers 1812, 1822 are generally filled with a fluid (e.g., water) or gel that is acoustically transparent, such that the transducer(s) and/or reflector located in cavities 1810 and 1820 are capable of generating an angled acoustic standing wave therebetween.

The device includes outlets 1803, 1804, 1805, and 1806. The uppermost outlet 1803 generally serves as a clarified fluid outlet through which the host fluid, which has been clarified of cells or particulates, flows out of the device. The middle outlets, outlets 1805 and 1806 can be used to recover a wash fluid that is used in the device. Alternatively, it is to be understood that the wash fluid could be removed via the same outlet as the host fluid, such as any of outlets 1803, 1805, and 1806. Finally, lowermost outlet 1804 can be used to remove the second fluid, cell, or particulate from the device after being deflected toward outlet 1804 by the angled acoustic standing wave. The uppermost outlet 1803 is above the middle outlets 1805, 1806, and the lowermost outlet 1804 is below the middle outlets 1805, 1806. As will be appreciated by those skilled in the art, any of the outlets can be uses to remove any fluid or material therefrom. For example, depending on the particular application and orientation of the device, an of the outlets can be used to remove a host fluid, a wash fluid, or a second fluid, cell, or particulate from the device. Put another way, any outlet can be used for any desired output.

Figure 19:
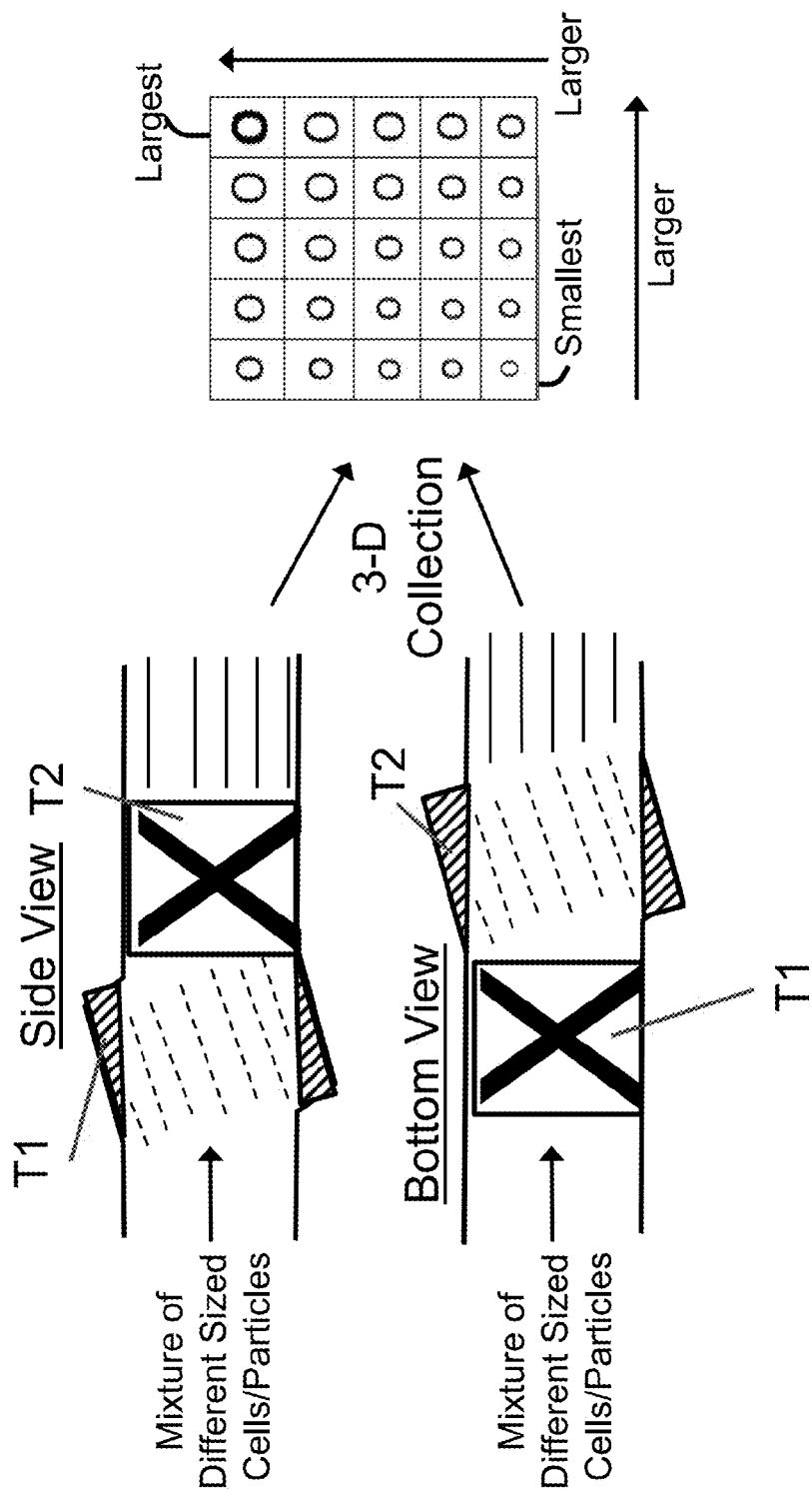
FIG. 19 illustrates an exemplary acoustophoresis device according to a fifth embodiment of the present disclosure.

In one embodiment, such as the embodiment of the acoustophoresis device shown in FIG. 19, the angled wave field can be a combination of two or more angled wave fields designed to generate three-dimensional displacement of the particles with respect to the fluid direction. Such a field can be generated by arranging two transducers in series and tilting the transducers such that the angled acoustic standing waves generated by each individual transducer are not parallel to one another. This arrangement is depicted in FIG. 19, in which transducer T1 is arranged in series with transducer T2 and arranged such that they are angled 90° from one another. The system would operate at an M required for Region 2 operation. As such, all the larger particles would move more to the top of the duct in the side view as a result of the first angled wave system. All the particles would move to the right of the duct as a result of the second angled wave in series, and the net results of the two wave systems in series are shown in the view from the exit plane as the 3D particle collection on the right side of FIG. 19.

Figure 20:
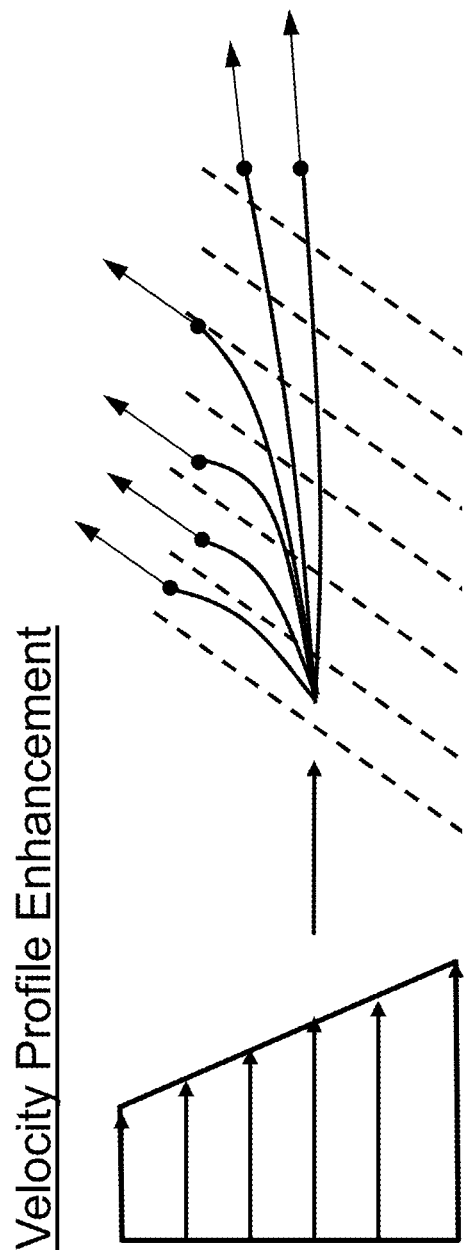
FIG. 20 illustrates a generated flow profile in which the flow rate is higher at the bottom of the angled acoustic standing wave than at the top thereof.

In certain other embodiments, such as that shown in FIG. 20, the angled wave field separation effect can be combined with a generated flow profile, at the acoustic chamber entrance, specifically designed to enhance particle separation, or fractionation. The decrease in velocity with height (i.e., the velocity is lower at the top of the angled acoustic standing wave than at the bottom thereof), as shown in FIG. 20, will increase M with height increasing the deflection variation of a particle with height. Such flow profiles can be obtained using duct wall contouring, screens, obstructions, valving or other flow manipulations.

Some further explanation of the ultrasonic transducers used in the devices, systems, and methods of the present disclosure may be helpful as well. In this regard, the transducers use a piezoelectric crystal, usually made of PZT-8 (lead zirconate titanate). Such crystals may have a 1 inch diameter and a nominal 2 MHz resonance frequency, and may also be of a larger size. Each ultrasonic transducer module can have only one crystal, or can have multiple crystals that each act as a separate ultrasonic transducer and are either controlled by one or multiple amplifiers. The crystals can be square, rectangular, irregular polygon, or generally of any arbitrary shape. The transducer(s) is/are used to create a pressure field in the standing wave direction (axial), namely axial forces that deflect particles in the host fluid out of the pressure field.

Figure 21:
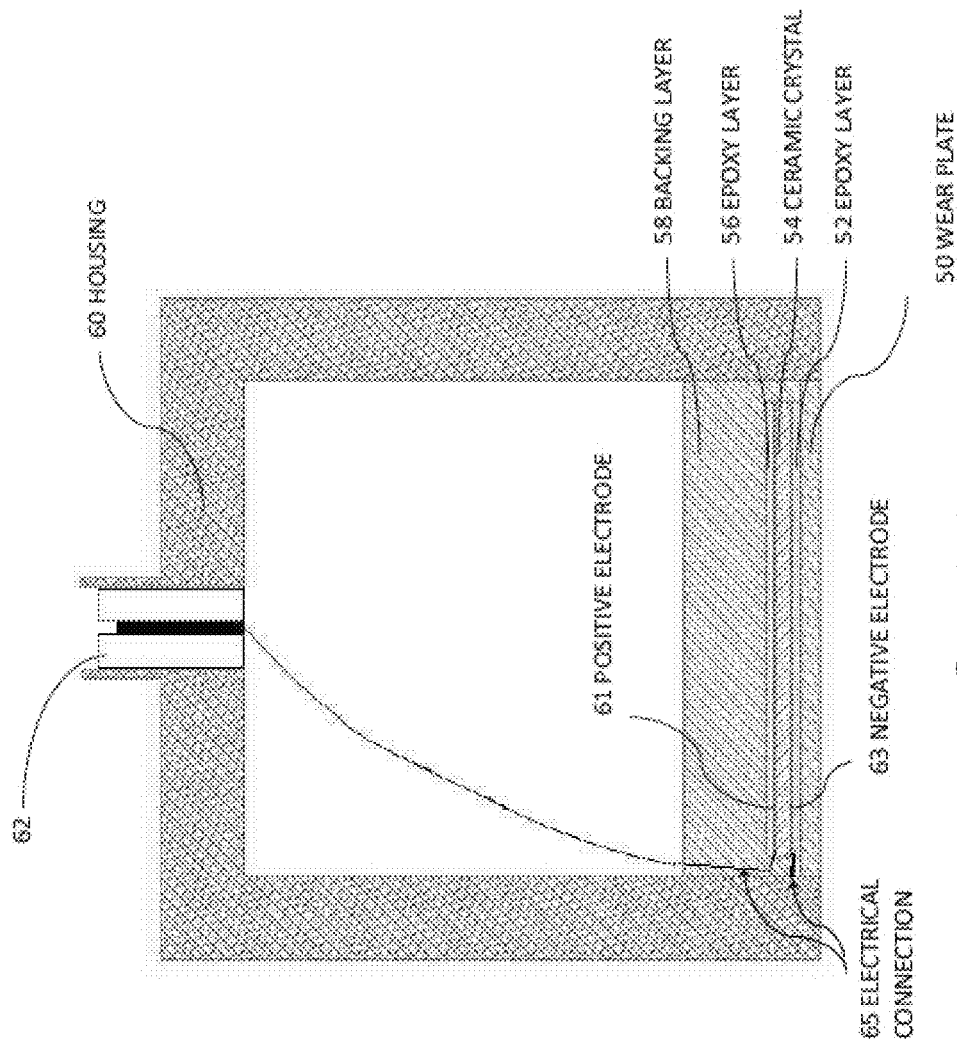
FIG. 21 is a cross-sectional diagram of a conventional ultrasonic transducer.

FIG. 21 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figures 22, 23:
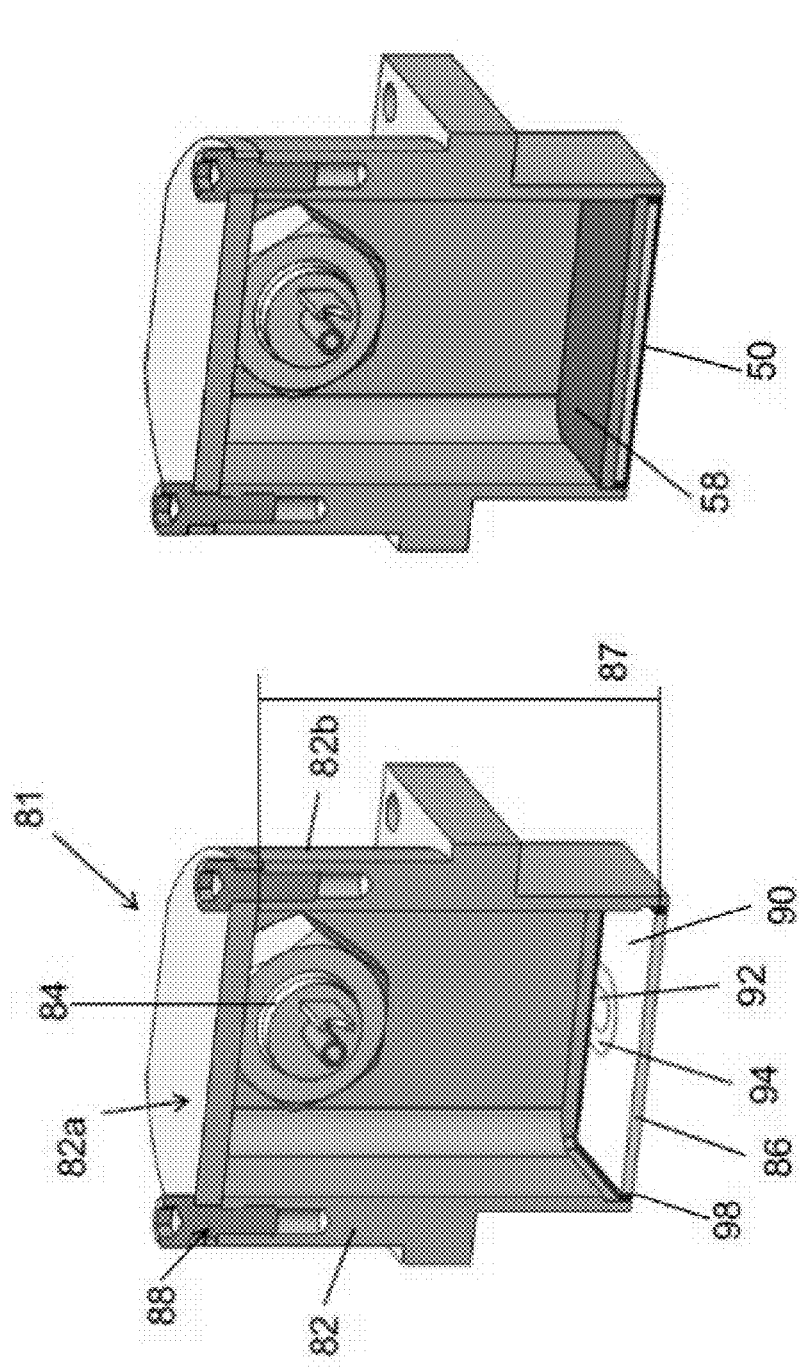
FIG. 22 is a cross-sectional diagram of an ultrasonic transducer of the present disclosure. An air gap is present within the transducer, and no backing layer or wear plate are present.
FIG. 23 is a cross-sectional diagram of an ultrasonic transducer of the present disclosure. An air gap is present within the transducer, and a backing layer and wear plate are present.

FIG. 22 is a cross-sectional view of an ultrasonic transducer 81 of the present disclosure. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and O2-ions. As an example, a PZT (lead zirconate titanate) crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 23.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes (i.e. near eigenfrequency) with a high Q-factor. The vibrating ceramic crystal/disk is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood, or the food and beverage industry, where contamination of the host fluid must be avoided. Such applications might use a wear layer such as chrome, electrolytic nickel, or electroless nickel. Chemical vapor deposition could also be used to apply a layer of poly(p-xylylene) (e.g. Parylene) or other polymers or polymer films. Organic and biocompatible coatings such as silicone or polyurethane are also usable as a wear surface.

One specific application for the acoustophoresis devices and methods disclosed herein is in the processing of a second fluid or particulates entrained in a beverage, such as yeast in beer. Through the use of acoustophoresis, the deflection, fractionation, and separation of the particulates is achievable in macro-scale systems requiring high flow rates. This is an improvement over current filtration processes (filter cartridges, depth filtration, and the like), which routinely become clogged or fouled at the required high flow rates. It is to be further understood that the acoustophoresis devices and processes disclosed herein, through the use of angled acoustic standing waves, may also be coupled with standard filtration process upstream or downstream, such as beverage sheets, filter cartridges, depth filtration, tangential flow filtration (TFF), or other physical or mechanical filtration processes.

Desirably, flow rates through the devices of the present disclosure can be a minimum of 400 mL/min per $cm^2$ of cross-sectional area of the acoustic chamber. Even more desirably, the flow rate can range as high as 600 mL/min/$cm^2$ to 700 mL/min/$cm^2$, or even higher.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An acoustophoresis device, comprising:
   a flow chamber configured to receive an initial mixture of a host fluid and at least one of a second fluid, a cell, or a particulate, the flow chamber defining a direction of mean flow;
   an ultrasonic transducer coupled to the flow chamber, the transducer including a piezoelectric material and configured to create a bulk acoustic standing wave in the flow chamber oriented at an acute angle relative to the direction of mean flow through the flow chamber to deflect the at least one of a second fluid, a cell, or a particulate away from the direction of mean flow; and
   a reflector located on an opposite side of the flow chamber from the ultrasonic transducer.

2. The acoustophoresis device of claim 1, wherein the bulk acoustic standing wave is oriented at an angle of about 20° to about 70° relative to the direction of mean flow through the flow chamber.

3. The acoustophoresis device of claim 1, further comprising an inlet at a first end of the flow chamber and a clarified fluid outlet at a second end of the flow chamber opposite the first end.

4. The acoustophoresis device of claim 3, further comprising a concentrate outlet at the second end of the flow chamber.

5. The acoustophoresis device of claim 3, further comprising a deflection wall below the clarified fluid outlet, the deflection wall extending substantially perpendicular to the direction of mean flow through the flow chamber.

6. The acoustophoresis device of claim 5, further comprising a concentrate outlet at a lower end of the deflection wall.

7. The acoustophoresis device of claim 6, wherein the bulk acoustic standing wave is a multi-dimensional acoustic standing wave that results in an acoustic radiation force having an axial force component that deflects the second fluid, cell, or particulate into the deflection wall.

8. The acoustophoresis device of claim 1, comprising a plurality of ultrasonic transducers arranged in series, each transducer including a piezoelectric material driven by a voltage signal to create a bulk acoustic standing wave in the flow chamber oriented at an angle relative to the direction of mean flow through the flow chamber.

9. The acoustophoresis device of claim 8, wherein each transducer is oriented at the same angle relative to the direction of mean flow through the flow chamber.

10. The acoustophoresis device of claim 1, wherein the bulk acoustic standing wave is a three-dimensional acoustic standing wave.

11. The acoustophoresis device of claim 1, further comprising:
an upper inlet duct through which the initial mixture of the host fluid and the second fluid, cell, or particulate flows into the acoustophoresis device;
a lower inlet duct through which a cell wash flows into the acoustophoresis device;
an upper duct exit through which the host fluid of the initial mixture flows out of the acoustophoresis device;
a middle duct exit through which the cell wash flows out of the acoustophoresis device; and
a lower duct exit where the second fluid, cell, or particulate concentrates after passing from the flow of the initial mixture through the upper inlet duct through the cell wash flow.

12. The acoustophoresis device of claim 1, wherein the bulk acoustic standing wave has a wavelength and the ultrasonic transducer is at least 4 wavelengths away from the reflector.

13. The acoustophoresis device of claim 1, wherein the bulk acoustic standing wave has a frequency and the flow chamber has a size such that the host fluid flows through a large number of nodal planes of the bulk acoustic standing wave in the flow chamber where the acoustic radiation forces deflect the cells, second fluid or particulates, away from the host fluid flow direction.

14. The acoustophoresis device of claim 1, wherein the ultrasonic transducer is operable to create multiple nodal planes across the flow chamber.

15. The acoustophoresis device of claim 14, wherein net acoustic forces of each nodal plane of the multiple nodal plane is repetitive and symmetric on the second fluid, cell, or particulate.

16. The acoustophoresis device of claim 1, wherein a path from the ultrasonic transducer to an interior volume of the flow chamber is acoustically transparent.

17. The acoustophoresis device of claim 1, wherein the ultrasonic transducer is in direct contact with the interior volume of the flow chamber.

18. The acoustophoresis device of claim 1, wherein the ultrasonic transducer is configured to create a bulk acoustic standing wave in the flow chamber with a ratio of acoustic radiation force to viscous drag force on the second fluid, cell, or particulate of greater than 0 to about 1.

19. The acoustophoresis device of claim 1, wherein the ultrasonic transducer is configured to create a bulk acoustic standing wave in the flow chamber with a ratio of acoustic radiation force to viscous drag force on the second fluid, cell, or particulate of less than 0.8.

20. The acoustophoresis device of claim 19, the ratio of acoustic radiation force to viscous drag force on the second fluid, cell, or particulate is less than 0.6.

21. The acoustophoresis device of claim 20, the ratio of acoustic radiation force to viscous drag force on the second fluid, cell, or particulate is less than 0.4.

22. The acoustophoresis device of claim 21, the ratio of acoustic radiation force to viscous drag force on the second fluid, cell, or particulate is less than 0.2.

23. The acoustophoresis device of claim 1, wherein the second fluid, cell, or particulate is deflected away from the host fluid flow direction by the radiation forces of the angular standing wave, such that the deflection angle with respect to the wave angle is determined by a ratio of acoustic radiation force over viscous force on the second fluid, the cell, or the particulate.

24. The acoustophoresis device of claim 1, wherein the bulk acoustic standing wave is oriented at an angle of less than about 20° relative to the direction of mean flow through the flow chamber.

25. A method of separating a second fluid, a cell, or a particulate from a host fluid, the method comprising:
flowing an initial mixture of the host fluid and at least one of the second fluid, cell, or particulate through an acoustophoresis device, the acoustophoresis device comprising:
a flow chamber through which is flowed the initial mixture of the host fluid and at least one of the second fluid, the cell, or the particulate, the flow chamber defining a direction of mean flow;
an ultrasonic transducer coupled to the flow chamber; and
a reflector located on an opposite side of the flow chamber from the at least one ultrasonic transducer; and
driving the ultrasonic transducer to create a bulk angled acoustic standing wave in the flow chamber oriented at an acute angle relative to the direction of mean flow through the flow chamber to deflect the second fluid, cell, or particulate; and
collecting the second fluid, cell, or particulate from the acoustophoresis device.

26. The method of claim 25, wherein the second fluid, cell, or particulate is collected from the acoustophoresis device at a draw rate of about 200 to about 350 milliliters per minute.

27. The method of claim 25, wherein the mixture of the host fluid and at least one of the second fluid, cell, or particulate is flowed through the acoustophoresis device at a flow rate of about 400 to about 700 milliliters per minute.

28. The method of claim 25, wherein the ultrasonic transducer is operated at a frequency of about 0.2 MHz to about 20 MHz.

* * * * *